United States Patent
Elokdah et al.

(10) Patent No.: US 6,599,925 B2
(45) Date of Patent: Jul. 29, 2003

(54) SUBSTITUTED NAPHTHYL BENZOFURAN DERIVATIVES AS INHIBITORS OF PLASMINOGEN ACTIVATOR INHIBITOR-1 (PAI-1)

(75) Inventors: Hassan Mahmoud Elokdah, Yardley, PA (US); Geraldine Ruth McFarlane, Monmouth Junction, NJ (US); Scott Christian Mayer, Bridgewater, NJ (US); David LeRoy Crandall, Doylestown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/174,166

(22) Filed: Jun. 18, 2002

(65) Prior Publication Data

US 2003/0018067 A1 Jan. 23, 2003

Related U.S. Application Data

(60) Provisional application No. 60/299,702, filed on Jun. 20, 2001.

(51) Int. Cl.[7] .............. A61K 31/42; A61K 31/343; C07D 257/04; C07D 407/10; C07D 413/10
(52) U.S. Cl. ............. 514/378; 514/382; 514/469; 548/243; 548/250; 549/414; 549/469; 549/471
(58) Field of Search .............. 514/382, 378, 514/460, 469; 548/243, 250; 549/414, 467, 471

(56) References Cited

U.S. PATENT DOCUMENTS

| | | |
|---|---|---|
| 4,024,273 A | 5/1977 | Brenner et al. |
| 4,496,572 A | 1/1985 | Cross et al. |
| 5,948,795 A | 9/1999 | Berg et al. |
| 5,962,698 A | 10/1999 | Berg et al. |
| 6,110,963 A | 8/2000 | Malamas |

FOREIGN PATENT DOCUMENTS

| | | |
|---|---|---|
| EP | 0 540 051 A | 5/1993 |
| EP | 0 655 439 A2 | 5/1995 |
| GB | 1 464 242 A | 2/1977 |
| WO | WO 95/10513 A1 | 4/1995 |

OTHER PUBLICATIONS

Verner, Erik et al., Journal of Medicinal Chemistry(2001)44(17), 2753–2771.
Nordt et al., The Journal of Clinical Endocrinology & Metabolism, 85(4), 1563–1568 (2000).
Aznar et al., Haemostasis, 24, 243–251 (1994).
Carmeleit et al., Journal of Clinical Invest., 92, 2756–2760 (1993).
Daci et al., Journal of Bone & Mineral Research, 15(8), 1510–1516 (2000).
Biemond et al., Circulation, 91(4), 1175–1181 (1995).
Levi, et al., Circulation, 85(1), 305–312 (1992).
Rocha, et al., Fibrinolysis, 8, 294–303 (1994).
Reilly et al., Arteriosclerosis & Thrombosis 11, 1276–1286 (1991).
Krishnamurti et al., Blood, 69(3), 798–803 (1987).

*Primary Examiner*—Taofiq Solola
(74) *Attorney, Agent, or Firm*—Michael R. Nagy

(57) ABSTRACT

This invention provides compounds which act as inhibitors of plasminogen activator inhibitor-1 (PAI-1) of the formula:

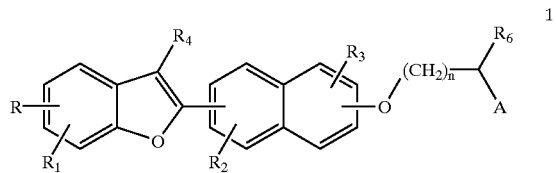

wherein: R, $R_1$, $R_2$, and $R_3$ are H, alkyl, cycloalkyl, —$CH_2$-(cycloalkyl), alkanoyl, halo, hydroxy, aryl, substituted aryl, heteroaryl, substituted heteroaryl, perfluoroalkyl, alkoxy, amino, —NH(alkyl), —N(alkyl)$_2$, or perfluoroalkoxy; $R_4$ is H, alkyl, perflouroalkyl, aryl, substituted aryl, heteroaryl, substituted heteroaryl, alkenyl, alkenyl-aryl, aryl, —$CH_2R_5$, —CH(OH)$R_5$, —C(O)$R_5$, —CH(SH)$R_5$, or —C(S)$R_5$; $R_5$ is H, alkyl, perflouroalkyl, aryl, substituted aryl, heteroaryl, substituted heteroaryl, alkenyl, alkenyl-aryl; $R_6$ is H, alkyl, cycloalkyl, —$CH_2$-cycloalkyl, alkylaryl, aryl, substituted aryl, heteroaryl, or substituted heteroaryl; n is an integer of 0–6; A is COOH, or an acid mimic; or a pharmaceutically acceptable salt or ester form thereof, as well as pharmaceutical compositions and methods using these compounds to treat or prevent conditions resulting from fibrinolytic disorders such as deep vein thrombosis and coronary heart disease, and pulmonary fibrosis.

54 Claims, No Drawings

SUBSTITUTED NAPHTHYL BENZOFURAN DERIVATIVES AS INHIBITORS OF PLASMINOGEN ACTIVATOR INHIBITOR-1 (PAI-1)

This invention relates to the composition and the utility of substituted naphthyl benzofuran derivatives as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (t-PA) and urokinase type plasminogen activator (u-PA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary fibrosis, polycystic ovary syndrome, etc.

U.S. Pat. No. 6,110,963 claims benzofuran derivatives useful in the treatment of hyperglycemia.

WO 95/10513 (Pfizer Inc.) discloses benzothiophenes and related compounds of formula I as estrogen agonists.

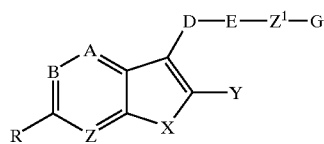

wherein: X=S, O, etc.; Y=alkyl, cycloalkyl, cycloalkenyl, phenyl, a 5- or 6-membered heterocycle, or a bicyclic ring system consisting of a 5- or 6-membered heterocyclic ring fused to a phenyl ring, all optionally substituted.

U.S. Pat. Nos. 5,948,795 and 5,962,698 (Eli Lilly and Company) describe benzothiophene derivatives of formula I and their use as PAI-1 inhibitors.

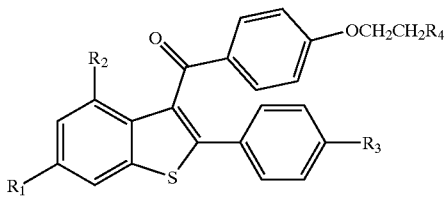

wherein: $R_1$, $R_2$, and $R_3$ are independently —OH, —OCO($C_1$–$C_6$)alkyl, —O(CO)O($C_1$–$C_6$)alkyl, —OCO-phenyl, —OCO-substituted phenyl, or O(CO)O-phenyl; and $R_4$ is N-pyrrolidinyl, N-piperidinyl, or N-hexamethyleneimino.

EP 0 655 439 (Eli Lilly and Company) teaches 5,6 fused ring bicyclic compounds inclusive of indoles, benzofurans, and benzothiophenes corresponding to the general formula I as platelet aggregation inhibitors:

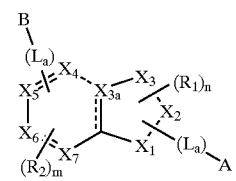

wherein: A is an acidic group linked to the 5-membered ring by linking group $L_a$, where $L_a$ is either a bond or a divalent chain of 1–15 carbon atoms; B is a basic group linked to the 6-membered ring by linking group $L_b$, where $L_b$ is either a bond or a divalent chain of 1–15 carbon atoms.

DESCRIPTION OF THE INVENTION

This invention comprises compounds of formula 1:

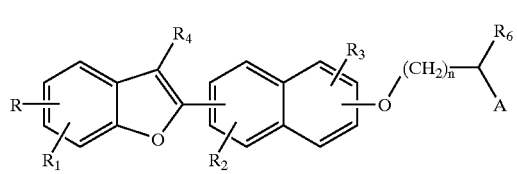

wherein:

R, $R_1$, $R_2$, and $R_3$ are independently selected from hydrogen, $C_1$–$C_6$ alkyl, $C_3$–$C_6$ cycloalkyl, —$CH_2$–$C_3$–$C_6$ cycloalkyl), $C_1$–$C_6$ alkanoyl, halo, hydroxy, aryl, substituted aryl, heteroaryl, substituted heteroaryl, perfluoroalkyl of 1–6 carbon atoms, alkoxy of 1–6 carbon atoms, amino, —NH (alkyl of 1–6 carbon atoms), —N(alkyl of 1–6 carbon atoms)$_2$, and perfluoroalkoxy of 1–6 carbon atoms;

$R_4$ is hydrogen, alkyl of 1–6 carbon atoms, branched alkyl of 1–6 carbon atoms, perflouroalkyl, aryl, substituted aryl, heteroaryl, substituted heteroaryl, alkenyl, alkenyl-aryl, —$CH_2R_5$, —CH(OH)$R_5$, —C(O)$R_5$, —CH(SH)$R_5$, or —C(S)$R_5$ or —(CH$_2$)$_n$—$C_3$ to $C_6$ cycloalkyl wherein n is an integer of from 0 to 2;

$R_5$ is hydrogen, alkyl of 1–6 carbon atoms, branched alkyl of 1–6 carbon atoms, perflouroalkyl, aryl, substituted aryl, heteroaryl, substituted heteroaryl, alkenyl, alkenyl-aryl or —(CH$_2$)$_n$—$C_3$ to $C_6$ cycloalkyl wherein n is an integer of from 0 to 2;

$R_6$ is selected from hydrogen, alkyl of 1–6 carbon atoms, cycloalkyl of 3 to 6 carbon atoms, —$CH_2$-cycloalkyl of 3 to 6 carbon atoms, alkylaryl, aryl, substituted aryl, heteroaryl, or substituted heteroaryl;

n is an integer of 0–6;

A is COOH, or an acid mimic or mimetic; or a pharmaceutically acceptable salt or ester form thereof.

Acid mimic or mimetics which are included in the acidic groups of this invention, as noted in the definition of A, above, particularly include the pharmaceutically useful carboxylic acid mimics or mimetics known in the art, such as those described in R. Silverman, The Organic Chemistry of Drug Design and Drug Action, Academic Press (1992), the contents of which are incorporated herein by reference. Non-limiting examples of these acid mimics include such as tetrazole, $SO_3H$, $PO_3H_2$, tetronic acid, etc., or groups having the formulae:

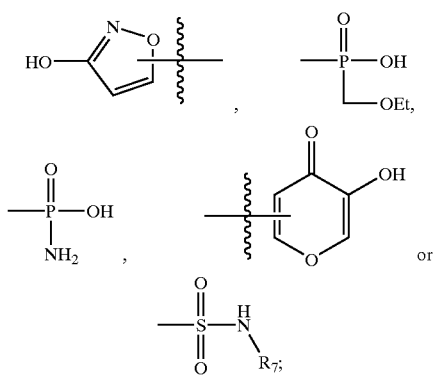

wherein $R_7$ is $C_1$–$C_6$ alkyl, $C_2$–$C_6$ alkenyl, $C_3$–$C_6$ cycloalkyl, —$CH_2$—($C_3$–$C_6$ cycloalkyl), $C_3$–$C_6$ cycloalkenyl, —$CH_2$—($C_3$–$C_6$ cycloalkenyl), optionally substituted aryl or heteroaryl groups or optionally substituted —$C_1$–$C_6$ alkyl-aryl or —$C_1$–$C_6$ alkyl-heteroaryl, with the aryl and heteroaryl groups and their optional substitution as defined herein.

A subset of the compounds of this invention are those of the formula 2:

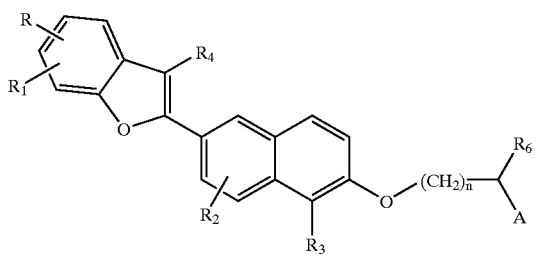

wherein R, $R_1$, $R_2$, $R_3$, $R_4$, $R_6$, A, and n are as defined above, or a pharmaceutically acceptable salt or ester form thereof.

A further subset of the compounds of this invention comprises those having the formula 3:

wherein R, $R_1$, $R_2$, and $R_3$, are as defined above,
n=0
$A_1$ is a carboxylic acid or a tetrazole group[2]
$R_6$ is a hydrogens, $C_1$–$C_6$ alkyl or a benzyl group optionally substituted by from 1 to 3 groups selected from the list of substituents for the aryl or heteroaryl groups described below;
Y represents two single bonded H atoms; one H and one OH; or a double bonded oxygen atom; and
$R_5$ is selected from $C_1$–$C_8$ alkyl, preferably $C_1$–$C_6$ alkyl, $C_3$–$C_6$ cycloalkyl, —$CH_2$—$C_3$–$C_6$ cycloalkyl, or benzyl, the rings of the cycloalkyl and benzyl groups being optionally substituted by from 1 to 3 groups selected from halogen, $C_1$–$C_3$ alkyl, $C_1$–$C_3$ perfluoroalkyl, preferably —$CF_3$, —O—$C_1$–$C_3$ perfluoroalkyl, preferably —O—$CF_3$, $C_1$–$C_3$ alkoxy, —OH, —$NH_2$, or —$NO_2$;
or a pharmaceutically acceptable salt or ester form thereof.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl. It will be understood that the definitions of aryl and heteroaryl also refer to those portions of any aroyl or heteroaroyl groups described herein.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth methals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methyl-morpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —COOR$_5$ wherein R$_5$ is selected from the formulae:

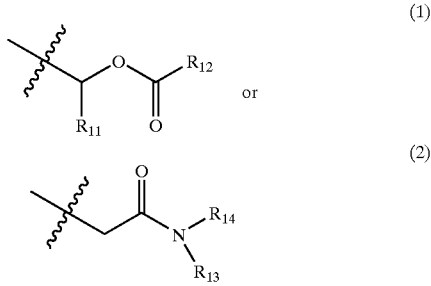

wherein R$_{11}$, R$_{12}$, R$_{13}$, R$_{14}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to C$_1$–C$_6$ alkyl esters, C$_3$–C$_6$ branched alkyl esters, benzyl esters, etc.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds would also be useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be useful in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation. The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzheimer's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor-containing highly active antiretroviral therapy (HAART) for the treatment of diseases which orginate from fibrinolytic impairment and hypercoagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type 1 and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

This invention also comprises methods for the treatment, inhibition, prevention or prophylaxis in a mammal of each of the conditions or maladies listed herein. Each method comprises administering to a mammal in need thereof a pharmaceutically or therapeutically effective amount of a compound of this invention, or a pharmaceutically acceptable salt or ester form thereof.

This invention also provides pharmaceutical compositions comprising a pharmaceutically or therapeutically effective amount of a compound of this invention, or a pharmaceutically acceptable salt or ester form thereof, either alone or in combination with one or more pharmaceutically acceptable carriers or excipients (i.e. pharmaceutically acceptable materials with no pharmacological effects). It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

PROCESS OF THE INVENTION

The compounds of the present invention can be readily prepared according to the methods described in the following reaction schemes or modification thereof using readily available starting materials, reagents and conventional synthetic procedures. It is also possible to make use of variants of these process steps, which in themselves are known to and well within the preparatory skills of medicinal chemists.

Synthesis of substituted 2-naphthylbenzofurans 9 from the appropriate alkyne 2 and o-halo phenols is described in the literature (Torii, *Synlett* 1992, (6), 515–516), Scheme I.

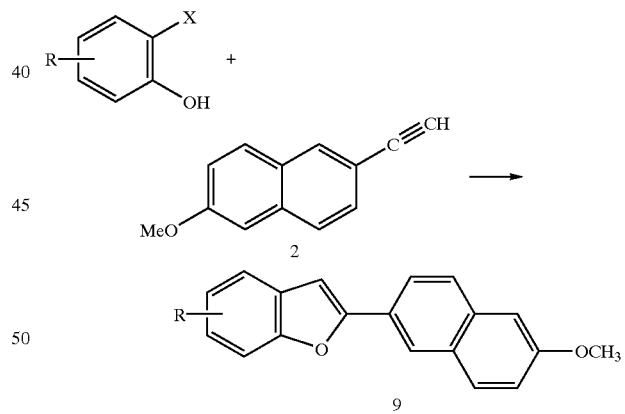

Preparation of 6-bromo-1-chloro-2-naphthol 4 from the corresponding 6-bromo-2-naphthol 3 is described in the literature (Buu-Hoi, *JOC* 1951, 16, 185), Scheme II. 6-Bromo-1-methyl-2-naphthol 7 was prepared as depicted in reaction Scheme II. Reaction of 6-bromo-2-naphthol 3 with aqueous dimethyl amine and aqueous formaldehyde in alcohol afforded the Mannich product 5. Reaction of 5 with acetyl chloride in methylene chloride or chloroform afforded the acetate 6. Hydride reduction of 6 in a solvent such as ethanol followed by basic work-up yielded the desired 6-bromo-1-methyl-2-naphthol 7.

Scheme II

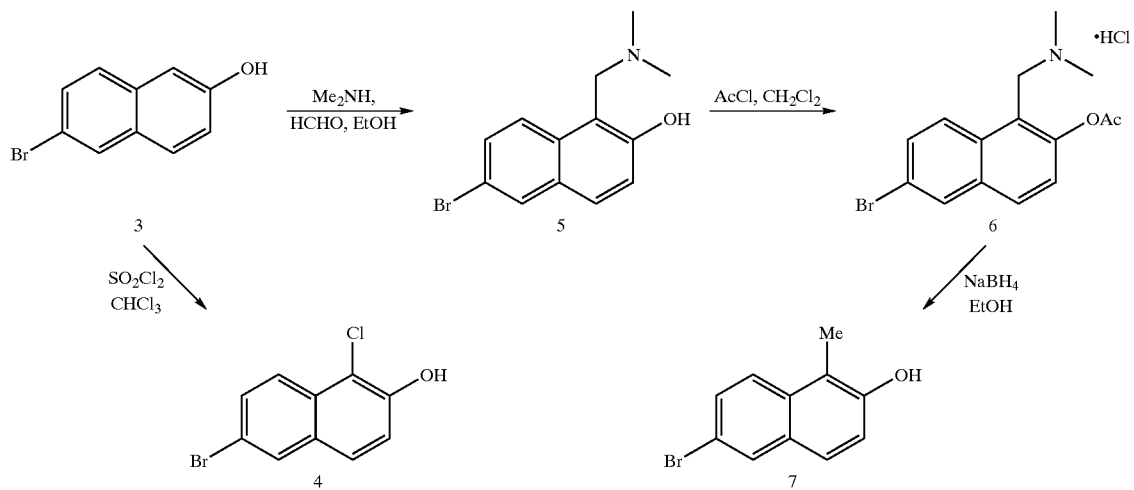

In Scheme III, substituted 2-naphthyl benzofurans 9 were prepared by cross-coupling of substituted bromo naphthalenes with various benzofuran boronic acids 8 using standard palladium-catalyzed cross-coupling procedures under basic conditions in a variety of solvents or mixtures of solvents such as dioxane, water, toluene, alcohol, or THF. Reaction of 9 with acid chlorides or acid anhydrides in the presence of a Lewis acid such as tin(IV)chloride was carried out in a solvent such as methylene chloride or chloroform to afford the 3-acyl benzofuran derivatives 10. Conversion of the methoxy group of 10 to the corresponding hydroxy group was accomplished by treatment of 10 with boron trichloride or boron tribromide in methylene chloride affording derivatives 11. Subsequent bromination of 11 using bromine in acetic acid in the presence of sodium acetate furnished the bromo derivatives 12a. Reduction of 12a or 11 with sodium borohydride in a solvent such as ethanol afforded the alcohols 12b or 12c respectively. Further reduction of 12b or 12c with triethylsilane in a solvent such as methylene chloride under acidic conditions (triflouro acetic acid) afforded the alkyl derivatives 12d and 12e respectively.

Scheme III

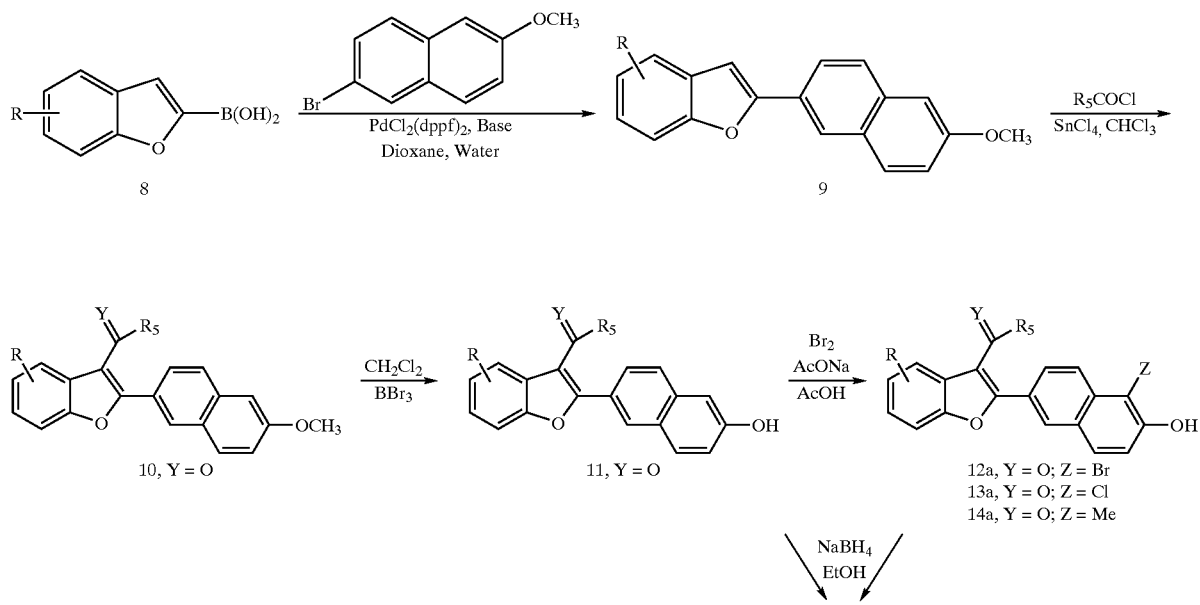

-continued

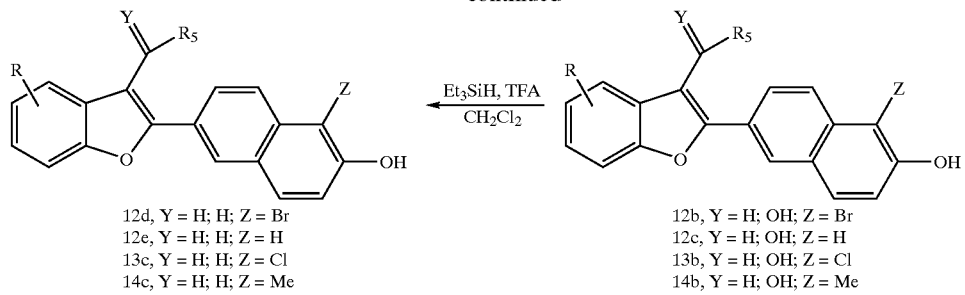

12d, Y = H; H; Z = Br
12e, Y = H; H; Z = H
13c, Y = H; H; Z = Cl
14c, Y = H; H; Z = Me

12b, Y = H; OH; Z = Br
12c, Y = H; OH; Z = H
13b, Y = H; OH; Z = Cl
14b, Y = H; OH; Z = Me

In a similar manner, preparation of substituted 2-naphthyl benzofuran derivatives 13a, 13b, 13c, 14a, 14b, and 14c from 6-bromo naphthalenes 4 or 7, was accomplished by following a modification of the reaction sequence described in Scheme III.

In Scheme IV, compounds 12, 13, or 14 were alkylated with bromoacetonitrile using a base such as potassium carbonate or cesium carbonate in a solvent such as acetone to give the nitrites 15. Conversion of the nitrites 15 to the corresponding tetrazole derivatives 1a was carried out by reacting with sodium azide in the presence of ammonium chloride in a solvent such as DMF at a temperature of 80–100° C. Similarly, alkylation of 12, 13, or 14 with a bromoacetate under basic conditions as described above afforded the acetate derivatives 16. Saponification of 16 furnished the corresponding acetic acid derivatives 1b. Alternatively, coupling of compounds 12, 13, or 14 with hydroxy esters such as phenyllactic acid esters under standard Mitsunobu reaction conditions afforded the substituted esters 17. Hydrolysis of the ester as described above afforded the desired acids 1c.

Scheme IV

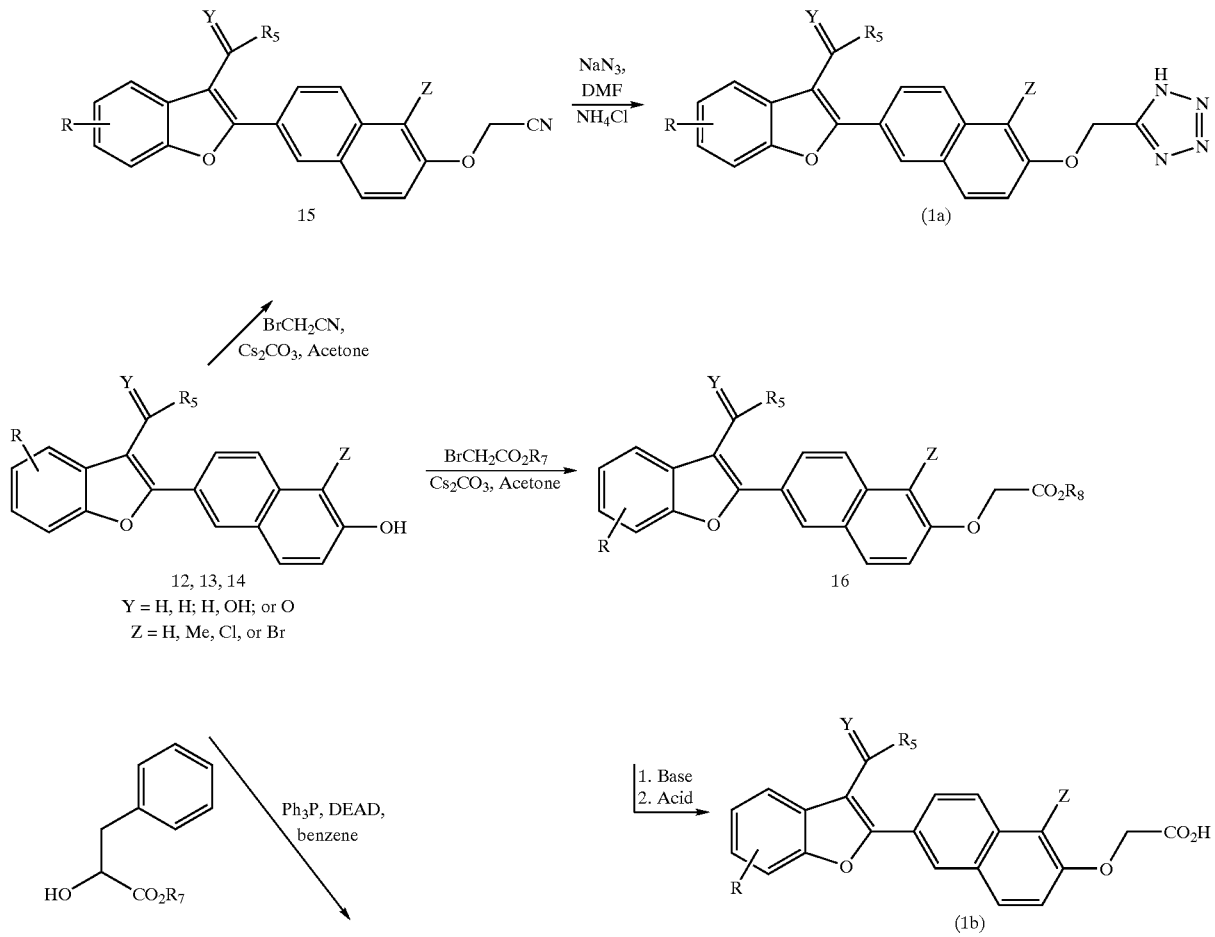

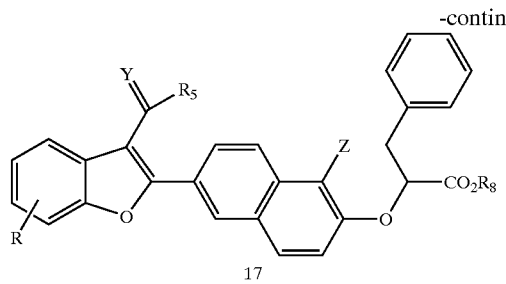

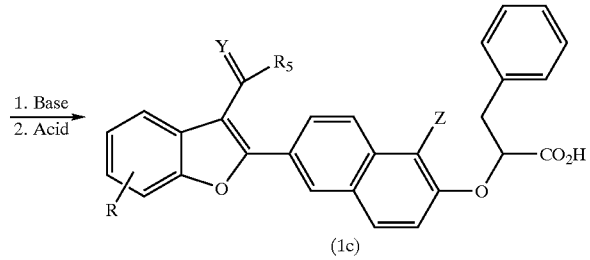

This invention also provides pharmaceutical compositions comprised of substituted naphthyl benzofuran derivatives (I) either alone or in combination with excipients (i.e. pharmaceutically acceptable materials with no pharmacological effects). Such compositions for treating conditions resulting from fibrinolytic disorder such as deep vein thrombosis and coronary heart disease, pulmonary fibrosis, etc.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules.

Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit plasminogen activator inhibitor-1 was established by the following experimental procedures:

Primary Screen for the PAI-1 Inhibition

Test compounds are dissolved in DMSO at a final concentration of 10 mM, then diluted 100×in physiologic buffer. The inhibitory assay is initiated by the addition of the test compound (1–100 μM final concentration, maximum DMSO concentration of 0.2%) in a pH 6.6 buffer containing 140 nM recombinant human plasminogen activator inhibitor-1 (PAI-1; *Molecular Innovations*, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (*American Diagnostica*, Greenwich, Conn.), a chromogenic substrate for tPA, is added and absorbance read at 405 nm at 0 and 60 minutes. Relative PAI-1 inhibition is equal to the residual tPA activity in the presence of the test compounds and PAI-1. Control treatments include the complete inhibition of tPA by PAI-1 at the molar ratio employed (2:1), and the absence of any effect of the test compound on tPA alone.

Assay for Determining $IC_{50}$ of Inhibition of PAI-1

This assay is based upon the non-SDS dissociable interaction between tPA and active PAI-1. Assay plates are initially coated with human tPA (10 μg/ml). Test compounds are dissolved in DMSO at 10 mM, then diluted with physiologic buffer (pH 7.5) to a final concentration of 1–50 μM. The test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (*Molecular Innovations,* Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405nm}$. The quantitation of active PAI-1 bound to tPA at varying concentrations of the test compound is used to determine the $IC_{50}$. Results are analyzed using a logarithmic best-fit equation. The assay sensitivity is 5 ng/ml of human PAI-1 as determined from a standard curve ranging from 0–100 ng/ml.

The compounds of the present invention inhibited Plasminogen Activator Inhibitor-1 as summarized in Table 1.

TABLE I

| Example | $IC_{50}$ (μM) | % Inhibition @ 25 μM |
|---|---|---|
| 1 | 7.7[b] | |
| 2 | — | 43 |
| 3 | 12.7[b] | |
| 4 | 16.6a | |
| 5 | — | 47 |
| 6 | 8.7a | |
| 7 | 14.7[b] | |
| 8 | 11.9[b] | |
| 9 | 18.7[a] | |
| 10 | ND | |
| 11 | — | 24 |
| 12 | ND | |
| 13 | 10.1[a] | |
| 14 | 2.7[a] | |
| 15 | 8.2[a] | |
| 16 | 10.0[a] | |
| 17 | 2.7[a] | |
| 18 | 6.0[b] | |
| 19 | 6.2[b] | |
| 20 | 24.2[a] | |
| 21 | — | 31 |
| 22 | 13.3[a] | |
| 23 | 12.4[a] | |
| 24 | 11.0[a] | |
| 25 | 14.0[a] | |
| 26 | — | 49 |
| 27 | — | 35 |
| 28 | — | 56 |
| 29 | 3.85[a] | |
| 30 | — | 46 |
| 31 | 17.1[b] | |
| 32 | — | 39 |

TABLE I-continued

| Example | $IC_{50}$ (μM) | % Inhibition @ 25 μM |
|---|---|---|
| 33 | 10.4[b] | |
| 34 | 8.17[a] | |
| 35 | 4.39[b] | |
| 36 | 6.54[a] | |
| 37 | 4.59[b] | |

[a]The $IC_{50}$ was determined by the Antibody Assay described above.
[b]The $IC_{50}$ was determined by a modification of the Primary Screen for PAI-1 Inhibition.

EXAMPLE 1

1-{2-[5-Bromo-6-(1H-1,2,3,4-tetraazol-5-ylmethoxy)-2-naphthyl]-1-benzofuran-3-yl}-1-pentanone Step 1

2-(6-methoxy-2-naphthyl)-1-benzofuran

A mixture of 6-methoxy-2-bromonaphthalene (10.1 g, 42.6 mmol), 2-benzofuranboronic acid (8.28 g, 51.1 mmol), potassium carbonate (11.7 g, 84.8 mmol), and [1,1'-bis (diphenylphosphino)ferrocene]dichloropalladium (II) complex with dichloromethane (1:1) (0.887g, 1.09 mmol) in dioxane (420 mL) and water (42 mL) was heated to 69–72° C. for 2 hours. It was allowed to cool to room temperature and solvent evaporated. The residue was paroom temperatureitioned, with heating (because the product is very insoluble) in chloroform/2N hydrochloric acid. The organic phase was washed with water and brine. It was dried over anhydrous magnesium sulfate, filtered and concentrated. The residue was purified by flash chromatography using 15–75% chloroform in hexane and 100% chloroform as eluants. It was dried for 30 minutes at 60° C. to afford 2-(6-methoxy-2-naphthyl)-1-benzofuran as a light yellow-brown solid (9.51 g, 81%): mp 194–195° C.; mass spectrum (+EI, M+) m/z 274. ¹HNMR (400 MHz, DMSO-$d_6$): δ8.4 (s, 1H), 7.9–8.0 (m, 3H), 7.65–7.7 (m, 2H), 7.5 (s, 1H), 7.35 (d, 1H, J=2.5 Hz), 7.2–7.35 (m, 3H), and 3.9 ppm (s, 3H). Elemental Analysis for $C_{19}H_{14}O_2$: Calculated: C, 83.19; H, 5.14; N, 0.00; Found: C, 82.96; H, 4.98; N, 0.01;

Step 2

1-[2-(6-Methoxy-2-naphthyl)-1-benzofuran-3-yl]-1-pentanone

To a stirring mixture of 2-(6-methoxy-2-naphthyl)-1-benzofuran (4.02 g, 14.7 mmol) in chloroform (70 mL) chilled in an ice bath was added valeryl chloride (2.6 mL, 22 mmol). The reaction mixture was chilled to −20° C. and tin (IV) chloride (2.2 mL, 19 mmol) was added, dropwise. The mixture was then stirred at room temperature for one hour and then refluxed for 3 hours, 20 minutes. It was allowed to cool to room temperature and poured into ice. The organic phase was diluted with excess ethyl acetate and washed with water and brine. The organic phase was dried over anhydrous magnesium sulfate, filtered and solvent evaporated.

The residue was purified twice by flash chromatography (Biotage apparatus) using 2% ethyl acetate in hexane and 10–50% chloroform in hexane to afford 1-[2-(6-methoxy-2-naphthyl)-1-benzofuran-3-yl]-1-pentanone as a yellow gum (3.17 g). Mass spectrum (+EI, M+) m/z358. $^1$HNMR (400 MHz, DMSO-d$_6$): δ8.35 (s, 1H), 8.0–8.05 (m, 3H), 7.8 (dd, 1H, J=8.5 Hz and 1.7 Hz), 7.7–7.75 (m, 1H), 7.4–7.45 (m, 3H), 7.25–7.3 (m, 1H), 3.9 (s, 3H), 2.7 (t, 2H, J=7.3 Hz), 1.5–1.6 (m, 2H), 1.1–1.2 (m, 2H), and 0.7 ppm (t, 3H, J=7.4 Hz).

Step 3

1-[2-(6-Hydroxy-2-naphthyl)-1-benzofuran-3-yl]-1-pentanone

To a cooled (−78° C.) solution of 1-[2-(6-methoxy-2-naphthyl)-1-benzofuran-3-yl]-1-pentanone (4.2 g, 12 mmol) in methylene chloride (45 mL), was added, dropwise, 1 N boron tribromide in methylene chloride (25 mL, 25 mmol). The reaction mixture was stirred at room temperature for 3 hours, 45 minutes. The mixture was cooled to −11° C. and quenched, dropwise, with methanol (25 mL), then poured into excess water, and diluted with additional methylene chloride. The organic phase was washed with brine, dried over anhydrous magnesium sulfate, filtered, and solvent evaporated. The residue was purified by flash chromatography (Biotage apparatus) using 5–20% ethyl acetate in hexane as an eluant to afford 1-[2-(6-hydroxy-2-naphthyl)-1-benzofuran-3-yl]-1-pentanone as a yellow solid (3.09 g), mp 148–149° C. Mass spectrum (+EI, M+) m/z 344; $^1$HNMR (400 MHz, DMSO-d$_6$): δ10.1 (d, 1H, J=4.0 Hz), 8.3 (d, 1H, J=1.1 Hz), 8.0–8.05 (m, 1H), 7.95 (d, 1H, J=8.8 Hz), 7.85 (d, 1H, J=8.6 Hz), 7.7–7.75 (m, 2H), 7.35–7.45 (m, 2H), 7.15–7.25 (m, 2H), 2.75 (t, 2H, J=7.4 Hz), 1.5–1.55 (m, 2H), 1.1–1.15 (m, 2H), and 0.7 ppm (t, 3H, J=7.4 Hz). Elemental Analysis for $C_{23}H_{20}O_3$: Calculated: C, 80.21; H, 5.85; N, 0.00. Found: C, 79.92; H, 5.81; N, 0.12.

Step 4

1-[2-(5-Bromo-6-hydroxy-2-naphthyl)-1-benzofuran-3-yl]-1-pentanone

To an ice-cooled mixture of 1-[2-(6-hydroxy-2-naphthyl)-1-benzofuran-3-yl]-1-pentanone (1.59 g, 4.62 mmol) in glacial acetic acid (50 mL) was added potassium acetate (4.54 g, 46.2 mmol). The mixture was stirred at room temperature for 15 minutes and then chilled again in an ice bath. Bromine (0.27 mL, 5.3 mmol) in acetic acid (6 mL) was added dropwise. The mixture was stirred at room temperature for 15 minutes. It was poured into excess water and filtered. The precipitate was dissolved in ethyl acetate, with some warming, and dried over anhydrous magnesium sulfate and filtered. The filtrate was evaporated to dryness to afford 1-[2-(5-bromo-6-hydroxy-2-naphthyl)-1-benzofuran-3-yl]-1-pentanone as a yellow solid (1.85 g), mp 171–172° C. Mass spectrum (+APCl, [M+H]$^+$) m/z 423. $^1$HNMR (400 MHz, DMSO-d$_6$): δ10.95 (s, 1H), 8.4 (d, 1H, J=1.7 Hz), 8.15 (d, 1H, J=9.0 Hz), 8.05–8.1 (m, 2H), 7.95 (dd, 1H, J=8.8 Hz and 2.0 Hz), 7.7–7.75 (m, 1H), 7.35–7.45 (m, 3H), 2.75 (t, 2H, J=7.3 Hz), 1.5–1.6 (m, 2H), 1.1–1.2 (m, 2H), and 0.7 ppm (t, 3H, J=7.3 Hz). Elemental Analysis for $C_{23}H_{19}BrO_3$. 0.25 $H_2O$: Calculated: C, 64.57; H, 4.59; N, 0.00. Found: C, 64.19; H, 4.26; N, 0.05.

Step 5

2-{[1-Bromo-6-(3-pentanoyl-1-benzofuran-2-yl)-2-naphthyl]oxy}acetonitrile

Method A

To an ice-cooled solution of 1-[2-(5-bromo-6-hydroxy-2-naphthyl)-1-benzofuran-3-yl]-1-pentanone (1.2 g, 2.8 mmol) in dry DMF (12 mL) was added sodium hydride (0.315 g, 7.88 mmol of a 60% dispersion on mineral oil) in three portions. Bromoacetonitrile (0.49 mL, 7.0 mmol) was added and the mixture was stirred at room temperature for 1.5 hours, then poured into excess water and acidified with 2N hydrochloric acid. The mixture was extracted with ethyl acetate, washed with brine, dried over anhydrous magnesium sulfate, filtered and concentrated. The residue was purified by flash chromatography (Biotage apparatus) using 15% tert-butyl methyl ether in hexane as an eluant to afford 2-{[1-bromo-6-(3-pentanoyl-1-benzofuran-2-yl)-2-naphthyl]oxy}acetonitrile as a yellow solid (0.776 g, 60%), mp 98–100° C.

Method B:

The mixture of 1-[2-(5-bromo-6-hydroxy-2-naphthyl)-1-benzofuran-3-yl]-1-pentanone (1.46 g, 3.45 mmol) and cesium carbonate (2.36 g, 7.23 mmol) in acetone (16 mL) was stirred at room temperature for 15 minutes. Bromoacetonitrile (0.50 mL, 7.2 mmol) was then added and the mixture was stirred for 4 hours at room temperature then poured into excess water and extracted with ethyl acetate. The organic phase was washed with brine, dried over anhydrous magnesium sulfate and solvent evaporated. The residue was purified by flash chromatography (Biotage apparatus) using 5–20% tert-butyl methyl ether in hexane as an eluant to afford 2-{[1-bromo-6-(3-pentanoyl-1-benzofuran-2-yl)-2-naphthyl]oxy} acetonitrile as a yellow solid (0.989 g), mp 100–102° C. Mass spectrum (−ESI, [M−H]$^-$) m/z 460. $^1$HNMR (400 MHz, DMSO-d$_6$): δ8.55 (d, 1H, J=0.98 Hz), 8.25 (d, 2H, J=9.3 Hz), 8.0–8.05 (m, 2H), 7.7–7.75 (m, 2H), 7.4–7.5 (m, 2H), 5.5 (s, 2H), 2.75 (t, 2H, J=7.2 Hz), 1.5–1.6 (m, 2H), 1.1–1.2 (m, 2H), and 0.7 ppm (t, 3H, J=7.2 Hz). Elemental Analysis for $C_{25}H_{20}BrNO_3$: Calculated: C, 64.95; H, 4.36; N, 3.03. Found: C, 64.71; H, 4.32; N, 2.86.

Step 6

1-{2-[5-Bromo-6-(1H-1,2,3,4tetraazol-5-ylmethoxy)-2-naphthyl]-1-benzofuran-3-yl}-1-pentanone A mixture of 2-{[1-bromo-6-(3-pentanoyl-1-benzofuran-2-yl)-2-naphthyl]oxy}acetonitrile (0.488 g, 1.06 mmol), sodium azide (0.347 g, 5.34 mmol), ammonium chloride (0.289 g, 5.40 mmol) in DMF (10 ml) was heated to 80° C. for 2 hours. The reaction mixture was allowed to cool to room temperature. It was poured into excess water, acidified with 2N hydrochloric acid and extracted with ethyl acetate. The organic phase was washed with water and brine. It was dried over anhydrous magnesium sulfate, filtered and solvent evaporated. The residue was purified by HPLC using 0.1% TFA in 80% acetonitrile/20% water as the mobile phase. The acetonitrile was evaporated and the residue was extracted with ethyl acetate The extract was washed with water and brine, dried over anhydrous magnesium sulfate, filtered and concentrated. The solid was dried at 90° C. for 11 hours affording the title compound as a light yellow solid (0.232 g), m184–185° C. Mass spectrum (+APCl, [M+H]$^+$) m/z 505. $^1$HNMR (400 MHz, DMSO-d$_6$): δ16.8–17.2 (br s, 1H), 8.5 (d, 1H, J=1.7 Hz), 8.25 (t, 2H, J=9.1 Hz), 8.0–8.05 (m, 2H), 7.75–7.8 (m, 2H), 7.4–7.5 (m, 2H), 5.8 (s, 2H), 2.75 (t, 2H, J=7.3 Hz), 1.5–1.6 (m, 2H), 1.1–1.2 (m, 2H), and 0.7 ppm (t, 3H, J=7.3 Hz). Elemental Analysis for C$_{25}$H$_{21}$, BrN$_4$O$_3$: Calculated: C, 59.42; H, 4.19; N, 11.09. Found: C, 59.03; H, 3.98; N, 10.75.

EXAMPLE 2

2-{[6-(3-pentanoyl-1-benzofuran-2-yl)-2-naphthyl]oxy}acetic acid

Step 1

Ethyl 2-{[6-(3-pentanoyl-1-benzofuran-2-yl)-2-naphthyl]oxy}acetate

To an ice-cooled mixture of 1-[2-(6-hydroxy-2-naphthyl)-1-benzofuran-3-yl]-1-pentanone (1.01 g, 2.93 mmol) in DMF (10 mL) was added sodium hydride (0.21 g, 5.25 mmol of 60% dispersion on mineral oil). It was stirred for 50 minutes at room temperature then chilled in an ice bath. Ethyl bromoacetate (0.48 mL, 4.3 mmol) was added, and the reaction mixture was stirred at room temperature for one hour. The mixture was poured into excess water, acidified with 2N hydrochloric acid, and extracted with diethyl ether. The ethereal extract was washed with brine, dried over anhydrous magnesium sulfate, filtered and concentrated. The residue was purified by flash chromatography (Biotage apparatus) using 5–6% tert-butyl methyl ether in hexane as an eluant. The title compound was obtained as a yellow gum (0.749 g, 59%); $^1$HNMR (200 MHz, DMSO-d$_6$): δ8.35 (s, 1H), 7.9–8.1 (m, 3H), 7.8–7.9 (m, 1H), 7.7–7.8 (m, 1H), 7.3–7.5 (m, 4H), 4.95 (s, 2H), 4.2 (q, 2H, J=7.2 Hz), 2.7 (t, 2H, J=7.6 Hz), 1.45–1.65 (m, 2H), 1.0–1.3 (m, 5H), and 0.7 ppm (t, 3H, J=7.6 Hz).

Step 2

2-{[6-(3-Pentanoyl-1-benzofuran-2-yl)-2-naphthyl]oxy}acetic acid

A mixture of ethyl 2-{[6-(3-pentanoyl-1-benzofuran-2-yl)-2-naphthyl]oxy}acetate (0.743 g, 1.73 mmol) and 1N sodium hydroxide (2.7 mL, 2.7 mmol) in ethanol (15 mL) was stirred at room temperature for 1 hour, 10 minutes. The mixture was diluted with excess water and washed with diethyl ether. The aqueous phase was acidified with 2N hydrochloric acid and extracted with ethyl acetate. The organic extract was washed with water and brine. It was dried over anhydrous magnesium sulfate, filtered, and concentrated. The residue crystallized from methanol and dried for 16 hours at 52° C. to afford 2-{[6-(3-pentanoyl-1-benzofuran-2-yl)-2-naphthyl]oxy}acetic acid (0.343 g, 49%), mp 130–132° C. Mass spectrum (-APCl, [M–H]$^-$) m/z 401; $^1$HNMR (400 MHz, DMSO-d$_6$): δ13.0–13.1 (br s, 1H), 8.35 (d, 1H, J=1.5 Hz), 8.0–8.05 (m, 2H), 7.95 (d, 1H, J=8.8 Hz), 7.8 (dd, 1H, J=8.4 Hz and 1.9 Hz), 7.7 (m, 2H), 7.35–7.45 (m, 3H), 7.3 (dd, 1H, J=8.9 Hz and 2.5 Hz), 4.85 (s, 2H), 2.7 (t, 2H, J=7.4 Hz), 1.5–1.55 (m, 2H), 1.1–1.15 (m, 2H), and 0.7 ppm (t, 3H, J=7.4 Hz). Elemental Analysis for C$_{25}$H$_{22}$O$_5$: Calculated: C, 74.61;H, 5.51; N, 0.00. Found: C, 74.29;H, 5.51; N, 0.05.

EXAMPLE 3

1-{2-[6-(1H-1,2,3,4-Tetraazol-5-ylmethoxy)-2-naphthyl]-1-benzofuran-3-yl}-1-pentanone

Step 1

2-{[6-(3-Pentanoyl-1-benzofuran-2-yl)-2-naphthyl]oxy}acetonitrile

Following the procedure described in Method A, Step 5 of Example 1, the title compound was prepared from 1-[2-(6-hydroxy-2-naphthyl)-1-benzofuran-3-yl]-1-pentanone (0.600 g, 1.74 mmol), sodium hydride (0.106 g, 2.65 mmol of a 60% dispersion on mineral oil) and bromoacetonitrile (0.18 mL, 2.6 mmol) in DMF (10 mL). Purification by flash chromatography using 60–80% chloroform in hexane as an eluant afforded a thick yellow oil (0.359 g). $^1$HNMR (200 MHz, DMSO-d$_6$): δ8.45 (s, 1H), 8.0–8.2 (m, 3H), 7.85–7.95 (m, 1H), 7.7–7.8 (m, 1H), 7.65 (d, 1H, J=2.0 Hz), 7.35–7.5 (m, 1H), 5.35 (s, 2H), 2.75 (t, 2H, J=7.4 Hz), 1.45–1.65 (m, 2H), 1.05–1.25 (m, 2H), and 0.7 ppm (t, 3H, J=7.4 Hz).

Step 2

1-{2-[6-(1H-1,2,3,4-Tetraazol-5-ylmethoxy)-2-naphthyl]-1-benzofuran-3-yl}-1-pentanone Following the procedure described in Step 6 of Example 1, the title compound was prepared from 2-{[6-(3-pentanoyl-1-benzofuran-2-yl)-2-naphthyl]oxy}acetonitrile (0.350 g, 0.913 mmol), sodium azide (0.297 g, 4.56 mmol), and ammonium chloride (0.246 g, 4.60) mmol) in DMF (6 mL). Crystallization from acetonitrile (also using charcoal), and drying of the product for 16 hours at 84° C. yielded a light yellow solid (0.0978 g), mp 150–151° C. Mass spectrum (+APCl, [M+H]$^+$) m/z427; $^1$HNMR (400 MHz, DMSO-d$_6$): δ16.8–17.1 (br, 1H), 8.4 (d, 1H, J=1.2 Hz), 8.0–8.05 (m, 3H), 7.85 (dd, 1H, J=8.5 Hz and 1.7 Hz), 7.7 (d, 1H, J=7.5 Hz), 7.65 (d, 1H, J=2.4 Hz) 7.45 (m, 3H), 5.65 (s, 2H), 2.75 (t, 2H, J=7.3 Hz), 1.5–1.6 (m, 2H), 1.1–1.2(m, 2H), and 0.7 ppm (t, 3H, J=7.4 Hz). Elemental Analysis for C$_{25}$H$_{22}$N$_4$O$_3$: Calculated: C, 70.41;H, 5.20; N, 13.14. Found: C, 70.21;H, 5.14; N, 13.23.

EXAMPLE 4

2-{[6-(3-Pentanoyl-1-benzofuran-2-yl)-2-naphthyl]oxy}-3-phenylpropanoic acid

Step 1

Ethyl 2-hydroxy-3-phenylpropanoate

A solution of 2-hydroxy-3-phenylpropanoic acid (2.10 g, 12.6 mmol) in ethanol (50 mL) was saturated with gaseous hydrochloric acid and allowed to stand at room temperature overnight. The reaction mixture was poured into water, neutralized with solid sodium hydrogen carbonate and extracted with ethyl acetate. The organic phase was washed with brine, dried over anhydrous magnesium sulfate, filtered, and concentrated to give ethyl 2-hydroxy-3-phenylpropanoate as a peach-colored oil (2.00 g, 82%); $^1$HNMR (200 MHz, DMSO-d$_6$): δ7.15–7.35 (m, 5H), 5.4–5.6 (br, 1H), 4.15–4.3 (br, 1H), 4.05 (q, 2H, J=7.3 Hz), 2.75–3.0 (m, 2H), and 1.2 ppm (t, 3H, J=7.4 Hz).

Step 2

Ethyl 2-{[6-(3-pentanoyl-1-benzofuran-2-yl)-2-naphthyl]oxy}-3-phenylpropanoate

To an ice-cooled mixture of 1-[2-(6-hydroxy-2-naphthyl)-1-benzofuran-3-yl]-1-pentanone (0.620 g, 1.80 mmol), ethyl 2-hydroxy-3-phenylpropanoate (0.528 g, 2.72 mmol), triphenylphosphine (0.710 g, 2.71 mmol) in benzene (30 mL) was added, dropwise, diisopropyl azodicarboxylate (0.53 mL, 2.7 mmol) in benzene (5 mL). The mixture was stirred at room temperature for 45 minutes, poured into excess water and extracted with ethyl acetate. The organic phase was washed with brine, dried over anhydrous magnesium sulfate, filtered and concentrated. The residue was purified by flash chromatography (Biotage apparatus) using 100% hexane and 2–3.5% ethyl acetate in hexane as eluants. The title compound was obtained as a thick yellow oil (0.670 g). Mass spectrum (+ESI, [M+H]$^+$) m/z 521.5; $^1$HNMR (500 MHz, DMSO-d$_6$): δ8.35 (s, 1H), 8.0 (t, 2H, J=7.8 Hz), 7.95 (d, 1H, J=8.6 Hz), 7.8 (dd, 1H, J=8.6 Hz and 1.7 Hz), 7.7 (d, 1H, J=8.1 Hz), 7.25–7.45 (m, 9H), 5.35 (t, 2H, J=6.5 Hz), 4.05–4.15 (m, 3H), 2.7 (t, 2H, J=7.3 Hz), 1.5–1.55 (m, 2H), 1.1–1.2 (m, 2H), and 0.7 ppm (t, 3H, J=7.4 Hz).

Step 3

2-{[6-(3-Pentanoyl-1-benzofuran-2-yl)-2-naphthyl]oxy}-3-phenylpropanoic acid

A mixture of ethyl 2-{[6-(3-pentanoyl-1-benzofuran-2-yl)-2-naphthyl]oxy}-3-phenylpropanoate (4.10 g, 7.88 mmol), potassium hydroxide (1.35 g, 24.1 mmol) in THF (66 mL) and water (66 mL) was stirred for 2 hours at room temperature. The mixture was poured into excess water and washed with diethyl ether. The aqueous phase was acidified with 2N hydrochloric acid and extracted with ethyl acetate. The organic extract was washed with brine, dried over anhydrous magnesium sulfate, filtered and concentrated. The residue was treated with hexane and the formed solid was crystallized from acetonitrile. Drying at 82° C. for 16 hours afforded the title compound as a light yellow solid (2.87 g), mp 144–145° C. Mass spectrum (+ESI, [M+H]$^+$) m/z 493. $^1$HNMR (500 MHz, DMSO-d$_6$): δ13.1–13.5 (br s, 1H), 8.35 (s, 1H), 7.95–8.05 (m, 2H), 7.9 (d, 1H, J=8.6 Hz), 7.8 (dd, 1H, J=8.6 Hz and 1.7 Hz), 7.7 (dd, 1H, J=7.4 Hz and 0.84 Hz), 7.2–7.45 (m, 9H), 5.2 (q, 2H, J=4.2 Hz), 3.2–3.25 (m, 1H), 2.7 (t, 2H, J=7.3 Hz), 1.5–1.55 (m, 2H), 1.1–1.15 (m, 2H), and 0.7 and ppm (t, 3H, J=7.3 Hz). Elemental Analysis for C$_{32}$H$_{28}$O$_5$: Calculated: C, 78.03; H, 5.73; N, 0.00. Found: C, 77.83; H, 5.55; N, 0.02.

EXAMPLE 5

2-{[1-Bromo-6-(3-pentanoyl-1-benzofuran-2-yl)-2-naphthyl]oxy}acetic acid

Step 1

Ethyl 2-{[1-bromo-6-(3-pentanoyl-1-benzofuran-2-yl)-2-naphthyl]oxy}acetate

Following the procedure described in Method A, Step 5 of Example 1, the title compound was prepared from 1-[2-(5-bromo-6-hydroxy-2-naphthyl)-1-benzofuran-3-yl]-1-pentanone (1.58 g, 3.73 mmol), sodium hydride (0.194 g, 4.85 mmol), and ethyl bromoacetate (0.51 mL, 4.5 mmol) in DMF (15 mL). Purification by flash chromatography using 10% acetone in hexane as an eluant yielded a yellow gum (0.993 g); $^1$HNMR (200 MHz, DMSO-d$_6$): δ8.5 (s, 1H), 8.25 (d, 1H, J=8.5 Hz), 8.15 (d, 1H, J=10 Hz), 7.95–8.1 (m, 2H), 7.75 (d, 1H, J=7.5 Hz), 7.2–7.4 (m, 3H), 5.15 (s, 2H), 4.15 (q, 2H, J=6.7 Hz), 2.75 (t, 2H, J=7.5 Hz), 1.5–1.65 (m, 2H), 1.1–1.3 (m, 4H), and 0.7 ppm (t, 3H, J=7.3 Hz).

Step 2

2-{[1-Bromo-6-(3-pentanoyl-1-benzofuran-2-yl)-2-naphthyl]oxy}acetic acid

The title compound was prepared from ethyl 2-{[1-bromo-6-(3-pentanoyl-1-benzofuran-2-yl)-2-naphthyl]oxy}acetate (0.988 g, 1.94 mmol), and sodium hydroxide (3.9 mL, 3.9 mmol) in ethanol (15 mL) in substantially the same manner as described in Step 2 of Example 2. Purification by flash chromatography on acid treated (phosphoric acid) silica gel using 10–40% ethyl acetate in hexane as an eluant and subsequent crystallization from acetonitrile furnished the title compound as a light yellow solid (0.504 g), mp 146–147° C. Mass spectrum (+APCl, [M+H]$^+$) m/z 481. $^1$HNMR (400 MHz, DMSO-d$_6$): δ13.15–13.3 (br s, 1H), 8.45 (d, 1H, J=1.5 Hz), 8.25 (d, 1H, J=9.0 Hz), 8.15 (d, 1H, J=9.5 Hz), 8.0–8.05 (m, 2H), 7.70–7.75 (m, 1H), 7.4–7.5 (m, 3H), 5.05 (s, 2H), 2.75 (t, 2H, J=7.3 Hz), 1.5–1.6 (m, 2H), 1.1–1.2 (m, 2H), and 0.7 ppm (t, 3H, J=7.3 Hz). Elemental Analysis for C$_{25}$H$_{21}$BrO$_5$.0.30 H$_2$O: Calculated: C, 61.69;H, 4.47; N, 0.00. Found: C, 61.63;H, 4.12; N, 0.07.

EXAMPLE 6

2-({6-[3-(3,3-Dimethylbutanoyl)-1-benzofuran-2-yl]-2-naphthyl}oxy)acetic acid

Step 1

1-[2-(6-Methoxy-2-naphthyl)-1-benzofuran-3-yl]-3,3-dimethyl-1-butanone

Following the procedure described in Step 2 of Example 1, the title compound was prepared from 2-(6-methoxy-2-naphthyl)-1-benzofuran (3.00 g, 10.9 mmol), t-butyl acetyl chloride (2.3 mL, 16 mmol), and tin (IV) chloride (1.7 mL, 14 mmol) in chloroform (60 mL). The reaction mixture was refluxed for 24 hours. Purification by HPLC using 7–8% ethyl acetate in hexane as the mobile phase yielded a yellow solid (1.09 g), mp ~140° C. $^1$HNMR (200 MHz, DMSO-d$_6$): δ8.35 (s, 1H), 7.9–8.1 (m, 3H), 7.7–7.85 (m, 2H), 7.35–7.5 (m, 3H), 7.3 (d, 1H, J=9.0 Hz), 3.95 (s, 3H), 2.75 (s, 2H), and 0.85 ppm (s, 9H).

Step 2

1-[2-(6-Hydroxy-2-naphthyl)-1-benzofuran-3-yl]-3,3-dimethyl-1-butanone

Following the procedure described in Step 3 of Example 1, 1-[2-(6-hydroxy-2-naphthyl)-1-benzofuran-3-yl]-3,3-dimethyl-1-butanone was prepared from 1-[2-(6-methoxy-2-naphthyl)-1-benzofuran-3-yl]-3,3-dimethyl-1-butanone (1.22 g, 3.28 mmol), and boron tribromide (8.5 mL, 8.5 mmol of 1N solution in methylene chloride) in methylene chloride (13 mL), The reaction mixture was stirred for 4 hours. Purification by flash chromatography (Biotage apparatus) using 7.5–15% ethyl acetate in hexane yielded an orange solid (0.385 g), mp 205–207° C. $^1$HNMR (300 MHz, DMSO-d$_6$): δ10.15 (s, 1H), 8.25 (s, 1H), 7.85–8.0 (m, 3H), 7.7–7.8 (m, 2H), 7.35–7.5 (m, 2H), 7.15–7.25 (m, 3H), 2.65 (s, 2H), and 0.85 ppm (s, 9H).

Step 3

2-({6-[3-(3,3-Dimethylbutanoyl)-1-benzofuran-2-yl]-2-naphthyl}oxy)acetic acid

Following the procedure described in Method B, Step 5 of Example 1, ethyl 2-({6-[3-(3,3-dimethylbutanoyl)-1-benzofuran-2-yl]-2-naphthyl}oxy)acetate was prepared from 1-[2-(6-hydroxy-2-naphthyl)-1-benzofuran-3-yl]-3,3-dimethyl-1-butanone (0.241 g, 0.672 mmol), cesium carbonate (0.51 g, 1.4 mmol) and ethyl bromoacetate (0.17 mL, 1.5 mmol) in acetone (10 mL). The reaction mixture was stirred at room temperature for 1.5 hours. Purification by HPLC using 15% tertbutyl methyl ether in hexane as the mobile phase yielded a yellow gum (0.116 g, 0.259 mmol). Ester hydrolysis using potassium hydroxide (0.062 g, 1.10 mmol) in THF (2.5 mL) and water (2.5 mL), according to the procedure described in Step 3 of Example 4, furnished the title compound as an off-white solid (0.0801 g), mp 207–209° C. Mass spectrum (–ESI, [M–H]$^-$) m/z 415. $^1$HNMR (300 MHz, DMSO-d$_6$): δ13.0–13.5 (br s, 1H), 8.3 (d, 1H, J=1.2 Hz), 7.95–8.05 (m, 3H), 7.8 (dd, 1H, J=8.6 Hz and 1.7 Hz), 7.7 (dd, 1H, J=7.0 Hz and 1.5 Hz), 7.4–7.45 (m, 2H), 7.35 (dd, 1H, J=8.9 Hz and 2.6 Hz), 4.85 (s, 2H), 2.65 (s, 2H), and 0.85 ppm (s, 9H). Elemental Analysis for C$_{26}$H$_{24}$O$_5$.0.25H$_2$O: Calculated: C, 74.18; H, 5.87; N, 0.00. Found: C, 74.08; H, 5.76; N, 0.05.

EXAMPLE 7

2-({4-Bromo-6-[3-(3-methylbutanoyl)-1-benzofuran-2-yl]-2-naphthyl}oxy)acetic acid

Step 1

1-[2-(6-Methoxy-2-naphthyl)-1-benzofuran-3-yl]-3-methyl-1-butanone

Following the procedure described in Step 2 of Example 1, 2-(6-methoxy-2-naphthyl)-1-benzofuran (3.00 g, 10.9 mmol), was acylated with isovaleryl chloride (1.9 mL, 16 mmol), in presence of tin (IV) chloride (1.7 mL, 14 mmol) in chloroform (60 mL). Purification by flash chromatography using 15–100% chloroform in hexane as an eluant then by using the Biotage apparatus using 1.5% ethyl acetate in hexane as an eluant yielded the title compound as a yellow wax (1.34 g); $^1$HNMR (200 MHz, DMSO-d$_6$): δ8.35 (s, 1H), 8.0 (d, 3H, J=8.2 Hz), 7.8 (d, 1H, J=10.2 Hz), 7.7 (d, 1H, J=7.7 Hz), 7.35–7.55 (m, 3H), 7.3 (d, 1H, J=8.7 Hz), 3.95 (s, 3H), 2.6 (d, 2H, J=7.7 Hz), 2.0–2.1 (m, 1H), and 0.75 ppm (d, 6H, J=7.7 Hz).

Step 2

1-[2-(6-Hydroxy-2-naphthyl)-1-benzofuran-3-yl]-3-methyl-1-butanone

Following the procedure described in Step 3 of Example 1, 1-[2-(6-hydroxy-2-naphthyl)-1-benzofuran-3-yl]-3-methyl-1-butanone was prepared from 1-[2-(6-methoxy-2-naphthyl)-1-benzofuran-3-yl]-3-methyl-1-butanone (1.32 g, 3.68 mmol), boron tribromide (1M solution in methylene chloride: 9 mL, 9 mmol), in methylene chloride (15 mL). Purification by flash chromatography (Biotage apparatus) using 5–15% ethyl acetate in hexane as an eluant yielded a light yellow solid (0.864 g), mp 181–1822° C.; $^1$HNMR (200 MHz, DMSO-d$_6$): δ10.1 (s, 1H), 8.3 (s, 1H), 7.8–8.1 (m, 3H), 7.65–7.8 (m, 2H), 7.3–7.5 (m, 2H), 7.15–7.3 (m, 2H), 2.65 (d, 2H, J=7.3 Hz), 2.0–2.2 (m, 1H), and 0.85 ppm (d, 6H, J=6.2 Hz).

Step 3

1-[2-(8-Bromo-6-hydroxy-2-naphthyl)-1-benzofuran-3-yl]-3-methyl-1-butanone

Following the procedure described in Step 4 of Example 1, 1-[2-(6-hydroxy-2-naphthyl)-1-benzofuran-3-yl]-3-methyl-1-butanone (0.863 g, 2.51 mmol) was brominated using bromine (0.15 mL, 2.9 mmol), and potassium acetate (2.45 g. 25.0 mmol) in glacial acetic acid (25 mL). Purification by flash chromatography using 15–100% chloroform in hexane as an eluant followed by chromatography on a Biotage apparatus using 15–20% chloroform in hexane as an eluant furnished 1-[2-(8-bromo-6-hydroxy-2-naphthyl)-1-benzofuran-3-yl]-3-methyl-1-butanone as an orange solid (0.623 g), mp 160–161° C. $^1$HNMR (200 MHz, DMSO-d$_6$): δ10.95 (s,1H), 8.4 (s, 1H), 8.2 (d, 1H, J=8.6 Hz), 7.9–8.1 (m, 3H), 7.7–7.8 (d, 1H, J=6.8 Hz), 7.3–7.55 (m, 3H), 2.8 (d, 1H, J=6.8 Hz), 2.0–2.2 (m, 1H), and 0.75 ppm (d, 6H, J=6.3 Hz).

Step 4

Ethyl 2-({4-bromo-6-[3-(3-methylbutanoyl)-1-benzofuran-2-yl]-2-naphthyl}oxy)acetate Following the procedure described in Method B, Step 5 of Example 1, ethyl 2-({4-bromo-6-[3-(3-methylbutanoyl)-1-benzofuran-2-yl]-2-naphthyl}oxy)acetate was prepared from 1-[2-(8-bromo-6-hydroxy-2-naphthyl)-1-benzofuran-3-yl]-3-methyl-1-butanone (0.301 g, 0.711 mmol), cesium carbonate (0.586 g, 1.80 mmol) and ethyl bromoacetate (0.20 mL, 1.8 mmol) in acetone (10 mL). The title compound was obtained as a yellow gum (0.320 g, 88%). $^1$HNMR (200 MHz, DMSO-d$_6$): δ8.5 (s, 1H), 8.25 (d, 1H, J=9.7 Hz), 8.15 (d, 1H, J=9.7 Hz), 8.05 (d, 2H, J=8.7 Hz), 7.75 (d, 1H, J=7.7 Hz), 7.4–7.6 (m, 3H), 5.15 (s, 2H), 4.15–4.3 (m, 2H), 2.7 (d, 2H, J=7.1 Hz), 1.25 (t, 3H, J=7.7 Hz), and 0.75 ppm (d, 6H, J=6.1 Hz).

Step 5

2-({4-Bromo-6-[3-(3-methylbutanoyl)-1-benzofuran-2-yl]-2-naphthyl}oxy)acetic acid Following the procedure described in Step 4 of Example 6, 2-({4-bromo-6-[3-(3-methylbutanoyl)-1-benzofuran-2-yl]-2-naphthyl}oxy)acetic acid was prepared from ethyl 2-({4-bromo-6-[3-(3-methylbutanoyl)-1-benzofuran-2-yl]-2-naphthyl}oxy)acetate (0.310 g, 0.609 mmol), and potassium hydroxide (0.112 g, 2.00 mmol) in THF (10 mL) and water (10 mL). Purification by HPLC using 75% acetonitrile/0.1%TFA in water as the mobile phase yielded a light yellow solid (0.146 g), mp 140–142° C. Mass spectrum (+ESI, [M+H]$^+$) m/z 481. $^1$HNMR (300 MHz, DMSO-d$_6$): δ13.0–13.5 (br s, 1H), 8.45 (d, 1H, J=1.4 Hz), 8.25 (d, 1H, J=8.7 Hz), 8.15 (d, 1H, J=7.0 Hz and 1.5 Hz), 8.0–8.05 (m, 2H), 7.75 (dd, 1H, J=7.0 Hz and 1.5 Hz), 7.4–7.55 (m, 3H), 5.05 (s, 2H), 2.65 (d, 2H, J=6.7 Hz), 2.05–2.15 (m, 1H), and 0.75 ppm (d, 6H, J=6.7 Hz). Elemental Analysis for C$_{25}$H$_{21}$BrO$_5$: Calculated: C, 62.38; H, 4.40; N, 0.00. Found: C, 61.89; H, 4.33; N, 0.12.

EXAMPLE 8

2-({1-Bromo-6-[3-(3,3-dimethylbutanoyl)-1-benzofuran-2-yl]-2-naphthyl}oxy)acetic acid

Step 1

1-[2-(5-Bromo-6-hydroxy-2-naphthyl)-1-benzofuran-3-yl]-3,3-dimethyl-1-butanone

Following the procedure described in Step 4 of Example 1, 1-[2-(6-hydroxy-2-naphthyl)-1-benzofuran-3-yl]-3,3-dimethyl-1-butanone (0.378 g, 1.05 mmol) was brominated using, bromine (0.08 mL, 1.6 mmol), and potassium acetate (1.02 g, 10.4 mmol), in glacial acetic acid (17 mL). Purification by flash chromatography (Biotage apparatus) using 15–20% chloroform in hexane as an eluant furnished the title compound as a dark brown gum (0.203 g). $^1$HNMR (300 MHz, DMSO-$d_6$): δ10.95 (s, 1H), 8.35 (s, 1H), 8.2 (d, 1H, J=8.3 Hz), 8.0 (d, 1H, J=8.3 Hz), 7.95 (t, 2H, J=8.3 Hz), 7.85 (d, 1H, J=8.3 Hz), 7.35–7.55 (m, 3H), 2.65 (s, 2H), and 0.85 ppm (s, 9H).

Step 2

Ethyl 2-({1-bromo-6-[3-(3,3-dimethylbutanoyl)-1-benzofuran-2-yl]-2-naphthyl}oxy) acetate Following the procedure described in Method B, Step 5 of Example 1, ethyl 2-({1-bromo-6-[3-(3,3-dimethylbutanoyl)-1-benzofuran-2-yl]-2-naphthyl}oxy)acetate was prepared from 1-[2-(5-bromo-6-hydroxy-2-naphthyl)-1-benzofuran-3-yl]-3,3-dimethyl-1-butanone (0.201 g, 0.460 mmol), cesium carbonate (0.396 g, 1.22 mmol), and ethyl bromoacetate (0.13 mL, 1.2 mmol) in acetone (10 mL). Purification by flash chromatography using 100% hexane and 1–4% tert-butyl methyl ether as an eluant yielded a yellow gum (0.775 g, 32%); $^1$HNMR (200 MHz, DMSO-$d_6$): 8.45 (s, 1H), 8.3 (d, 1H, J=9.0 Hz), 8.2 (d, 1H, J=9.0 Hz), 7.95–8.1 (m, 2H), 7.7–7.8 (m, 1H), 7.2–7.4 (m, 3H), 5.15 (s, 2H), 4.15–4.3 (m, 2H), 2.7 (s, 2H), 1.25 (t, 3H, J=7.6 H), and 0.85 ppm (s, 9H).

Step 3

2-({1-Bromo-6-[3-(3,3-dimethylbutanoyl)-1-benzofuran-2-yl]-2-naphthyl}oxy)acetic acid Following the procedure described in Step 4 of Example 6, ethyl 2-({1-bromo-6-[3-(3,3-dimethylbutanoyl)-1-benzofuran-2-yl]-2-naphthyl}oxy) acetate (0.076 g, 0.145 mmol) was hydrolyzed with potassium hydroxide (0.0275 g, 0.490 mmol) in THF (5 mL) and water (5 mL) to yield the title compound as a yellow solid (0.0611 g), mp 151–153° C. Mass spectrum (+ESI, [M+H]$^+$) m/z 495; $^1$HNMR (300 MHz, DMSO-$d_6$): δ13.1–13.5 (br s, 1H), 8.45 (d, 1H, J=1.4 Hz), 8.25 (d, 1H, J=8.9 Hz), 8.15 (d, 1H, J=9.1 Hz), 7.95–8.0 (m, 2H), 7.7–7.75 (m, 1H), 5.05 (s, 2H), 2.65 (s, 2H), and 0.85 ppm (s, 9H). Elemental Analysis for $C_{26}H_{23}BrO_5$: Calculated: C, 63.04; H, 4.68; N, 0.00. Found: C, 62.87; H, 4.57; N, 0.24.

EXAMPLE 9

1-{2-[5-Bromo-6-(1H-1,2,3,4-tetraazol-5-ylmethoxy)-2-naphthyl]-1-benzofuran-3-yl}-3-methyl-1-butanone Step 1

2-({1-Bromo-6-[3-(3-methylbutanoyl)-1-benzofuran-2-yl]-2-naphthyl}oxy)acetonitrile Following the procedure described in Method B, Step 5 of Example 1, 2-({1-bromo-6-[3-(3-methylbutanoyl)-1-benzofuran-2-yl]-2-naphthyl}oxy)acetonitrile was prepared from 1-[2-(8-bromo-6-hydroxy-2-naphthyl)-1-benzofuran-3-yl]-3-methyl-1-butanone (0.306 g, 0.723 mmol), cesium carbonate (0.595 g, 1.83 mmol), and bromo acetonitrile (0.13 mL, 1.8 mmol) in acetone (10 mL). Purification by HPLC using 15% ethyl acetate in hexane as the mobile phase yielded the title compound as a yellow solid (0.209 g). $^1$HNMR (200 MHz, DMSO-$d_6$): δ8.55 (s, 1H), 8.3 (d, 2H, J=7.7 Hz), 8.0–8.15 (m, 2H), 7.7–7.8 (m, 2H), 7.4–7.6 (m, 2H), 5.5 (s, 2H), 2.7 (d, 2H, J=6.6 Hz), 2.0–2.2 (m, 2H), and 0.75 ppm (d, 6H, J=6.6 Hz).

Step 2

1-{2-[5-Bromo-6-(1H-1,2,3,4-tetraazol-5-ylmethoxy)-2-naphthyl]-1-benzofuran-3yl}-3-methyl-1-butanone Following the procedure described in Step 6, of Example 1, the title compound was prepared from 2-({1-bromo-6-[3-(3-methylbutanoyl)-1-benzofuran-2-yl]-2-naphthyl}oxy) acetonitrile (0.207 g, 0.448 mmol), sodium azide (0.147 g, 2.26 mmol) and ammonium chloride (0.125 g, 2.34 mmol) in DMF (10 mL). The compound was purified by HPLC using 75% acetonitrile/0.1% TFA in water. Drying for 14 hours at 90° C. yielded a cream-colored solid (0.0966 g), mp 176–177° C. Mass spectrum (−ESI, [M−H]$^−$) m/z 503. $^1$HNMR (500 MHz, DMSO-$d_6$): δ16.8–17.1 (br s, 1H), 8.5 (d, 1H, J=1.7 Hz), 8.25 (q, 2H, J=8.2 Hz), 8.0–8.05 (m, 2H), 7.75 (q, 2H, J=8.3 Hz), 7.4–7.5 (m, 3H), 5.8 (s, 2H), 2.7 (d, 2H, J=6.9 Hz), 2.05–2.15 (m, 1H), and 0.75 ppm (d, 6H, J=6.6 Hz). Elemental Analysis for $C_{25}H_{21}BrN_4O_3.0.10$ $H_2O$: Calculated: C, 59.20; H, 4.21; N, 11.05. Found: C, 58.84; H, 3.80; N, 10.83.

EXAMPLE 10

2-({6-[3-(2-Cyclopentylacetyl)-1-benzofuran-2-yl]-2-naphthyl}oxy)acetic acid

Step 1

2-Cyclopentyl-1-[2-(6-methoxy-2-naphthyl)-1-benzofuran-3-yl]-1-ethanone

Following the procedure described in Step 2 of Example 1, 2-(6-methoxy-2-naphthyl)-1-benzofuran (6.00 g, 21.9 mmol) was acylated with 2-cyclopentylacetyl chloride (3.51 g, 23.9 mmol) using tin (IV) chloride (2.8 mL, 24 mmol) in carbon disulfide (120 mL). Purification by flash chromatography (Biotage apparatus) using 10–25% chloroform in hexane and 0.5–1% ethyl acetate in hexane as eluants furnished the title compound as a yellow gum (4.98 g); $^1$HNMR (200 MHz, DMSO-$d_6$): δ8.35 (s, 1H), 8.0 (d, 3H, J=8.7 Hz), 7.8 (d, 1H, J=8.7 Hz), 7.7–7.8 (m, 1H), 7.35–7.5 (m, 3H), 7.2–7.35 (m, 1H), 3.95 (s, 3H), 2.75 (d, 2H, J=7.7 Hz), 2.1–2.3 (m, 1H), 1.5–1.75 (m, 2H), 1.3–1.5 (m, 4H), and 0.8–1.1 ppm (m, 2H).

Step 2

2-Cyclopentyl-1-[2-(6-hydroxy-2-naphthyl)-1-benzofuran-3-yl]-1-ethanone

Following the procedure described in Step 3 of Example 1, 2-cyclopentyl-1-[2-(6-hydroxy-2-naphthyl)-1-benzofuran-3-yl]-1-ethanone was prepared from 2-cyclopentyl-1-[2-(6-methoxy-2-naphthyl)-1-benzofuran-3-yl]-1-ethanone (2.92 g, 7.59 mmol), and boron tribromide (18 mL, 18 mmol of a 1M solution in methylene chloride) in methylene chloride (30 mL). Purification by flash chromatography (Biotage apparatus) using 5–20% ethyl acetate in hexane as an eluant furnished the title compound as a yellow solid (2.24 g), mp 189–190° C.; $^1$HNMR (300 MHz, DMSO-$d_6$): δ10.1 (s, 1H), 8.3 (s, 1H), 7.95 (q, 2H, J=8.2 Hz), 7.85 (d, 1H, J=8.5 Hz), 7.65–7.8 (m, 2H), 7.35–7.45 (m, 2H), 7.15–7.25 (m, 2H), 2.75 (d, 2H, J=8.5 Hz), 2.15–2.3 (m, 1H), 1.55–1.7 (m, 2H), 1.3–1.5 (m, 4H), and 0.9–1.0 ppm (m, 2H).

Step 3

Ethyl 2-({6-[3-(2-cyclopentylacetyl)-1-benzofuran-2-yl]-2-naphthyl}oxy)acetate

Following the procedure described in Method B, Step 5 of Example 1, ethyl 2-({6-[3-(2-cyclopentylacetyl)-1-benzofuran-2-yl]-2-naphthyl}oxy)acetate was prepared from 2-cyclopentyl-1-[2-(6-hydroxy-2-naphthyl)-1- benzofuran-3-yl]-1-ethanone (0.420 g, 1.13 mmol), cesium carbonate (0.774 g, 2.38 mmol), ethyl bromoacetate (0.26 mL, 2.3 mmol) in acetone (10 mL). Purification by flash chromatography using 5–10% tert-butyl methyl ether in hexane as an eluant yielded a yellow gum (0.326 g). $^1$HNMR (300 MHz, DMSO-$d_6$): δ8.4 (s, 1H), 7.95–8.1 (m, 3H), 7.85 (d, 1H, J=9.2 Hz), 7.75 (d, 1H, J=9.2 Hz), 7.3–7.5 (m, 4H), 4.95 (s, 2H), 4.25 (q, 2H, J=7.7 Hz), 2.75 (d, 2H, J=6.9 Hz), 2.15–2.3 (m, 1H), 1.55–1.7 (m, 2H), 1.3–1.5 (m, 4H), 1.25 (t, 3H, J=7.7 Hz), and 0.8–1.05 ppm (m, 2H).

Step 4

2-({6-[3-(2-Cyclopentylacetyl)-1-benzofuran-2-yl]-2-naphthyl}oxy)acetic acid

Following the procedure described in Step 4 of Example 6, ethyl 2-({6-[3-(2-cyclopentylacetyl)-1-benzofuran-2-yl]-2-naphthyl}oxy)acetate (0.324 g, 0.710 mmol), was hydrolyzed with potassium hydroxide (0.120 g, 2.14 mmol) in THF (5 mL) and water (5 mL). Crystallization from acetonitrile yielded the title compound as a cream-colored solid (0.179 g), mp 177–178° C. Mass spectrum (–ESI, [M–H]$^-$) m/z 427; $^1$HNMR (500 MHz, DMSO-$d_6$): δ12.9–13.4 (br s, 1H), 8.35 (d, 1H, J=1.1 Hz), 7.95–8.05 (m, 3H), 7.8 (dd, 1H, J=8.5 and 1.8 Hz), 7.7 (d, 1H, J=7.6 Hz), 7.4–7.45 (m, 3H), 7.3 (dd, 1H, J=8.9 Hz and 2.5 Hz), 4.85 (s, 2H), 2.75 (d, 2H, J=7.0 Hz), 2.15–2.25 (m, 1H), 1.6–1.65 (m, 2H), 1.35–1.45 (m, 4H), and 0.95–1.0 ppm (m, 2H). Elemental Analysis for $C_{27}H_{24}O_5$: Calculated: C, 75.68; H, 5.65; N, 0.00. Found: C, 75.38; H, 5.46; N, 0.02.

EXAMPLE 11

2-({1-Bromo-6-[3-(2-cyclopentylethyl)-1-benzoluran-2-yl]-2-naphthyl}oxy)acetic acid Step 1

2-Cyclopentyl-1-[2-(6-methoxy-2-naphthyl)-1-benzofuran-3-yl]-1-ethanol

To a mixture of 2-cyclopentyl-1-[2-(6-methoxy-2-naphthyl)-1-benzofuran-3-yl]-1-ethanone (2.03 g, 5.28 mmol) in ethanol (25 mL) cooled in an ice bath was added sodium borohydride (1.05 g, 27.7 mmol) in three portions. The reaction mixture was stirred for about 18 hours at room temperature and then concentrated. The residue was partitioned in warm ethyl acetate and water. The organic phase was washed with water and brine. It was dried over anhydrous magnesium sulfate, filtered and concentrated to afford 2-cyclopentyl-1-[2-(6-methoxy-2-naphthyl)-1-benzofuran-3-yl]-1-ethanol as a cream-colored solid (1.84 g), mp 176–177° C. $^1$HNMR (200 MHz, DMSO-$d_6$): δ8.2 (s, 1H), 7.8–8.0 (m, 4H), 7.6 (d, 1H, J=7.5 Hz), 7.2–7.45 (m, 4H), 5.4 (s, 1H), 5.1–5.2 (br, 1H), 3.9 (s, 3H), 1.95–2.15 (br m, 1H), 1.8–1.95 (br m, 2H), 1.2–1.6 (br m, 4H), and 1.0–1.2 ppm (br m, 2H).

Step 2

3-(2-Cyclopentylethyl)-2-(6-methoxy-2-naphthyl)-1-benzofuran

To a mixture of 2-cyclopentyl-1-[2-(6-methoxy-2-naphthyl)-1-benzofuran-3-yl]-1-ethanol (1.84 g, 4.77 mmol) in methylene chloride (50 mL) cooled in an ice bath was added triethylsilane (1.5 mL, 9.5 mmol). Trifluoroacetic acid (3.7 mL, 48 mmol) was then added drop-wise. The reaction mixture was stirred at room temperature for 1 hour, then concentrated. The residue was partitioned in ethyl acetate and sodium bicarbonate solution. The organic phase was washed with water, brine, dried over anhydrous magnesium sulfate, filtered and concentrated. Purification by flash chromatography (Biotage apparatus) using 100% hexane as an eluant afforded 3-(2-cyclopentylethyl)-2-(6-methoxy-2-naphthyl)-1-benzofuran as a light beige wax (1.05 g). $^1$HNMR (200 MHz, DMSO-$d_6$): δ8.25 (s, 1H), 7.95 (d, 2H, J=7.7 Hz), 7.85 (d, 1H, J=7.7 Hz), 7.55–7.75 (m, 2H), 7.2–7.4 (m, 4H), 3.9 (s, 3H), 2.95–3.05 (m, 2H), 1.4–2.0 (br m, 9H), and 1.1–1.3 ppm (br m, 2H).

Step 3

6-[3-(2-Cyclopentylethyl)-1-benzofuran-2-yl]-2-naphthol

Following the procedure described in Step 3 of Example 1, 6-[3-(2-cyclopentylethyl)-1-benzofuran-2-yl]-2-naphthol was prepared from 3-(2-cyclopentylethyl)-2-(6-methoxy-2-naphthyl)-1-benzofuran (1.04 g, 2.81 mmol), and boron tribromide (1M solution, 8 mL, 8 mmol) in methylene chloride (25 mL). The compound was purified by flash chromatography (Biotage apparatus) using 3–6% ethyl acetate in hexane as an eluant. Treating with methylene chloride/hexane afforded the title compound as a light peach solid (0.675 g), mp 118–119° C. $^1$HNMR (300 MHz, DMSO-$d_6$): δ9.95 (s, 1H), 8.15 (s, 1H), 7.75–7.9 (m, 3H), 7.65 (d, 1H, J=7.1 Hz), 7.6 (d, 1H, J=8.7 Hz), 7.25–7.35 (m, 2H), 7.1–7.2 (m, 2H), 3.0 (t, 2H, J=7.9 Hz), 1.65–1.95 (m, 5H), 1.4–1.6 (m, 4H), and 1.0–1.3 ppm (m, 2H).

Step 4

1-Bromo-6-[3-(2-cyclopentylethyl)-1-benzofuran-2-yl]-2-naphthol

Following the procedure described in Step 4 of Example 1, 6-[3-(2-cyclopentylethyl)-1-benzofuran-2-yl]-2-naphthol (0.671 g, 1.88 mmol) was brominated with bromine (0.11 mL, 2.2 mmol) and potassium acetate (1.91 g, 19.5 mmol) in glacial acetic acid (19 mL). Purification by flash chromatography using 100% hexane and 1–30% chloroform in hexane as eluants afforded 1-bromo-6-[3-(2-cyclopentylethyl)-1-benzofuran-2-yl]-2-naphthol as a light brown semi-solid (0.609 g). $^1$HNMR (300 MHz, DMSO-$d_6$): δ10.75 (s, 1H), 8.25 (s, 1H), 8.15 (d, 1H, J=8.6 Hz), 7.95–8.0 (m, 2H), 7.7 (d, 1H, J=8.6 Hz), 7.6 (d, 1H, J=8.6 Hz), 7.25–7.4 (m, 3H), 3.0 (t, 2H, J=8.6 Hz), 1.65–1.95 (m, 5H), 1.4–1.65 (m, 4H), and 1.1–1.25 ppm (m, 2H).

Step 5

Ethyl 2-({1-bromo-6-[3-(2-cyclopentylethyl)-1-benzofuran-2-yl]-2-naphthyl}oxy)acetate Following the procedure described in Method B, Step 5 of Example 1, ethyl 2-({1-bromo-6-[3-(2-cyclopentylethyl)-1-benzofuran-2-yl]-2-naphthyl}oxy)acetate was prepared from 1-bromo-6-[3-(2-cyclopentylethyl)-1-benzofuran-2-yl]-2-naphthol (0.286 g, 0.657 mmol), cesium carbonate (0.446 g, 1.37 mmol) and ethyl bromoacetate (0.15 mL, 1.4 mmol) in acetone (10 mL). Crystallization from acetonitrile and drying for 10 hours at 80° C. furnished a light beige solid (0.187 g), mp 115–120° C. $^1$HNMR (300 MHz, DMSO-$d_6$): δ8.35 (s, 1H), 8.25 (d, 1H, J=7.5Hz), 8.05–8.15 (m, 2H), 7.7 (d, 1H, J=7.5 Hz), 7.65 (d, 1H, J=7.5 Hz), 7.5 (d, 1H, J=8.3 Hz), 7.2–7.3 (m, 2H), 5.15 (s, 1H), 4.2 (q, 2H, J=7.5 Hz), 3.05 (t, 2H, J=7.5 Hz), 1.65–2.0 (m, 5H), 1.4–1.65 (m, 4H), and 1.15–1.25 ppm (m, 5H).

Step 6

2-({1-Bromo-6-[3-(2-cyclopentylethyl)-1-benzofuran-2-yl]-2-naphthyl}oxy)acetic acid Following the procedure described in Step 4 of Example 6, ethyl 2-({1-bromo-6-[3-(2-cyclopentylethyl)-1-benzofuran-2-yl]-2-naphthyl}oxy)acetate (0.180 g, 0.345 mmol) was hydrolyzed with potassium hydroxide (0.077 g, 1.4 mmol) in THF (5 mL) and water (5 mL). Crystallization from acetonitrile and drying for 12 hours at 80° C. yielded 2-({1-bromo-6-[3-(2-cyclopentylethyl)-1-benzofuran-2-yl]-2-naphthyl}oxy)acetic acid as a cream-colored solid (0.0807 g), mp 155–156° C. Mass spectrum (-ESI, [M–H]$^-$) m/z 491; $^1$HNMR (500 MHz, DMSO-d$_6$): δ13.0–13.5 (br s, 1H), 8.35 (d, 1H, J=1.2 Hz), 8.25 (d, 1H, J=8.9 Hz), 8.10 (d, 1H, J=9.0 Hz), 8.05 (dd, 1H, J=9.0 Hz and 1.7 Hz), 7.7 (d, 1H, J=7.8 Hz), 7.6 (d, 1H, J=7.9 Hz), 7.45 (d, 1H, J=9.2 Hz), 7.35–7.4 (m, 1H), 7.30–7.35 (m, 1H), 5.0 (s, 2H), 3.0 (t, 2H, J=7.9 Hz), 1.8–1.9 (m, 1H), 1.7–1.8 (m, 4H), 1.5–1.6 (m, 2H), 1.4–1.5 (m, 2H), and 1.15–1.25 ppm (m, 2H). Elemental Analysis for C$_{27}$H$_{25}$BrO$_4$: Calculated: C, 65.13; H, 5.16; N, 0.00. Found: C, 64.83; H, 4.94; N, 0.06.

EXAMPLE 12

5-[({1-Bromo-6-[3-(2-cyclopentylethyl)-1-benzofuran-2-yl]-2-naphthyl}oxy)methyl]-1H-1,2,3,4-tetraazole Step 1

2-({1-Bromo-6-[3-(2-cyclopentylethyl)-1-benzofuran-2-yl]-2-naphthyl}oxy)acetonitrile Following the procedure described in Method B, Step 5 of Example 1, 2-({1-bromo-6-[3-(2-cyclopentylethyl)-1-benzofuran-2-yl]-2-naphthyl}oxy)acetonitrile was prepared from 1-bromo-6-[3-(2-cyclopentylethyl)-1-benzofuran-2-yl]-2-naphthol (0.304 g, 0.698 mmol), cesium carbonate (0.477 g, 1.46 mmol) and bromoacetonitrile (0.10 mL, 1.4 mmol) in acetone (10 mL). Purification by flash chromatography using 5% tert-butyl methyl ether in hexane as an eluant yielded a light brown gum (0.215 g). $^1$HNMR (200 MHz, DMSO-d$_6$): δ8.4 (s, 1H), 8.25 (t, 2H, J=8.4 Hz), 8.1 (d, 1H, J=8.7Hz), 7.55–7.8 (m, 3H), 7.25–7.45 (m, 2H), 5.45 (s, 2H), 2.95–3.15 (m, 2H), 1.35–2.0 (m, 2H), and 1.05–1.35 ppm (m, 2H).

Step 2

5-[({1-Bromo-6-[3-(2-cyclopentylethyl)-1-benzofuran-2-yl]-2-naphthyl}oxy)methyl]-1H-1,2,3,4-tetraazole Following the procedure described in Step 6 of Example 1, 5-[({1-bromo-6-[3-(2-cyclopentylethyl)-1-benzofuran-2-yl]-2-naphthyl}oxy)methyl]-1H-1,2,3,4-tetraazole was prepared from 2-({1-bromo-6-[3-(2-cyclopentylethyl)-1-benzofuran-2-yl]-2-naphthyl}oxy) acetonitrile (0.207 g, 0.436 mmol), sodium azide (0.143 g, 2.20 mmol) and ammonium chloride (0.116 g, 2.17 mmol) in DMF (10 mL). The reaction mixture was heated for 3.5 hours, worked-up and purified by HPLC using 90% acetonitrile/0.1% TFA in water. The title compound was obtained as an off-white solid (0.072 g), mp 192–194° C. Mass spectrum (-ESI, [M–H]$^-$) m/z 515. $^1$HNMR (500 MHz, DMSO-d$_6$): δ16.7–17.2 (br s, 1H), 8.35 (d, 1H, J=1.2 Hz), 8.25 (d, 1H, J=9.0 Hz), 8.15 (d, 1H, J-9.0 Hz), 8.05 (dd, 1H, J=8.9 Hz and 1.7 Hz), 7.7–7.75 (m, 2H), 7.6 (d, 1H, J=8.1 Hz), 7.35–7.4 (m, 1H), 7.3–7.35 (m, 1H), 5.75 (s, 2H), 3.0 (t, 2H, J=7.9 Hz), 1.85–1.9 (m, 1H), 1.7–1.8 (m, 4H), 1.55–1.6 (m, 2H), 1.4–1.5 (m, 2H), and 1.15–1.25 ppm (m, 2H). Elemental Analysis for C$_{27}$H$_{25}$BrN$_4$O$_2$: Calculated: C, 62.68; H, 4.87; N, 10.83. Found: C, 62.52; H, 5.02; N, 10.61.

EXAMPLE 13

1-{2-[5-Bromo-6-(1H-1,2,3,4-tetraazol-5-ylmethoxy)-2-naphthyl]-1-benzofuran-3-yl}-2-cyclopentyl-1-ethanone Step 1

1-[2-(5-Bromo-6-hydroxy-2-naphthyl)-1-benzofuran-3-yl]-2-cyclopentyl-1-ethanone

Following the procedure described in Step 4 of Example 1, 6-[3-(2-cyclopentylethyl)-1-benzofuran-2-yl]-2-naphthol (1.28 g, 3.44 mmol) was brominated bromine (0.20 mL, 4.0 mmol) and potassium acetate (3.40 g, 34.6 mmol) in glacial acetic acid (25 mL). Purification by flash chromatography (Biotage apparatus) using 2–3% tert-butyl methyl ether as an eluant yielded 1-[2-(5-bromo-6-hydroxy-2-naphthyl)-1-benzofuran-3-yl]-2-cyclopentyl-1-ethanone as a gold-yellow solid (0.704 g), mp 132–133° C. $^1$HNMR (300 MHz, DMSO-d$_6$): δ10.95 (s, 1H), 8.4 (s, 1H), 8.15 (d, 1H, J=9.5 Hz), 7.9–8.05 (m, 3H), 7.85 (d, 1H, J=8.6 Hz), 7.35–7.5 (m, 3H), 2.8 (d, 2H, J=8.6 Hz), 2.15–2.3 (m, 1H), 1.65–1.8 (m, 2H), 1.3–1.5 (m, 4H), and 0.9–1.05 ppm (m, 2H).

Step 2

2-({1-Bromo-6-[3-(2-cyclopentylacetyl)-1-benzofuran-2-yl]-2-naphthyl}oxy)acetonitrile Following the procedure described in Method B, Step 5 of Example 1, 2-({1-bromo-6-[3-(2-cyclopentylacetyl)-1-benzofuran-2-yl]-2-naphthyl}oxy)acetonitrile was prepared from 1-[2-(5-bromo-6-hydroxy-2-naphthyl)-1-benzofuran-3-yl]-2-cyclopentyl-1-ethanone (0.308 g, 0.685 mmol), cesium carbonate (0.565 g, 1.73 mmol) and bromoacetonitrile (0.12 mL, 1.7 mmol) in acetone (10 mL). Purification by flash chromatography using 7.5–15% tert-butyl methyl ether in hexane and 30–100% ethyl acetate in hexane as eluants yielded a yellow gum (0.186 g). $^1$HNMR (200 MHz, DMSO-d$_6$): δ8.55 (s, 1H), 8.3 (d, 2H, J=8.5 Hz), 7.95–8.15 (m, 2H), 7.6–7.85 (m, 2H), 7.3–7.6 (m, 2H), 5.5 (s, 2H), 2.85 (d, 2H, J=7.7 Hz), 2.1–2.3 (m, 1H), 1.55–1.75 (m, 2H), 1.3–1.5 (m, 4H), and 0.8–1.1 ppm (m, 2H).

Step 3

1-{2-[5-Bromo-6-(1H-1,2,3,4-tetraazol-5-ylmethoxy)-2-naphthyl]-1-benzofuran-3-yl}-2-cyclopentyl-1-ethanone Following the procedure described in Step 6 of Example 1, 1-{2-[5-bromo-6-(1H-1,2,3,4-tetraazol-5-ylmethoxy)-2-naphthyl]-1-benzofuran-3-yl}-2-cyclopentyl-1-ethanone was prepared from 2-({1-bromo-6-[3-(2-cyclopentylacetyl)-1-benzofuran-2-yl]-2-naphthyl}oxy) acetonitrile (0.181 g, 0.371 mmol), sodium azide (0.132 g, 2.03 mmol) and ammonium chloride (0.107 g, 2.00 mmol) in DMF (10 mL). Purification by HPLC using 95% methanol/0.1% TFA in water as the mobile yielded a light yellow solid (0.134 g), mp 186–187° C. Mass spectrum (−ESI, [M−H]−) m/z 529. $^1$HNMR (500 MHz, DMSO-d$_6$): δ16.7–17.2 (br s, 1H), 8.5 (d, 1H, J=1.5 Hz), 8.2–8.25 (m, 2H), 8.0 (d, 2H, J=8.9 Hz), 7.75 (q, 2H, J=8.6 Hz), 7.4–7.5 (m, 2H), 5.75 (s, 2H), 2.8 (d, 2H, J=7.0 Hz), 2.2–2.25 (m, 1H), 1.6–1.65 (m, 2H), 1.35–1.45 (m, 4H), and 0.95–1.0 ppm (m, 2H). Elemental Analysis for C$_{27}$H$_{23}$BrN$_4$O$_3$: Calculated: C, 61.03; H, 4.36; N, 10.54. Found: C, 61.46; H, 4.80; N, 9.81.

EXAMPLE 14

2-{[6-(3-Pentanoyl-1-benzofuran-2-yl)-1-phenyl-2-naphthyl]oxy}acetic acid, sodium salt Step 1

Ethyl 2-{[6-(3-pentanoyl-1-benzofuran-2-yl)-1-phenyl-2-naphthyl]oxy}acetate

Following the procedure described in Step 1 of Example 1, ethyl 2-{[6-(3-pentanoyl-1-benzofuran-2-yl)-1-phenyl-2-naphthyl]oxy}acetate was prepared by coupling of ethyl 2-{[1-bromo-6-(3-pentanoyl-1-benzofuran-2-yl)-2-naphthyl]oxy}acetate (0.534 g, 1.05 mmol), and phenylboronic acid (0.607 g, 4.98 mmol), using [1,1'-bis(diphenylphosphino)ferrocene] dichloropalladium (II) complex with dichloromethane (1:1) (0.203 g, 0.249 mmol) and potassium carbonate (0.300 g, 2.17 mmol) in dioxane (10 mL) and water (1.1 mL). Purification by HPLC using 20% tert-butyl methyl ether in hexane as the mobile phase yielded the title compound as a yellow gum (0.166 g). $^1$HNMR (300 MHz, DMSO-d$_6$): δ8.45 (s, 1H), 8.15 (d, 1H, J=9.0 Hz), 8.05 (d, 1H, J=7.5 Hz), 7.75 (t, 3H, J=6.4 Hz), 7.4–7.6 (m, 9H), 4.95 (s, 2H), 4.15 (q, 2H, J=7.3 Hz), 2.75 (t, 2H, J=7.5 Hz), 1.5–1.6 (m, 2H), 1.1–1.25 (m, 5H), and 0.7 ppm (t, 3H, J=7.5 Hz).

Step 2

2-{[6-(3-Pentanoyl-1-benzofuran-2-yl)-1-phenyl-2-naphthyl]oxy}acetic acid, sodium salt Following the procedure described in Step 4 of Example 6, ethyl 2-{[6-(3-pentanoyl-1-benzofuran-2-yl)-1-phenyl-2-naphthyl]oxy}acetate (0.161 g, 0.318 mmol) was hydrolyzed with potassium hydroxide (0.0693 g, 1.24 mmol) in THF (6 mL) and water (6 mL). 2-{[6-(3-pentanoyl-1-benzofuran-2-yl)-1-phenyl-2-naphthyl]oxy}acetic acid was obtained and was converted to the sodium salt by dissolving (0.103 g, 0.215 mmol) of the acid in methanol (5 mL) and adding 1N sodium hydroxide (0.22 mL, 22 mmol). After standing for 25 minutes, the mixture was solvent evaporated and the residue was rinsed with hexane and dried for 24 hours at 100° C. to give a yellow solid (0.0913 g), mp 272–273° C. (dec.). Mass spectrum (−ESI, [M−H]−) m/z 477. $^1$HNMR (500 MHz, DMSO-d$_6$): δ8.35 (d, 1H, J=1.7 Hz), 8.05 (t, 2H, J=7.6 Hz), 7.65–7.7 (m, 2H), 7.5–7.55 (m, 3H), 7.35–7.45 (m, 6H), 4.25 (s, 2H), 2.75 (t, 2H, J=7.3 Hz), 1.5–1.55 (m, 2H), 1.1–1.2 (m, 2H), and 0.7 ppm (t, 3H, J=7.4 Hz). Elemental Analysis for C$_{31}$H$_{26}$O$_5$Na.0.6H$_2$O: Calculated: C, 72.82; H, 5.16; N, 0.00. Found: C, 72.57; H, 4.92; N, 0.05.

EXAMPLE 15

2-({6-(3-Pentanoyl-1-benzofuran-2-yl)-1-[4-(trifluoromethyl)phenyl]-2-naphthyl}oxy) acetic acid Step 1

Ethyl 2-({6-(3-pentanoyl-1-benzofuran-2-yl)-1-[4-(trifluoromethyl)phenyl]-2-naphthyl} oxy)acetate Following the procedure described in Step 1 of Example 1, ethyl 2-({6-(3-pentanoyl-1-benzofuran-2-yl)-1-[4-(trifluoromethyl)phenyl]-2-naphthyl}oxy)acetate was prepared by coupling of ethyl 2-{[1-bromo-6-(3-pentanoyl-1-benzofuran-2-yl)-2-naphthyl]oxy}acetate (0.448 g, 0.879 mmol), and 4-trifluoromethylbenzene boronic acid (0.883 g, 4.65 mmol), using [1,1'-bis(diphenylphosphino)ferrocene] dichloropalladium (II) complex with dichloromethane (1:1) (0.203 g, 0.249 mmol) and potassium carbonate (0.266 g, 1.92 mmol) in dioxane (12 mL) and water (1.2 mL). The reaction mixture was heated to 70° C. for 16 hours. Purification by HPLC using 30% tert-butyl methyl ether in hexane as the mobile phase yielded a yellow gum (0.241 g). $^1$HNMR (200 MHz, DMSO-d$_6$): δ8.45 (s, 1H), 8.2 (d, 1H, J=9.0 Hz), 7.3–8.1 (m, 11H), 4.95 (s, 2H), 4.1 (q, 2H, J=7.0 Hz), 2.7 (t, 2H, J=7.3 Hz), 1.4–1.65 (m, 2H), 1.0–1.3 (m, 5H), and 0.7 ppm (t, 3H, J=7.0 Hz).

Step 2

2-({6-(3-Pentanoyl-1-benzofuran-2-yl)-1-[4-(trifluoromethyl)phenyl]-2-naphthyl}oxy) acetic acid, sodium salt Following the procedure described in Step 4 of Example 6, 2-({6-(3-pentanoyl-1-benzofuran-2-yl)-1-[4-(trifluoromethyl)phenyl]-2-naphthyl}oxy)acetic acid was prepared by hydrolysis of ethyl 2-({6-(3-pentanoyl-1-benzofuran-2-yl)-1-[4-(trifluoromethyl)phenyl]-2-naphthyl}oxy)acetate (0.234 g, 0.407 mmol) with potassium hydroxide (0.076 g, 1.35 mmol) in THF (5 mL) and water (5 mL). Conversion of the acid to the sodium salt was carried out as described in Step 2 of Example 14. Drying at 100° C. for 24 hours yielded the title compound as a light yellow solid (0.139 g), mp 274–275° C. (dec.). Mass spectrum (−ESI, [M−H]−) m/z 545. $^1$HNMR (500 MHz, DMSO-d$_6$): δ8.4 (s, 1H), 8.05 (d, 1H, J=9.2 Hz), 8.0 (d, 1H, J=8.6 Hz), 7.85 (d, 2H, J=8.1 Hz), 7.75 (t, 4H, J=8.6 Hz), 7.45 (d, 1H, J=9.0 Hz), 7.4–7.5 (m, 3H), 4.25 (s, 2H), 2.7–2.75 (m, 2H), 1.5–1.55 (m, 2H), 1.1–1.2 (m, 2H), and 0.75 ppm (t, 3H, J=7.4 Hz). Elemental Analysis for C$_{32}$H$_{25}$F$_3$O$_5$Na.1.0 H$_2$O: Calculated: C, 65.53; H, 4.47; N, 0.00. Found: C, 65.85; H, 4.20; N, 0.02.

EXAMPLE 16

1-{2-[5-Phenyl-6-(1H1,2,3,4-tetraazol-5-ylmethoxy)-2-naphthyl]-1-benzofuran-3-yl}-1-pentanone Step 1

2-{[6-(3-Pentanoyl-1-benzofuran-2-yl)-1-phenyl-2-naphthyl]oxy}acetonitrile

Following the procedure described in Step 1 of Example 1, 2-{[1-bromo-6-(3-pentanoyl-1-benzofuran-2-yl)-2-naphthyl]oxy}acetonitrile (0.480 g, 1.04 mmol) was coupled to phenylboronic acid (0.448 g, 3.67 mmol) using [1,1'-bis(diphenylphosphino)ferrocene] dichloropalladium (II) complex with dichloromethane (1:1) (0.0918 g, 0.112 mmol) in presence of potassium carbonate (0.290 g, 2.10 mmol) in dioxane (10 mL) and water (1.0 mL). The reaction mixture was stirred at 70° C. for 22 hours. Purification by flash chromatography (Biotage apparatus) using 7.5–10% tert-butyl methyl ether in hexane furnished the title compound (0.230 g). $^1$HNMR (300 MHz, DMSO-d$_6$): δ8.5 (s, 1H), 8.3 (d, 1H, J=9.2 Hz), 8.05 (d, 1H, J=7.7 Hz), 7.7–7.85 (m, 3H), 7.35–7.6 (m, 9H), 5.25 (s, 2H), 2.75 (t, 2H, J=7.7 Hz), 1.5–1.6 (m, 2H), 1.1–1.3 (m, 2H), and 0.75 ppm (t, 3H, J=7.7 Hz).

Step 2

1-{2-[5-Phenyl-6-(1H1,2,3,4-tetraazol-5-ylmethoxy)-2-naphthyl]-1-benzofuran-3-yl}-1-pentanone Following the procedure described in Step 6 of Example 1, 1-{2-[5-phenyl-6-(1H-1,2,3,4-tetraazol-5-ylmethoxy)-2-naphthyl]-1-benzofuran-3-yl}-1-pentanone was prepared from 2-{[6-(3-pentanoyl-1-benzofuran-2-yl)-1-phenyl-2-naphthyl]oxy}acetonitrile (0.224 g, 0.487 mmol), sodium azide (0.162 g, 2.49 mmol) and ammonium chloride (0.140 g, 2.62 mmol) in DMF (10 mL). Purification by HPLC using 90% methanol/0.1% TFA in water as the mobile phase yielded a light yellow solid (0.0825 g), mp 160–164° C. Mass spectrum (–ESI, [M–H]$^-$) m/z 501. $^1$HNMR (500 MHz, DMSO-d$_6$): δ16.5–17.0 (br, 1H), 8.45 (d, 1H, J=1.7 Hz), 8.2 (d, 1H, J=9.0 Hz), 8.0 (dd, 1H, J=7.6 Hz and 0.76 Hz), 7.7–7.75 (m, 3H), 7.4–7.5 (m, 6H), 7.3–7.35 (m, 2H), 5.55 (s, 2H), 2.75 (t, 2H, J=7.3 Hz), 1.5–1.55 (m, 2H), 1.1–1.2 (m, 2H), and 0.7 ppm (t, 3H, J=7.3 Hz). Elemental Analysis for C$_{31}$H$_{26}$N$_4$O$_3$Na.0.10 H$_2$O: Calculated: C, 73.82; H, 5.24; N, 11.11. Found: C, 73.56; H, 5.21; N, 10.95.

EXAMPLE 17

2-({1-Bromo-6-[3-(2-cyclopentylacetyl)-1-benzofuran-2-yl]-2-naphthyl}oxy)acetic acid

Step 1

Ethyl 2-({1-bromo-6-[3-(2-cyclopentylacetyl)-1-benzofuran-2-yl]-2-naphthyl}oxy) acetate Following the procedure described in Method B, Step 5 of Example 1, ethyl 2-({1-bromo-6-[3-(2-cyclopentylacetyl)-1-benzofuran-2-yl]-2-naphthyl}oxy)acetate was prepared from 1-[2-(5-bromo-6-hydroxy-2-naphthyl)-1-benzofuran-3-yl]-2-cyclopentyl-1-ethanone (0.250 g, 0.556 mmol), cesium carbonate (0.461 g, 1.41 mmol) and ethyl bromoacetate (0.15 ml, 1.4 mmol) in acetone (10 mL). The title compound was obtained as a yellow gum (0.246 g). $^1$HNMR (200 MHz, DMSO-d$_6$): δ8.0 (s, 1H), 8.25 (d, 1H, J=9.5 Hz), 8.15 (d, 1H, J=9.5 Hz), 8.0–8.1 (m, 1H), 7.7–7.8 (m, 1H), 7.35–7.6 (m, 4H), 5.15 (s, 2H), 4.15 (q, 2H, J=7.2 Hz), 2.8 (d, 1H, J=7.5 Hz), 2.15–2.3 (m, 1H), 1.5–1.75 (m, 2H), 1.3–1.5 (m, 4H), 1.2 (t, 3H, J=7.3 Hz), and 0.9–1.1 ppm (m, 2H).

Step 2

2-({1-Bromo-6-[3-(2-cyclopentylacetyl)-1-benzofuran-2-yl]-2-naphthyl}oxy)acetic acid Following the procedure described in Step 4 of Example 6, ethyl 2-({1-bromo-6-[3-(2-cyclopentylacetyl)-1-benzofuran-2-yl]-2-naphthyl}oxy)acetate (0.245 g, 0.458 mmol) was hydrolyzed with potassium hydroxide (0.0938 g, 1.67 mmol) in THF (5 mL) and water (5 mL). Purification by HPLC using 85% methanol/0.1% TFA in water as the mobile phase yielded and drying at 80° C. for 15 hours yielded 2-({1-bromo-6-[3-(2-cyclopentylacetyl)-1-benzofuran-2-yl]-2-naphthyl}oxy)acetic as a light yellow solid (0.077 g), mp 150–152° C. Mass spectrum (+ESI, [M+H]$^+$) m/z 509; $^1$HNMR (500 MHz, DMSO-d$_6$): δ13.0–13.5 (br s, 1H), 8.45 (d, 1H, J=1.7 Hz), 8.25 (d, 1H, J=8.9 Hz), 8.15 (d, 1H, J=9.2 Hz), 7.95–8.0 (m, 2H), 7.75 (d, 1H, J=7.9 Hz), 7.5 (d, 1H, J=9.2 Hz), 7.4–7.45 (m, 2H), 5.05 (s, 2H), 2.8 (d, 2H, J=7.0 Hz), 2.2–2.25 (m, 1H), 1.6–1.65 (m, 2H), 1.35–1.45 (m, 4H), and 0.95–1.05 ppm (m, 2H). Elemental Analysis for C$_{27}$H$_{23}$BrO$_5$: Calculated: C, 63.92; H, 4.57; N, 0.00. Found: C, 63.78; H, 4.72; N, 0.01.

EXAMPLE 18

1-(2-{6-(1H-1,2,3,4-Tetraazol-5-ylmethoxy)-5-[4-(trifluoromethyl)phenyl]-2-naphthyl}-1-benzofuran-3-yl)-1-pentanone

Step 1

2-({6-(3-Pentanoyl-1-benzofuran-2-yl)-1-[4-(trifluoromethyl)phenyl]-2-naphthyl}oxy) acetonitrile Following the procedure described in Step 1 of Example 1, 2-{[1-bromo-6-(3-pentanoyl-1-benzofuran-2-yl)-2-naphthyl]oxy}acetonitrile (0.476 g, 1.03 mmol) was coupled to 4-trifluoromethylphenylboronic acid (0.785 g, 4.13 mmol), using [1,1'-bis(diphenylphosphino)ferrocene] dichloropalladium (II) complex with dichloromethane (1:1) (0.088 g, 0.108 mmol) and potassium carbonate (0.301 g, 2.18 mmol) in dioxane (10 mL) and water (1 mL). The reaction mixture was heated at 77° C. for 16 hours. Purification by flash chromatography (Biotage apparatus) using 2–10% ethyl acetate in hexane as an eluant yielded 2-({6-(3-pentanoyl-1-benzofuran-2-yl)-1-[4-(trifluoromethyl)phenyl]-2-naphthyl}oxy)acetonitrile as a yellow wax (0.364 g); $^1$HNMR (300 MHz, DMSO-d$_6$): δ8.55 (s, 1H), 8.35 (d, 1H, J=8.5 Hz), 8.05 (d, 1H, J=7.7 Hz), 7.95 (d, 2H, J=7.7 Hz), 7.75–7.85 (m, 2H), 7.75 (d, 1H, J=7.7 Hz), 7.35–7.5 (m, 3H), 5.3 (s, 2H), 2.75 (t, 2H, J=7.7 Hz), 1.5–1.6 (m, 2H), 1.1–1.25 (m, 2H), and 0.7 (t, 3H, J=7.7 Hz).

Step 2

1-(2-{6-(1H1,2,3,4-Tetraazol-5-ylmethoxy)-5-[4-(trifluoromethyl)phenyl]-2-naphthyl}-1-benzofuran-3-yl)-1-pentanone Following the procedure described in Step 6 of Example 1, 1-(2-{6-(1H-1,2,3,4-tetraazol-5-ylmethoxy)-5-[4-(trifluoromethyl)phenyl]-2-naphthyl}-1-benzofuran-3-yl)-1-pentanone was prepared from 2-({6-(3-pentanoyl-1-benzofuran-2-yl)-1-[4-(trifluoromethyl)phenyl]-2-naphthyl}oxy)acetonitrile (0.351 g, 0.665 mmol), sodium azide (0.227 g, 3.49 mmol), and ammonium chloride (0.186 g, 3.48 mmol) in DMF (10 mL). Purification by HPLC using 85% methanol/0.1% TFA in water as the mobile phase and drying at 80° C. for 15 hours furnished the title compound as a light yellow solid (0.147 g), mp 189–191° C. Mass spectrum (–ESI, [M–H]$^-$) m/z 569; $^1$HNMR (500 MHz, DMSO-d$_6$): δ16.5–17.0 (br s, 1H), 8.5 (d, 1H, J=1.7 Hz), 8.25 (d, 1H, J=9.2 Hz), 8.0 (d, 1H, J=8.4 Hz), 7.85 (d, 2H, J=8.1 Hz), 7.75–7.8 (m, 2H), 7.75 (d, 1H, J=7.8 Hz), 7.6 (d, 2H, J=8.0 Hz), 7.4–7.45 (m, 3H), 5.65 (s, 2H), 2.75 (t, 2H, J=7.3 Hz), 1.5–1.6 Hz (m, 2H), 1.1–1.2 (m, 2H), and 0.75 ppm (t, 3H, J=7.3 Hz). Elemental Analysis for C$_{32}$H$_{25}$F$_3$N$_4$O$_5$.0.10H$_2$: Calculated: C, 67.15; H, 4.44; N, 9.79. Found: C, 66.81; H, 4.39; N, 9.48.

EXAMPLE 19

2-{[1-Bromo-6-(3-pentanoyl-1-benzofuran-2-yl)-2-naphthyl]oxy}-3-phenylpropanoic acid

Step 1

Ethyl 2-{[1-bromo-6-(3-pentanoyl-1-benzofuran-2-yl)-2-naphthyl]oxy}-3-phenyl propanoate Following the procedure described in Step 2 of Example 4, 1-[2-(5-bromo-6-hydroxy-2-naphthyl)-1-benzofuran-3- yl]-1-pentanone (2.38 g, 5.62 mmol) was coupled to ethyl 2-hydroxy-3-phenylpropanoate (1.65 g, 8.50 mmol) in presence of triphenylphosphine (2.23 g, 8.50 mmol) and diisopropylazodicarboxylate (1.7 mL, 8.5 mmol) in benzene (62 mL). Purification by HPLC, using 95% acetonitrile in water as the mobile phase, yielded ethyl 2-{[1-bromo-6-(3-pentanoyl-1-benzofuran-2-yl)-2-naphthyl]oxy}-3-phenylpropanoate as a yellow gum (1.86 g). $^1$HNMR (300 MHz, DMSO-$d_6$): δ8.45 (s, 1H), 8.25 (d, 1H, J=7.7 Hz), 8.1 (d, 1H, J=7.7 Hz), 7.95–8.1 (m, 2H), 7.85 (d, 1H, J=7.7 Hz), 7.4–7.5 (m, 5H), 7.2–7.4 (m, 3H), 5.5 (t, 1H, J=6.0 Hz), 4.1 (q, 2H, J=7.0 Hz), 2.75 (t, 2H, J=7.0 Hz), 1.45–1.6 (m, 2H), 1.05–1.25 (m, 6H), and 0.7 ppm (t, 3H, J=7.0 Hz).

Step 2

2-{[1-Bromo-6-(3-pentanoyl-1-benzofuran-2-yl)-2-naphthyl]oxy}-3-phenylpropanoic acid Following the procedure described in Step 4 of Example 6, ethyl 2-{[1-bromo-6-(3-pentanoyl-1-benzofuran-2-yl)-2-naphthyl]oxy}-3-phenylpropanoate (1.85 g, 3.09 mmol) was hydrolyzed with potassium hydroxide (0.523 g, 9.32 mmol) in THF (20 mL) and water (20 mL). Crystallization from methylene chloride/hexane and drying at 78° C for 12 hours yielded 2-{[1-bromo-6-(3-pentanoyl-1-benzofuran-2-yl)-2-naphthyl]oxy}-3-phenylpropanoic acid a bright yellow solid (1.35 g), mp 115–117° C. Mass spectrum (+ESI, [M+H]$^+$) m/z 573; $^1$HNMR (500 MHz, DMSO-$d_6$): δ13.2–13.5 (br s, 1H), 8.45 (d, 1H, J=1.5 Hz), 8.2 (d, 1H, J=8.9 Hz), 8.1 (d, 1H, J=9.2 Hz), 8.05 (dd, 1H, J=7.7 Hz and 0.7 Hz), 8.0 (dd, 1H, J=8.9 Hz and 1.7 Hz), 7.75 (d, 1H, J=7.8 Hz), 7.4–7.45 (m, 6H), 7.3 (t, 2H, J=7.6 Hz), 7.25 (t, 1H, J=7.4 Hz), 5.35–5.4 (m, 1H), 2.75 (t, 2H, J=7.3 Hz), 1.5–1.6 (m, 2H), 1.1–1.2 (m, 2H), and 0.7 ppm (t, 3H, J=7.4 Hz). Elemental Analysis for $C_{32}H_{27}BrO_5 \cdot 0.10H_2O$: Calculated: C, 67.05; H, 4.78; N, 0.00. Found: C, 66.69; H, 4.38; N, 0.02.

EXAMPLE 20

1-{2-[5-Methyl-6-(1H-1,2,3,4-tetraazol-5-ylmethoxy)-2-naphthyl]-1-benzofuran-3-yl}-1-pentanone Step 1

6-Bromo-1-[(dimethylamino)methyl]-2-naphthol

The mixture of 6-bromo-2-naphthol (124 g, 0.556 mol) dimethyl amine (175 mL Of 40% solution in water, 1.56 mol), formaldehyde (83.5 mL of 40% solution in water, 1.11 mol) and ethanol (700 mL) was stirred at room temperature for 2 hours then filtered. The solids were washed with fresh ethanol and air dried to give the title compound as a solid (120 g), mp 95–96° C. Mass spectrum (+ESI, [M+H]$^+$) m/z 280, 282. $^1$HNMR (500 MHz, DMSO-$d_6$): δ8.02 (d, 1H, J=2.0 Hz), 7.90 (d, 1H, J=9.2 Hz), 7.69 (d, 1H, J=9.0 Hz), 7.51 (dd, 1H, J=9.2, 2.2 Hz), 7.10 (d, 1H, J=9.2 Hz), 3.94 (s, 2H), and 2.26 ppm (s, 6H). Elemental Analysis for $C_{13}H_{14}BrNO$: Calculated: C, 55.73; H, 5.04; N, 5.00. Found: C, 55.83; H, 5.04; N, 4.96.

Step 2

6-Bromo-1-[(dimethylamino)methyl]-2-naphthyl acetate hydrochloride

6-Bromo-1-[(dimethylamino)methyl]-2-naphthol (5.6 g, 0.02 mol) was stirred in methylene chloride (120 mL). Acetyl chloride (3.0 mL, 0.042 mol) was added. The mixture was stirred at room temperature for 1 hour and the solvent was concentrated.

The precipitated solid was collected by filtration, washed with ether and dried to give the title compound (6.8 g) as a white solid, mp 190–192° C. Mass spectrum (+ES, [M+H]$^+$) m/z 322, 324. $^1$HNMR (500 MHz, DMSO-$d_6$): δ9.68 (br s, 1H), 8.36 (s, 1H), 8.29 (d, 1H, J=9.2 Hz), 8.12 (d, 1H, J=9.0 Hz), 7.82 (d, 1H, J=8.8 Hz), 7.56 (d, 1H, J=9.0 Hz), 4.74 (d, 2H, J=5.5 Hz), 2.83 (d, 6H, J=4.6 Hz), and 2.44 ppm (s, 3H). Elemental Analysis for $C_{15}H_{16}BrNO_2 \cdot HCl$: Calculated: C, 50.23; H, 4.78; N, 3.91. Found: C, 50.16; H, 4.64; N, 3.77.

Step 3

6-Bromo-1-methyl-2-naphthol

6-Bromo-1-[(dimethylamino)methyl]-2-naphthyl acetate hydrochloride (6.4 g, 0.0179 mol) was stirred in ethanol (250 mL). Sodium borohydride (3.0 g, 0.078 mol) was added portion-wise. The mixture was heated at reflux for 2 hours, then cooled to room temperature and water (100 mL) was added. The mixture was stirred for ½ hour then acidified with 2N hydrochloric acid. The ethanol was evaporated and the mixture was extracted with ethyl acetate. The extracts were washed with 2N hydrochloric acid, then with water, dried over anhydrous magnesium sulfate and solvent evaporated to give the title compound as a solid, mp 127–129° C. $^1$HNMR (500 MHz, DMSO-$d_6$): δ9.66 (s, 1H), 8.01 (s, 1H), 7.80 (d, 1H, J=9.2 Hz), 7.60 (d, 1H, J=8.7 Hz), 7.53 (d, 1H, J=9.0 Hz), 7.19 (d, 1H, J=8.9 Hz), 2.80 (s, 6H), and 2.39 ppm (s, 3H). Elemental Analysis for $C_{11}H_9BrO$: Calculated: C, 55.72; H, 3.83; N, 0.00. Found: C, 55.81; H, 3.82; N, 0.00.

Step 4

2-[(6-Bromo-1-methyl-2-naphthyl)oxy]acetonitrile

Following the procedure described in Method B, Step 5 of Example 1, 2-[(6-Bromo-1-methyl-2-naphthyl)oxy] acetonitrile was prepared from 6-bromo-1-methyl-2-naphthol (6.3 g, 27 mmol), cesium carbonate (18.2 g, 56 mmol) and bromoacetonitrile (2.0 mL, 29 mmol) in acetone (55 mL). The reaction mixture was stirred for 4 hours. The compound was purified by flash chromatography using 5–40% isopropyl ether in hexane as an eluant. The title compound was obtained as an orange-yellow waxy solid ((4.94 g); $^1$HNMR (300 MHz, DMSO-$d_6$): δ8.2 (s, 1H), 7.95 (d, 1H, J=8.5 Hz), 7.9 (d, 1H, J=8.5 Hz), 7.65 (d, 1H, J=9.2 Hz), 7.55 (d, 1H, J=8.5 Hz), 5.3 (s, 2H), and 2.5 ppm (s, 3H).

Step 5

2-{[6-(1-Benzofuran-2-yl)-1-methyl-2-naphthyl]oxy}acetonitrile

Following the procedure described in Step 1 of Example 1, 2-[(6-bromo-1-methyl-2-naphthyl)oxy]acetonitrile (4.93 g, 17.9 mmol) was coupled to 2-benzofuranboronic acid (3.58 g, 22.1 mmol) using [1,1'-bis(diphenylphosphino) ferrocene]dichloropalladium (II) complex with dichloromethane (1:1) (0.452 g, 0.553 mmol) and potassium carbonate (3.75 g, 27.1 mmol) in dioxane (130 mL) and water (13 mL). Purification by flash chromatography using 3–9% ethyl acetate in hexane as an eluant yielded 2-{[6-(1-benzofuran-2-yl)-1-methyl-2-naphthyl]oxy}acetonitrile a light yellow solid (3.03 g), mp 143–145° C., $^1$HNMR (300 MHz, DMSO-$d_6$): δ8.45 (s, 1H), 7.95–8.15 (m, 3H), 7.7 (t, 2H, J=7.3 Hz), 7.5–7.6 (m, 2H), 7.2–7.4 (m, 2H), 5.35 (s, 2H), and 2.55 ppm (s, 3H).

37

Step 6

2-{[1-Methyl-6-(3-pentanoyl-1-benzofuran-2-yl)-2-naphthyl]oxy}acetonitrile

Following the procedure described in Step 2 of Example 1, 2-{[6-(1-benzofuran-2-yl)-1-methyl-2-naphthyl]oxy}acetonitrile (1.15 g, 3.67 mmol) was acylated with valeryl chloride (0.52 mL, 4.4 mmol), in presence of tin (IV) chloride (0.52 mL, 4.4 mmol) in methylene chloride (15 mL). 2-{[1-methyl-6-(3-pentanoyl-1-benzofuran-2-yl)-2-naphthyl]oxy}acetonitrile was prepared. Purification by flash chromatography (Biotage apparatus) using 10–20% chloroform in hexane and 100% hexane and 0.5–5% ethyl acetate in hexane as eluants yielded the title compound as a yellow gum (0.458 g). $^1$HNMR (300 MHz, DMSO-$d_6$): δ8.45 (s, 1H), 8.2 (d, 1H, J=7.7 Hz), 8.05 (t, 2H, J=8.8 Hz), 7.95 (d, 1H, J=7.7 Hz), 7.75 (d, 1H, J=7.7 Hz), 8.65 (d, 1H, J=7.7 Hz), 7.4–7.5 (m, 2H), 5.35 (s, 2H), 2.75 (t, 2H, J=8.1 Hz), 2.55 (s, 3H), 1.5–1.6 (m, 2H), 1.1–1.25 (m, 2H), and 0.7 ppm (t, 3H, J=8.8 Hz).

Step 7

1-{2-[5-Methyl-6-(1H1,2,3,4-tetraazol-5-ylmethoxy)-2-naphthyl]-1-benzofuran-3-yl}-1-pentanone Following the procedure described in Step 6 of Example 1, 1-{2-[5-methyl-6-(1H-1,2,3,4-tetraazol-5-ylmethoxy)-2-naphthyl]-1-benzofuran-3-yl}-1-pentanone was prepared from 2-{[1-methyl-6-(3-pentanoyl-1-benzofuran-2-yl)-2-naphthyl]oxy}acetonitrile (0.454 g, 1.14 mmol), sodium azide (0.375 g, 5.77 mmol) and ammonium chloride (0.305 g, 5.70 mmol) in DMF (10 mL). The compound was purified by HPLC using 75% acetonitrile in water as the mobile phase. Drying for 13 hours at 90° C. yielded a light beige solid (0.160 g), mp 162–164° C. Mass spectrum (+ESI, [M+H]$^+$) m/z 441; $^1$HNMR (500 MHz, DMSO-$d_6$): δ8.4 (d, 1H, J=1.7 Hz), 8.15 (d, 1H, J=9.0 Hz), 8.0–8.05 (m, 2H), 7.9 (dd, 1H, J=8.9 Hz and 1.8 Hz), 7.75 (d, 1H, J=7.6 Hz), 7.65 (d, 1H, J=9.0 Hz), 7.4–7.45 (m, 2H), 5.65 (s, 2H), 2.75 (t, 2H, J=7.3 Hz), 2.55 (s, 3H), 1.5–1.6 (m, 2H), 1.1–1.2 (m, 2H), and 0.7 ppm (t, 3H, J=7.3 Hz). Elemental Analysis for $C_{26}H_{24}N_4O_5$: Calculated: C, 70.89; H, 5.49; N, 12.72. Found: C, 70.55; H, 5.48; N, 12.68.

EXAMPLE 21

5-({[1-Methyl-6-(3-pentyl-1-benzofuran-2-yl)-2-naphthyl]oxy}methyl)-1H-1,2,3,4-tetraazole

Step 1

2-({6-[3-(1-Hydroxypentyl)-1-benzofuran-2-yl]-1-methyl-2-naphthyl}oxy)acetonitrile Following the procedure described in Step 1 of Example 11, 2-{[1-methyl-6-(3-pentanoyl-1-benzofuran-2-yl)-2-naphthyl]oxy}acetonitrile (0.874 g, 2.20 mmol) was reduced with sodium borohydride (0.495 g, 13.1 mmol) in ethanol (25 mL). 2-({6-[3-(1-hydroxypentyl)-1-benzofuran-2-yl]-1-methyl-2-naphthyl}oxy)acetonitrile was obtained as a yellow gum (0.838 g,). $^1$HNMR (300 MHz, DMSO-$d_6$): δ8.3 (s, 1H), 8.15 (d, 1H, J=9.2 Hz), 8.0 (t, 1H, J=8.5 Hz), 7.9 (t, 1H, J=7.7 Hz), 7.55 (q, 3H, J=8.2 Hz), 7.25–7.35 (br, 1H), 5.45 (d, 1H, J=5.4 Hz), 5.35 (s, 2H), 5.1–5.2 (br, 1H), 2.55 (s, 3H), 1.8–2.0 (br, 2H), 1.2–1.3 (br, 2H), 1.35 (t, 2H, J=7.3 Hz), and 0.8 ppm (t, 3H, J=7.3 Hz).

38

Step 2

2-{[1-Methyl-6-(3-pentyl-1-benzofuran-2-yl)-2-naphthyl]oxy}acetonitrile

Following the procedure described in Step 2 of Example 11, 2-{[1-methyl-6-(3-pentyl-1-benzofuran-2-yl)-2-naphthyl]oxy}acetonitrile was prepared from 2-({6-[3-(1-hydroxypentyl)-1-benzofuran-2-yl]-1-methyl-2-naphthyl}oxy)acetonitrile (0.838 g, 2.10 mmol), triethylsilane (0.67 mL, 4.2 mmol) and trifluoroacetic acid (1.7 mL, 22 mmol) in methylene chloride (20 mL). Purification by flash chromatography using 100% hexane and 1–2% ethyl acetate in hexane as an eluants furnished the title compound as a yellow gum (0.416 g). $^1$HNMR (300 MHz, DMSO-$d_6$): δ8.35 (s, 1H), 8.15 (d, 1H, J=8.5 Hz), 8.05 (d, 1H, J=8.5 Hz), 7.95 (d, 1H, J=8.5 Hz), 7.7 (d, 1H, J=6.9 Hz), 7.65 (d, 1H, J=7.7 Hz), 7.55 (d, 1H, J=9.2 Hz), 7.25–7.4 (m, 2H), 5.35 (s, 2H), 3.0 (t, 2H, J=7.7 Hz), 2.55 (s, 3H), 1.65–1.8 (m, 2H), 1.3–1.45 (m, 4H), and 0.85 ppm (t, 3H, J=7.7 Hz).

Step 3

5-({[1-Methyl-6-(3-pentyl-1-benzofuran-2-yl)-2-naphthyl]oxy}methyl)-1H1,2,3,4-tetraazole Following the procedure described in Step 6 of Example 1, 5-({[1-methyl-6-(3-pentyl-1-benzofuran-2-yl)-2-naphthyl]oxy}methyl)-1H-1,2,3,4-tetraazole was prepared from 2-{[1-methyl-6-(3-pentyl-1-benzofuran-2-yl)-2-naphthyl]oxy}acetonitrile (0.410 g, 1.07 mmol), sodium azide (0.346 g, 5.32 mmol) and ammonium chloride (0.284 g, 5.31 mmol) in DMF (10 mL). Crystallization from acetonitrile and drying for 16 hours at 76° C. yielded the title compound as a light yellow solid (0.252 g), mp 169–171° C. (dec.). Mass spectrum (–ESI, [M–H]$^-$) m/z 425. $^1$HNMR (500 MHz, DMSO-$d_6$): δ16.8 (br s, 1H), 8.3 (d, 1H, J=1.5 Hz), 8.15 (d, 1H, J=9.0 Hz), 7.95 (d, 1H, J=9.0 Hz), 7.9 (dd, 1H, J=9.0 Hz and 1.8 Hz), 7.7 (d, 1H, J=7.6 Hz), 7.6 (q, 2H, J=7.0 Hz), 7.25–7.35 (m, 2H), 5.65 (s, 2H), 3.0 (t, 2H, J=7.6 Hz), 2.55 (s, 3H), 1.7–1.8 (m, 2H), 1.3–1.45 (m, 4H), and 0.85 ppm (t, 3H, J=7.2 Hz). Elemental Analysis for $C_{26}H_{26}N_4O_2$0.15 $H_2$: Calculated: C, 72.76; H, 6.18; N, 13.05. Found: C, 72.45; H, 5.82; N, 13.15.

EXAMPLE 22

2-{[1-Methyl-6-(3-pentanoyl-1-benzofuran-2-yl)-2-naphthyl]oxy}acetic acid

A mixture of 2-{[1-methyl-6-(3-pentanoyl-1-benzofuran-2-yl)-2-aphthyl]oxy}acetonitrile (0.301 g, 0.757 mmol) and sodium hydroxide (1.12 g, 28.0 mmol) in ethanol (8 mL) was refluxed for 3 hours. The mixture was allowed to cool to room temperature, poured into excess water, then acidified with 2N hydrochloric acid and extracted with ethyl acetate. The organic phase was washed with water and brine, dried over magnesium sulfate, filtered and concentrated. The residue was purified by HPLC using 75% acetonitrile/0.1% TFA in water. Treatment with hexane afforded 2-{[1-methyl-6-(3-pentanoyl-1-benzofuran-2-yl)-2-naphthyl]oxy}acetic acid as a light beige solid (0.0332 g), mp 153–155° C. Mass spectrum (+ESI, [M+H]$^+$) m/z 417. $^1$HNMR (500 MHz, DMSO-$d_6$): δ12.9–13.2 (br s, 1H), 8.35 (d, 1H, J=1.5 Hz), 8.15 (d, 1H, J=8.9 Hz), 8.05 (d, 1H, J=8.5 Hz), 7.95 (d, 1H, J=9.2 Hz), 7.85 (dd, 1H, J=8.9 Hz and 1.8 Hz), 7.75 (d, 1H, J=8.1 Hz), 7.45–7.45 (m, 3H), 4.9 (s, 2H), 2.75 (t, 2H, J=7.3 Hz), 2.55 (s, 3H), 1.5–1.6 (m, 2H), 1.1–1.2 (m, 2H), and 0.75 ppm (t, 3H, J=7.3 Hz). Elemental Analysis for C$_{26}$H$_{24}$O$_5$.0.15 H$_2$O: Calculated: C, 74.50; H, 5.84; N, 0.00. Found: C, 74.13; H, 5.77; N, 0.02.

EXAMPLE 23

2-{[1-Methyl-6-(3-pentanoyl-1-benzofuran-2-yl)-2-naphthyl]oxy}-3-phenylpropanoic acid Step 1

Ethyl 2-[(6-bromo-1-methyl-2-naphthyl)oxy]-3-phenylpropanoate

Following the procedure described in Step 2 of Example 4, 6-bromo-1-methyl-2-naphthol (2.44 g 10.3 mmol) was coupled to ethyl 2-hydroxy-3-phenylpropanoate (3.0 g, 15 mmol) in presence of triphenylphosphine (4.17 g, 15.9 mmol) and diisopropyl azodicarboxylate (3.0 mL, 15 mmol) in benzene (65 mL). Purification by flash chromatography using 100% hexane and 1–4% ethyl acetate in hexane as eluants afforded ethyl 2-[(6-bromo-1-methyl-2-naphthyl)oxy]-3-phenylpropanoate as a transparent yellow gum (1.86 g). $^1$HNMR (400 MHz, DMSO-d$_6$): δ8.1 (s, 1H), 7.9 (d, 1H, J=7.0 Hz), 7.7 (d, 1H, J=7.0 Hz), 7.6 (d, 1H, J=6.3 Hz), 7.3–7.4 (m, 4 H), 7.2–7.3 (m, 2H), 5.25 (t, 1H, J=6.3 Hz), 4.1 (q, 2H, J=7.0 Hz), 3.25–3.35 (m, 2H), 2.45 (s, 3H), and 1.1 ppm (t, 3H, J=7.0 Hz).

Step 2

Ethyl 2-{([6-(1-benzofuran-2-yl)-1-methyl-2-naphthyl]oxy}-3-phenylpropanoate

Following the procedure described in Step 1 of Example 1, ethyl 2-{[6-(1-benzofuran-2-yl)-1-methyl-2-naphthyl]oxy}-3-phenylpropanoate was prepared by coupling of ethyl 2-[(6-bromo-1-methyl-2-naphthyl)oxy]-3-phenylpropanoate (1.86 g, 4.50 mmol) and 2-benzofuranboronic acid (0.883 g, 5.45 mmol), in presence of [1,1'-bis(diphenylphosphino) ferrocene] dichloropalladium (II) complex with dichloromethane (1:1) (0.160 g, 0.196 mmol) and potassium carbonate (1.22 g, 8.83 mmol) in dioxane (45 mL) and water (4.5 mL). Purification by flash chromatography using 100% hexane and 0.5–2% ethyl acetate in hexane as eluants furnished the title compound as a light yellow solid (0.995 g), mp 125–127° C. Mass spectrum (+ESI, [M+H]$^+$) m/z 451; $^1$HNMR (500 MHz, DMSO-d$_6$): δ8.35 (s, 1H), 8.05 (s, 2H), 7.85 (d, 1H, J=9.2 Hz), 7.65–7.7 (m, 2H), 7.5 (s, 1H), 7.2–7.35 (m, 8H), 5.25–5.3 (m, 1H), 4.1 (q, 2H, J=7.1 Hz), 3.2–3.3 (m, 2H), 2.45 (s, 3H), and 1.1 ppm (t, 3H, J=7.1 Hz).

Step 3

Ethyl 2-{[1-methyl-6-(3-pentanoyl-1-benzofuran-2-yl)-2-naphthyl]oxy}-3-phenyl propanoate To a mixture of ethyl 2-{[6-(1-benzofuran-2-yl)-1-methyl-2-naphthyl]oxy}-3-phenylpropanoate (0.944 g, 2.10 mmol) in methylene chloride (4.2 mL) at −78° C. was added valeryl chloride (0.25 mL, 2.1 mmol), and tin (IV) chloride (0.25 mL, 2.1 mmol). The reaction mixture was stirred for 2 hours and 20 minutes. It was diluted with extra methylene chloride and poured into excess sodium bicarbonate solution. The organic phase was washed with water and brine, dried over anhydrous magnesium sulfate, filtered and concentrated. The compound was purified by flash chromatography using 100% hexane and 0.5–3% ethyl acetate in hexane. It was dried at 60° C. for 30 minutes to afford ethyl 2-{[1-methyl-6-(3-pentanoyl-1-benzofuran-2-yl)-2-naphthyl]oxy}-3-phenylpropanoate as a yellow gum (0.553 g). Mass spectrum (+ESI, [M+H]$^+$) m/z 535 $^1$HNMR (500 MHz, DMSO-d$_6$): δ8.35 (d, 1H, J=1.7 Hz), 8.1 (d, 1H, J=9.0 Hz), 8.05 (dd, 1H, J=7.6 Hz and 1.0 Hz), 7.9 (d, 1H, J=9.2 Hz), 7.85 (dd, 1H, J=8.9 Hz and 1.8 Hz), 7.75 (d, 1H, J=8.1 Hz), 7.25–7.45 (m, 8H), 5.3–5.35 (m, 1H), 4.1 (q, 2H, J=6.9 Hz), 3.25–3.35 (m, 2H), 2.75 (t, 2H, J=7.3 Hz), 2.5 (s, 3H), 1.5–1.6 (m, 2H), 1.05–1.2 (m, 5H), and 0.7 ppm (t, 3H, J=7.4 Hz). Elemental Analysis for C$_{35}$H$_{34}$O$_5$: Calculated: C, 78.63; H, 6.41; N, 0.00. Found: C, 78.70; H, 6.30; N, 0.00.

Step 4

2-{[1-Methyl-6-(3-pentanoyl-1-benzofuran-2-yl)-2-naphthyl]oxy}-3-phenylpropanoic acid, sodium salt Following the procedure described in Step 4 of Example 6, ethyl 2-{[1-methyl-6-(3-pentanoyl-1-benzofuran-2-yl)-2-naphthyl]oxy}-3-phenylpropanoate (0.495 g, 0.926 mmol) was hydrolyzed with potassium hydroxide (0.153 g, 2.73 mmol) in THF (7.5 mL) and water (7.5 mL) to afford 2-{[1-methyl-6-(3-pentanoyl-1-benzofuran-2-yl)-2-naphthyl]oxy}-3-phenylpropanoic acid. Conversion to the sodium salt by treating with 1N sodium hydroxide (0.72 mL, 0.72 mmol) in methanol (12 mL) furnished the title compound as a cream-colored solid (0.228 g), mp 221–222° C. Mass spectrum (+ESI, [M+H]$^+$) m/z 507. $^1$HNMR (500 MHz, DMSO-d$_6$): δ8.25 (d, 1H, J=1.7 Hz), 8.0–8.05 (m, 2H), 7.75–7.8 (m, 2H), 7.7 (dd, 1H, J=7.3 Hz and 0.8 Hz), 7.35–7.45 (m, 4H), 7.15 (t, 1H, J=7.3 Hz), 4.45 (dd, 1H, J=9.8 Hz and 3.1 Hz), 3.25 (dd, 1H, J=13.9 Hz and 2.7 Hz), 3.05 (q, 1H, J=7.9 Hz), 2.7 (t, 2H, J=7.3 Hz), 2.4 (s, 3H), 1.5–1.55 (m, 2H), 1.1–1.15 (m, 2H), and 0.7 ppm (t, 3H, J=7.4 Hz). Elemental Analysis for C$_{33}$H$_{30}$O$_5$Na: Calculated: C, 74.99; H, 5.53; N, 0.00. Found: C, 74.63; H, 5.38; N, 0.08.

EXAMPLE 24

2-{[1-Chloro-6-(3-pentanoyl-1-benzofuran-2-yl)-2-naphthyl]oxy}acetic acid

Step 1

6-Bromo-1-chloro-2-naphthol

The solution of 6-bromo-2-naphthol (10.0 g, 0.045 mol) in chloroform (100 mL) was added sulfuryl chloride (6.4 mL, 0.09 mol). The mixture was stirred at reflux for 0.5 hour then at room temperature for 2 hours. Water (50 mL) was added and the organic phase was washed with water then solvent evaporated. The solid was crystallized from hexane and air dried to give the title compound as a solid, mp 103–105° C. Mass spectrum (−ES, [M−H]$^-$) m/z 255, 257, 259. $^1$HNMR (500 MHz, DMSO-d$_6$): δ10.63 (s, 1H), 8.15 (d, 1H, J=1.8 Hz), 7.95 (d, 1H, J=9.0 Hz), 7.7 (d, 1H, J=9 Hz), 7.68 (dd, 1H, J=9.0, 1.8 Hz), and 7.32 ppm (d, 1H, J=8.85 Hz). Elemental Analysis for C$_{10}$H$_6$BrClO: Calculated: C, 46.64; H, 2.35; N, 0.00. Found: C, 46.69; H, 2.35; N, 0.00.

Step 2

Ethyl 2-[(6-bromo-1-chloro-2-naphthyl)oxy]acetate

Following the procedure described in Method B, Step 5 of Example 1, ethyl 2-[(6-bromo-1-chloro-2-naphthyl)oxy] acetate was prepared from 6-bromo-1-chloro-2-naphthol (4.1 g, 16 mmol), cesium carbonate (10.4 g, 31.8 mmol) and ethyl bromoacetate (3.5 mL, 32 mmol) in acetone (45 mL). Purification by flash chromatography using 100% hexane and 1–3% acetone in hexane as eluants yielded the title compound as a cream-colored solid (3.90 g), mp 92–94° C. Mass spectrum (+ESI, [M+H]$^+$) m/z 345; $^1$HNMR (500 MHz, DMSO-d$_6$): δ8.25 (d, 1H, J=2.0 Hz), 8.05 (d, 1H, J=9.0 Hz), 7.95 (d, 1H, J=9.2 Hz), 7.75 (dd, 1H, J=9.1 Hz and 2.1 Hz), 7.5 (d, 1H, J=9.2 Hz), 5.05 (s, 2H), 4.15 (q, 2H, J=7.1 Hz), and 1.2 ppm (t, 3, J=7.1 Hz).

Step 3

Ethyl 2-{[6-(1-benzofuran-2-yl)-1-chloro-2-naphthyl]oxy}acetate

Following the procedure described in Step 1 of Example 1, ethyl 2-[(6-bromo-1-chloro-2-naphthyl)oxy]acetate (3.79 g, 11.0 mmol) and 2-benzofuranboronic acid (2.14 g, 13.2 mmol) were coupled in the presence of [1,1'-bis(diphenylphosphino)ferrocene] dichloropalladium (II) complex with dichloromethane (1:1) (0.534 g, 0.654 mmol) and potassium carbonate (3.07 g, 22.2 mmol) in dioxane (110 mL) and water (11 mL). Purification by flash chromatography using 2–5% ethyl acetate in hexane as an eluant furnished ethyl 2-{[6-(1-benzofuran-2-yl)-1-chloro-2-naphthyl]oxy}acetate as a cream-colored solid (1.91 g), mp 140–142° C. $^1$HNMR (300 MHz, DMSO-d$_6$): δ8.5 (s, 1H), 8.2 (s, 2H), 8.1 (d, 1H, J=8.3 Hz), 7.75–7.85 (m, 2H), 7.7 (s, 1H), 7.5 (d, 1H, J=8.3 Hz), 7.25–7.4 (m. 2H), 5.1 (s, 2H), 4.2 (q, 2H, J=7.5 Hz), and 1.25 ppm (t, 2H, J=7.5 Hz).

Step 4

Ethyl 2-{[1-chloro-6-(3-pentanoyl-1-benzofuran-2-yl)-2-naphthyl]oxy}acetate

Following the procedure described in Step 3 of Example 23, ethyl 2-{[6-(1-benzofuran-2-yl)-1-chloro-2-naphthyl]oxy}acetate (1.90 g, 4.99 mmol) was acylated by valeryl chloride (0.61 mL, 5.1 mmol) in presence of tin (IV) chloride (0.60 mL, 5.1 mmol) in methylene chloride (20 mL). ethyl 2-{[1-chloro-6-(3-pentanoyl-1-benzofuran-2-yl)-2-naphthyl]oxy} acetate was prepared. Purification by HPLC using 10% tert-butyl methyl ether in hexane as the mobile phase yielded the title compound as a light yellow solid (0.533 g), mp 95–97° C. Mass spectrum (+ESI, [M+H]$^+$) m/z 465. $^1$HNMR (500 MHz, DMSO-d$_6$): δ8.5 (s, 1H), 8.25 (d, 1H, J=8.9 Hz), 8.15 (d, 1H, J=9.0 Hz), 8.05 (t, 2H, J=8.6 Hz), 7.75 (d, 1H, J=7.8 Hz), 7.55 (d, 1H, J=9.2 Hz), 7.4–7.45 (m, 2H), 5.13 (s, 2H), 4.2 (q, 2H, J=7.0 Hz), 2.75 (t, 2H, J=7.3 Hz), 1.5–1.6 (m, 2H), 1.1–1.3 (m, 5H), and 0.7 ppm (t, 3H, J=7.3 Hz). Elemental Analysis for C$_{27}$H$_{25}$ClO$_5$: Calculated: C, 69.75; H, 5.42; N, 0.00. Found: C, 69.64; H, 5.20; N, 0.01.

Step 5

2-{[1-Chloro-6-(3-pentanoyl-1-benzofuran-2-yl)-2-naphthyl]oxy}acetic acid

Following the procedure described in Step 4 of Example 6, ethyl 2-{[1-chloro-6-(3-pentanoyl-1-benzofuran-2-yl)-2-naphthyl]oxy}acetate (0.477 g, 1.03 mmol) was hydrolyzed with potassium hydroxide (0.175 g, 3.12 mmol) in THF (10 mL) and water (10 mL). The title compound was obtained as a light yellow solid (0.249 g), mp 142–143° C. Mass spectrum (+ESI, [M+H]$^+$) m/z 437. $^1$HNMR (500 MHz, DMSO-d$_6$): δ13.0–13.5 (br, 1H), 8.5 (s, 1H), 8.25 (d, 1H, J=8.7 Hz), 8.1 (d, 1H, J=9.0 Hz), 8.05 (t, 2H, J=10.3 Hz), 7.75 (d,1H, J=8.0 Hz), 7.55 (d, 1H, J=9.2 Hz), 7.4–7.45 (m, 2H), 5.05 (s, 2H), 2.75 (t, 2H, J=7.2 Hz), 1.5–1.6 (m, 2H), 1.1–1.2 (m, 2H), and 0.75 ppm (t, 3H J=7.3 Hz). Elemental Analysis for C$_{25}$H$_{21}$ClO$_5$: Calculated: C, 68.73; H, 4.84; N, 0.00. Found: C, 68.56; H, 4.60; N, 0.08.

EXAMPLE 25

1-{2-[5-Chloro-6-(1H-1,2,3,4-tetraazol-5-ylmethoxy)-2-naphthyl]-1-benzofuran-3-yl}-1-pentanone

Step 1

2-[(6-Bromo-1-chloro-2-naphthyl)oxy]acetonitrile

Following the procedure described in Method B, Step 5 of Example 1, 2-[(6-bromo-1-chloro-2-naphthyl)oxy] acetonitrile was prepared from 6-bromo-1-chloro-2-naphthol (10.0 g, 38.8 mmol), cesium carbonate (25.4 g, 78.0 mmol) and bromoacetonitrile (4.1 mL, 59 mmol) in acetone (100 mL). Purification by flash chromatography using 5–12.5% ethyl acetate in hexane as an eluant yielded the title compound as a yellow solid (9.8 g), mp 126–127° C. $^1$HNMR (500 MHz, DMSO-d$_6$): δ8.3 (d, 1H, J=2.0 Hz), 8.05 (q, 2H, J=8.5 Hz), 7.8 (dd, 1H, J=9.1 Hz and 2.1 Hz), 7.7 (d, 1H, J=9.0 Hz), and 5.45 ppm (s, 2H). Elemental Analysis for C$_{12}$H$_7$BrClNO: Calculated: C, 48.60; H, 2.38; N, 4.72. Found: C, 48.40; H, 2.15; N, 4.60.

Step 2

2-{[6-(1-Benzofuran-2-yl)-1-chloro-2-naphthyl]oxy}acetonitrile

Following the procedure described in Step 1 of Example 1, 2-[(6-bromo-1-chloro-2-naphthyl)oxy]acetonitrile (9.7, 33 mmol) was coupled to 2-benzofuranboronic acid (6.35 g, 39 mmol), in the presence of[1,1'-bis(diphenylphosphino)ferrocene] dichloropalladium (II) complex with dichloromethane (1:1) (1.40 g, 1.71 mmol) and potassium carbonate (9.13 g, 66.1 mmol) in dioxane (330 mL) and water (3.3 mL). Purification by flash chromatography using 5–30% ethyl acetate in hexane and 7.5–50% ethyl acetate in hexane as eluants yielded 2-{[6-(1-benzofuran-2-yl)-1-chloro-2-naphthyl]oxy}acetonitrile as a light brown solid (6.13 g), mp 162–163° C. $^1$HNMR (300 MHz, DMSO-d$_6$): δ8.55 (s, 1H), 8.15–8.25 (m, 3H), 7.65–7.75 (m, 3H), 7.6 (s, 1H), 7.25–7.4 (m, 2H), and 5.45 ppm (s, 2H).

Step 3

2-{[1-Chloro-6-(3-pentanoyl-1-benzofuran-2-yl)-2-naphthyl]oxy}acetonitrile

Following the procedure described in Step 3 of Example 23, 2-{[6-(1-benzofuran-2-yl)-1-chloro-2-naphthyl]oxy}acetonitrile (6.12 g, 18.3 mmol) was acylated with valeryl chloride (2.2 mL, 19 mmol) in presence of tin (IV) chloride (2.2 mL, 19 mmol) in methylene chloride (37 mL). Purification by HPLC using 20% ethyl acetate in hexane as the mobile phase yielded 2-{[1-chloro-6-(3-pentanoyl-1- benzofuran-2-yl)-2-naphthyl]oxy}acetonitrile as a yellow waxy solid (2.55 g), mp 86–89° C. Mass spectrum (+ESI, [M+H]⁺) m/z 418. ¹HNMR (500 MHz, DMSO-d₆): δ8.55 (d, 1H, J=1.4 Hz), 8.3 (d, 1H, J=8.9 Hz), 8.25 (d, 1H, J=9.2 Hz), 8.0–8.05 (m, 2H), 7.75–7.8 (m, 2H), 7.4–7.5 (m, 2H), 5.5 (s, 2H), 2.75 (t, 2H, J=7.3 Hz), 1.5–1.6 (m, 2H), 1.1–1.2 (m, 2H), and 0.75 ppm (t, 3H, J=7.4 Hz). Elemental Analysis for $C_{12}H_{20}ClNO_3$: Calculated: C, 71.85; H, 4.82; N, 3.35. Found: C, 71.73; H, 4.59; N, 3.15.

Step 4

1-{2-[5-Chloro-6-(1H-1,2,3,4-tetraazol-5-ylmethoxy)-2-naphthyl]-1-benzofuran-3-yl}-1-pentanone Following the procedure described in Step 6 of Example 1, 1-{2-[5-chloro-6-(1H-1,2,3,4-tetraazol-5-ylmethoxy)-2-naphthyl]-1-benzofuran-3-yl}-1-pentanone was prepared from 2-{[1-chloro-6-(3-pentanoyl-1-benzofuran-2-yl)-2-naphthyl]oxy}acetonitrile (2.43 g, 5.82 mmol), sodium azide (1.91 g, 29.4 mmol) and ammonium chloride (1.59 g, 29.7 mmol) in DMF (13 mL). Purification by HPLC using 80% acetonitrile/0.1% formic acid in water as the mobile phase followed by crystallization from acetonitrile furnished the title compound as a light yellow solid (1.24 g), mp 168–169° C. Mass spectrum (+ESI, [M+H]⁺) m/z 461. ¹HNMR (500 MHz, DMSO-d₆): δ16.7–17.2 (br s, 1H), 8.5 (s, 1H), 8.25 (d, 1H, J=8.9 Hz), 8.2 (d, 1H, J=9.0 Hz), 8.0–8.05 (m, 2H), 7.8 (d, 1H, J=9.2 Hz), 7.75 (d, 1H, J=8.1 Hz), 7.4–7.45 (m, 2H), 5.8 (s, 2H), 2.75 (t, 2H, J=7.2 Hz), 1.5–1.6 (m, 2H), 1.1–1.2 (m, 2H), and 0.75 ppm (t, 3H, J=7.3 Hz). Elemental Analysis for $C_{25}H_{21}ClN_4O_3$: Calculated: C, 65.15; H, 4.59; N, 12.16. Found: C, 64.78; H, 4.39; N, 12.29.

EXAMPLE 26

{[6-(3-benzoyl-1-benzofuran-2-yl)-2-naphthyl]oxy}acetic acid

Step 1

6-(3-Benzoyl-1-benzofuran-2-yl)-2-methoxy-naphthylene

To a stirred solution of 6-(1-benzofuran-2-yl)-2-methoxy-naphthylene (0.991 g, 3.61 mmol) in $CS_2$ (40 mL) at 0° C. was added benzoyl chloride (0.461 mL, 3.97 mmol). The reaction was stirred at this temperature for 10 minutes and then $SnCl_4$ (0.507 mL, 4.33 mmol) was added dropwise. The reaction mixture was heated to reflux for 3 days. An additional amount of benzoyl chloride (0.461 mL, 3.97 mmol) followed by $SnCl_4$ (0.507 mL, 4.33 mmol) were added, and the mixture was kept at reflux for another day. The reaction mixture was quenched with MeOH (~5 mL). After concentration, the residue was diluted with $H_2O$ (20 mL) and EtOAc (200 mL). The organic layer was washed with sat. aq. $NaHCO_3$ (20 mL) and brine (20 mL) and then dried ($MgSO_4$). After concentration, the residue was purified by the Biotage Flash 40 apparatus (5–15% EtOAc:petroleum ether gradient) to afford the product (0.590 g) as a solid. Mass spectrum (+ESI, [M+H]⁺) m/z 379. ¹HNMR (500 MHz, DMSO-d₆): δ8.18 (s,1H), 7.70–7.88 (m, 5H), 7.42–7.60 (m, 4H), 7.29–7.41 (m, 4H), 7.18 (dd, 1H, J=1.4, 9.3 Hz), and 3.87 ppm (s, 3H).

Step 2

6-(3-Benzoyl-1-benzofuran-2-yl)-2-hydroxy-naphthylene

To a stirred solution of 6-(3-benzoyl-1-benzofuran-2-yl)-2-methoxy-naphthylene (0.590 g, 1.56 mmol) in $CH_2Cl_2$ (20 mL) cooled to −78° C. was added $BBr_3$ (4.21 mL, 1.0 M in $CH_2Cl_2$, 4.21 mmol) dropwise. The reaction was stirred at this temperature for 0.5 h and then warmed to room temperature for 2.5 h. The reaction mixture was quenched with MeOH (~5 mL) followed by dilution with $H_2O$ (20 mL) and EtOAc (200 mL). The organic layer was washed with brine (20 mL) and then dried ($Na_2SO_4$). After concentration, the residue was purified by preparatory plate chromatography (20% EtOAc:petroleum ether) to afford the product (0.428 g, 75%) as a solid. Mass spectrum (+ESI, [M+H]⁺) m/z 365. ¹HNMR (500 MHz, DMSO-d₆): δ10.06 (s, 1H), 8.13 (s, 1H), 7.72–7.88 (m, 4H), 7.62 (d, J=9.5 Hz, 1H), 7.39–7.55 (m, 4H) 7.39–7.28 (m, 3H), and 7.05–7.15 ppm (m, 2H).

Step 3

{[6-(3-Benzoyl-1-benzofuran-2-yl)-2-naphthyl]oxy}acetic acid methyl ester

To a stirred solution of 6-(3-benzoyl-1-benzofuran-2-yl)-2-hydroxy-naphthylene (0.128 g, 0.351 mmol) in acetone (5 mL) at room temperature was added $Cs_2CO_3$ (0.126 g, 0.386 mmol) followed by methyl bromoacetate (0.067 mL, 0.703 mmol) dropwise. The reaction was stirred at this temperature for 18 h and then diluted with EtOAc (100 mL). The organic layer was washed with 1 N HCl (10 mL), sat. aq. $NaHCO_3$ (10 mL), and brine (10 mL) and then dried ($MgSO_4$). After concentration, the residue was purified by preparatory plate chromatography (20% EtOAc:petroleum ether) to afford the product (0.142 g, 93%) as a solid. Mass spectrum (+ESI, [M+H]⁺) m/z 437. ¹HNMR (500 MHz, DMSO-d₆): δ8.20 (s,1H), 7.78–7.93 (m, 4H), 7.73 (d, J=9.2 Hz, 1H), 7.43–7.61 (m, 4H), 7.32–7.43 (m, 3H), 7.22–7.32 (m, 2H), 4.98 (s, 2H), and 3.72 ppm (s, 3H).

Step 4

{[6-(3-Benzoyl-1-benzofuran-2-yl)-2-naphthyl]oxy}acetic acid

To a stirred solution of {[6-(3-benzoyl-1-benzofuran-2-yl)-2-naphthyl]oxy}acetic acid methyl ester (0.128 g, 0.293 mmol) in THF:MeOH (3:2, 10 mL) at 0° C. was added 1 N KOH (0.879 mL, 0.879 mmol) dropwise. The reaction was stirred at this temperature for 0.25 h and then warmed to room temperature for 1 h. After concentration, the residue was diluted with $H_2O$, and this mixture was acidified to pH 1 with 2 N HCl. After stirring at room temperature for 3 h, the solid was filtered and washed with excess $H_2O$ and hexane. At this point, the compound was dried under high vacuum to afford the product (0.116 g) as a yellow solid, mp 178–181° C. Mass spectrum (−APCl, [M−H]⁻) m/z 421. ¹HNMR (500 MHz, DMSO-d₆): δ11.05–14.15 (br s, 1H), 8.17 (d, J=1.5 Hz, 1H), 7.84 (d, J=9.0 Hz, 1H), 7.76–7.81 (m, 3H), 7.70 (d, J=8.8 Hz, 1H), 7.52–7.57 (m, 2H), 7.42–7.51 (m, 2H), 7.31–7.37 (m, 3H), 7.18–7.24 (m, 2H), and 4.77 ppm (s, 2H). Elemental Analysis for $C_{27}H_{18}O_5 \cdot 0.5H_2O$: Calculated: C, 75.17; H, 4.44; N, 0.00 Found: C, 75.03; H, 4.34; N, 0.14

EXAMPLE 27

{2-[5-Bromo-6-(1H-tetraazol-5-ylmethoxy)-2-naphthyl]-1-benzofuran-3-yl}(phenyl) methanone Step 1

6-(3-Benzoyl-1-benzofuran-2-yl)-1-bromo-2-hydroxy-naphthylene

To a stirred solution of 6-(3-benzoyl-1-benzofuran-2-yl)-2-hydroxy-naphthylene (0.300 g, 0.823 mmol) in HOAc (8 mL) at 0° C. was added KOAc (0.097 g, 0.988 mmol). The reaction mixture was stirred for 10 minutes, and then a solution of Br$_2$ (0.047 mL, 0.906 mmol) in HOAc (2 mL) was added drop-wise over a period of ~10 minutes. The reaction mixture was allowed to warm to room temperature and stirred for 2 h. The reaction mixture was then diluted with H$_2$O (10 mL). The solid was filtered off and washed with excess water and hexane. This solid was then recrystallized from EtOAc:hexane to afford the product (0.207 g, 56%) as a solid. Mass spectrum (+ESI, [M+H]$^+$) m/z 443/ 445. $^1$HNMR (500 MHz, DMSO-d$_6$): δ10.87 (s, 1H), 8.18 (s, 1H), 7.92 (d, 1H, J=9.2 Hz), 7.74–7.87 (m, 3H), 7.71 (d, 1H, J=9.2 Hz), 7.44–7.59 (m, 3H), and 7.27–7.40 ppm (m, 5H).

Step 2

{[6-(3-Benzoyl-1-benzofuran-2-yl)-1-bromo-2-naphthyl]oxy}acetonitrile

The title compound was prepared as a solid (0.174 g, 77%) from 6-(3-benzoyl-1-benzofuran-2-yl)-1-bromo-2-hydroxy-naphthylene using bromoacetonitrile according to the procedure described in Method B, Step 5 of Example 1. Mass spectrum (+ESI, [M+H]$^+$) m/z 482/484. $^1$HNMR (500 MHz, DMSO-d$_6$): δ8.33 (s,1H), 8.12 (d, 1H, J=8.8 Hz), 8.06 (d, 1H, J=8.8 Hz), 7.77–7.87 (m, 4H), 7.65 (d, 1H, J=8.8 Hz), 7.56 (d, 1H, J=8.0 Hz), 7.47–7.53 (m, 2H), 7.31–7.42 (m, 3H), and 5.47 ppm (s, 2H).

Step 3

{2-[5-Bromo-6-(1H-tetraazol-5-ylmethoxy)-2-naphthyl]-1-benzofuran-3-yl}(phenyl) methanone To a stirred solution of {[6-(3-benzoyl-1-benzofuran-2-yl)-1-bromo-2-naphthyl]oxy} acetonitrile (0.174 g, 0.361 mmol) in DMF (10 mL) at room temperature was added NaN$_3$ (0.117 g, 1.81 mmol) followed by NH$_4$Cl (0.097 g, 1.81 mmol). The reaction was heated to 100° C. for 2 h. After this time, it was concentrated and diluted with 2 N HCl (~5 mL). This mixture was stirred at room temperature for 1 h. The solid was filtered and washed with excess water and hexane then dried under high vacuum to afford the product (0.190 g, 99%) as a light. brown solid, mp>183° C. (dec.). Mass spectrum (+APCl, [M+NH$_4$]$^+$) m/z 542. $^1$HNMR (500 MHz, DMSO-d$_6$): δ14.75–17.75 (br s, 1H), 8.28 (d, 1H, J=2.0 Hz), 8.03 (d, 1H, J=9.0 Hz), 8.00 (d, 1H, J=8.8 Hz), 7.78–7.83 (m, 3H), 7.76 (dd, 1H, J=1.7, 8.8 Hz), 7.67 (d, 1H, J=9.0 Hz), 755 (d, J=7.6 Hz, 1H), 7.32–7.38 (m, 3H), 7.45–7.52 (m, 2H), and 5.71 ppm (s, 2H). Elemental analysis for C$_{27}$H$_{17}$BrN$_4$O$_3$.1.0H$_2$O: Calculated: C, 59.68; H, 3.52; N, 10.31. Found: C, 59.72; H, 3.23; N, 10.51.

EXAMPLE 28

2-{[1-Bromo-6-(3-bromo-1-benzofuran-2-yl)-2-naphthyl]oxy}-3-phenylpropanoic acid Step 1

6-(3-Bromo-1-benzofuran-2-yl)-1-bromo-2-hydroxy-naphthylene

The title compound was prepared as a solid (1.16 g, 36%) from 6-(1-benzofuran-2-yl)-2-hydroxy-naphthylene using 2.2 equivalents of Bromine following the procedure described in Step 1 of Example 27. Mass spectrum (+ESI, [M+H]$^+$) m/z 419. $^1$HNMR (500 MHz, DMSO-d$_6$): δ10.90 (s, 1H), 8.63 (s, 1H), 8.31 (d, 1H, J=9.2 Hz), 8.19 (d, 1H, J=9.2 Hz), 8.03 (d, 1H, J=9.2 Hz), 7.74 (d, 1H, J=8.7 Hz), 7.62 (d, 1H, J=7.8 Hz), 7.40–7.53 (m, 2H), and 7.38 ppm (d, 1H, J=9.2 Hz), Step 2

2-{[1-Bromo-6-(3-bromo-1-benzofuran-2-yl)-2-naphthyl]oxy}-3-phenylpropanoic acid methyl ester To a stirred solution of 3-phenyllactic acid methyl ester (0.195, 1.08 mmol) in THF (10 mL) at 0° C. was added 6-(3-bromo-1-benzofuran-2-yl)-1-bromo-2-hydroxy-naphthylene (0.300 g, 0.718 mmol). To this mixture was added PPh$_3$ (0.283 g, 1.08 mmol) followed by DEAD (0.170 mL, 1.08 mmol) drop-wise. The reaction mixture was stirred at this temperature for 0.5 h then at room temperature for 2 h. The reaction mixture was diluted with EtOAc (200 mL). The organic layer was washed with 1 N HCl (20 mL), sat. aq. NaHCO$_3$ (20 mL), and brine (20 mL) and then dried (MgSO$_4$). After concentration, the residue was purified on a Biotage Flash 40 apparatus (5–15% EtOAc:petroleum ether gradient) to afford the product (0.331 g) as a solid. Mass spectrum (+ESI, [M+Na]$^+$) m/z 603. $^1$HNMR (500 MHz, DMSO-d$_6$): δ8.67 (s, 1H), 8.37 (d, 1H, J=9.2 Hz), 8.26 (d, 1H, J=9.2 Hz), 8.12 (d, 1H, J=9.2 Hz), 7.74 (d, 1H, J=8.1 Hz), 7.62 (d, 1H, J=8.1 Hz), 7.20–7.53 (m, 8H), 5.52 (dd, 1H, J=6.2, 9.3 Hz), 3.67 (s, 3H), and 3.27–3.43 ppm (m, 2H).

Step 3

2-{[1-Bromo-6-(3-bromo-1-benzofuran-2-yl)-2-naphthyl]oxy}-3-phenylpropanoic acid The title compound was prepared as a white solid (0.224 g, 72%) from 2-{[1-bromo-6-(3-bromo-1-benzofuran-2-yl)-2-naphthyl]oxy}-3-phenylpropanoic acid methyl ester following the procedure described in from Step 4 of Example 26, mp 206–209° C. Mass spectrum (–APCl, [M–H]$^-$) m/z 563. $^1$HNMR (500 MHz, DMSO-d$_6$): δ12.65–13.85 (br s, 1H), 8.64 (d, 1H, J=1.7 Hz), 8.34 (dd, 1H, J=1.7, 9.0 Hz), 8.23 (d, 1H, J=9.0 Hz), 8.11 (d, 1H, J=9.0 Hz), 7.73 (d, 1H, J=8.1 Hz), 7.60 (dd, 1H, J=1.0, 7.6 Hz), 7.39–7.50 (m, 4H), 7.37 (d, 1H, J=9.3 Hz), 7.28–7.33 (m, 2H), 7.20–7.25 (m, 1H), 5.36 (dd, 1H, J=4.1, 7.8 Hz), and 3.24–3.40 ppm (m, 2H). Elemental analysis for C$_{27}$H$_8$Br$_2$O$_4$.0.25H$_2$O: Calculated: C, 56.82; H, 3.27; N, 0.00. Found: C, 56.62; H, 3.04; N, 0.02.

EXAMPLE 29

{[1-Phenyl-6-(3-phenyl-1-benzofuran-2-yl)-2-naphthyl]oxy}acetic acid

Step 1

6-(3-Phenyl-1-benzofuran-2-yl)-1-phenyl-2-hydroxy-naphthylene

The title compound was prepared as a solid (0.376 g, 44%) from 6-(3-bromo-1-benzofuran-2-yl)-1-bromo-2-hydroxy-naphthylene using 2.4 equivalents of phenyl boronic acid according to the procedure described in Step 1 of Example 1. Mass spectrum (+ESI, [M+H]$^+$) m/z 413. $^1$HNMR (300 MHz, DMSO-d$_6$): δ9.73 (s, 1H), 8.16 (s, 1H), 7.78 (d, 1H, J=8.3 Hz), 7.72 (d, 1H, J=8.3 Hz), 7.45–7.54–7.54 (m, 8H), 7.34–7.45 (m, 3H), 7.27–7.34 (m, 4H), and 7.24 ppm (d, 1H, J=9.1 Hz).

Step 2

{[1-Phenyl-6-(3-phenyl-1-benzofuran-2-yl)-2-naphthyl]oxy}acetic acid methyl ester The title compound was prepared as a solid (0.124 g) from 6-(3-phenyl-1-benzofuran-2-yl)-1-phenyl-2-hydroxynaphthylene according to the procedure described in Step 3 of Example 26. Mass spectrum (+ESI, [M+H]$^+$) m/z 485. $^1$HNMR (400 MHz, DMSO-d$_6$): δ8.26 (s, 1H), 7.94 (d, J =9.2 Hz, 1H), 7.73 (d, J=9.2 Hz, 1H), 7.23–7.63 (m, 16H), 4.92 (s, 2H), and 3.67 ppm (s, 3H).

Step 3

{[1-Phenyl-6-(3-phenyl-1-benzofuran-2-yl)-2-naphthyl]oxy}acetic acid

The title compound was prepared as a white solid (0.117 g, 99%) from {[1-phenyl-6-(3-phenyl-1-benzofuran-2-yl)-2-naphthyl]oxy}acetic acid methyl ester following the procedure described in Step 4 of Example 26, mp 202–203° C. Mass spectrum (+APCl, [M+H]$^+$) m/z 471. $^1$HNMR (500 MHz, DMSO-d$_6$): δ12.55–13.55 (br s, 1H), 8.23 (d, 1H, J=1.4 Hz), 7.93 (d, 1H, J=9.1 Hz), 7.71 (d, 1H, J=8.1 Hz), 7.24–7.53 (m, 16H), and 4.77 ppm (s, 2H). Elemental analysis for $C_{32}H_{22}O_4 \cdot 1.0H_2O$: Calculated: C, 78.67; H, 4.95; N, 0.00. Found: C, 78.84; H, 4.39; N, 0.14.

EXAMPLE 30

1-{2-[5-Bromo-6-(1H-tetrazol-5-ylmethoxy)-naphthalen-2-yl]-5-chloro-benzofuran-3-yl}-pentan-1-one

Step 1

4-(6-Methoxy-2-naphthyl)-2-methyl-3-butyn-2-ol

A mixture of 6-methoxy-2-bromonaphthalene (14.23 g, 60.0 mmol), copper (I) iodide (0.17 g, 0.90 mmol), dichlorobis(triphenylphosphine)palladium(II) (0.63 g, 0.90 mmol), and 2-methyl-3-butyn-2-ol (8.7 mL, 90 mmol) in diethylamine (100 mL) was heated at reflux for 16 hours, cooled to room temperature and solvent evaporated. The residue was purified by flash chromatography using 15–25% ethyl acetate in hexane as an eluant. Drying at 80° C. for 20 minutes afforded 4-(6-methoxy-2-naphthyl)-2-methyl-3-butyn-2-ol as a light orange solid (14.4 g), mp: 118–119° C. $^1$HNMR (300 MHz, DMSO-d$_6$): δ7.95 (s, 1H), 7.75–7.85 (m, 2H), 7.4 (dd, 1H, J=8.4 Hz and 1.5 Hz), 7.35 (d, 1H, J=2.4 Hz), 7.2 (dd, 1H, J=8.5 Hz and 1.5 Hz), 5.5 (s, 1H), 3.9 (s, 3H), and 1.5 ppm (s, 6H).

Step 2

2-Ethynyl-6-methoxynaphthalene

A mixture of 4-(6-methoxy-2-naphthyl)-2-methyl-3-butyn-2-ol (16.9 g, 69.7 mmol), powdered sodium hydroxide (3.7 g, 93 mmol) in toluene (350 mL) was refluxed for 16 hours in a flask equipped with a Dean Stark water trap. The mixture was allowed to cool to room temperature and the solvent was evaporated. The residue was purified by flash chromatography using 2.5–3% ethyl acetate in hexane as an eluant. Drying at 68° C. for 20 minutes afforded 2-ethynyl-6-methoxynaphthalene as a light yellow solid (10.1 g, 80%), mp: 111–112° C. Mass spectrum (+EI, M+) m/z 182. $^1$HNMR (400 MHz, DMSO-d$_6$): δ8.00 (s, 1H), 7.8–7.85 (m, 2H), 7.45 (dd, 1H, J=8.4 Hz and 1.6 Hz), 7.35 (d, 1H, J=2.4 Hz), 7.2 (dd, 1H, J=8.9 Hz and 2.6 Hz), 4.2 (s, 1H), and 3.9 ppm (s, 3H). Elemental Analysis for $C_{13}H_{10}O$: Calculated: C, 85.69; H, 5.53; N, 0.00. Found: C, 85.50; H, 5.22; N, 0.07.

Step 3

5-Chloro-2-(6-methoxy-naphth-2-yl)-1-benzofuran

A mixture of 2-ethynyl-6-methoxynaphthalene (1.82 g, 10 mmol), 2-bromo-4-chlorophenol (2.01 g, 10 mmol), copper (I) iodide (0.1 g, 0.52 mmol), tetrakis(triphenylphosphine) palladium (0.58 g, 0.5 mmol) in triethylamine (10 mL) and diethylamine (10 mL) was heated at reflux for 1 hour under an atmosphere of nitrogen then cooled to room temperature. The solid was collected by filtration, washed with ether and dried to give the title compound as a solid (2.0 g). $^1$HNMR (300 MHz, DMSO-d$_6$): δ8.4 (s, 1H), 8.0–7.9 (m, 3H), 7.75 (d, 1H, J=1.8 Hz), 7.69 (d, 1H, J=9.2 Hz), 7.46 (s, 1H), 7.38–7.32 (m, 2H), 7.24 (dd, 1H, J=9.2, 1.8 Hz), and 3.9 ppm (s, 3H).

Step 4

1-[5-Chloro-2-(6-methoxy-naphthalen-2-yl)-benzofuran-3-yl]-pentan-1-one

Following the procedure described in Step 2 of Example 1, the title compound was prepared by the acylation of 5-chloro-2-(6-methoxy-naphth-2-yl)-1-benzofuran (6.6 g, 21.37 mmol), with valeryl chloride (2.3 mL, 16 mmol) in presence of tin (IV) chloride in chloroform. Purification by flash chromatography on silica gel using 2.5% ethyl acetate in hexane as the mobile phase yielded the title compound as a white solid (5.6 g), mp 119–120° C. Mass spectrum (+ESI, [M+NH$_4$]$^+$) m/z 410. $^1$HNMR (400 MHz, DMSO-d$_6$): δ8.36 (d, 1H, J=1.6 Hz), 8.02 (dd, 2H, J=7.0, 2.2 Hz), 7.99 (s, 1H), 7.81 (dd, 1H, J=8.6, 1.7 Hz), 7.77 (d, 1H, J=8.8 Hz), 7.48–7.44 (m, 2H), 7.27 (dd, 1H, J=8.8, 2.3 Hz), 3.92 (s, 3H), 2.69 (t, 2H, J=7.3 Hz), 1.51 (m, 2H), 1.1 (m, 2H), and 0.68 ppm (t, 3H, J=7.3 Hz). Elemental Analysis for $C_{24}H_{21}ClO_3$: Calculated: C, 73.37; H, 5.39; N, 0.00. Found: C, 73.34; H, 5.27; N, 0.03.

Step 5

1-[5-Chloro-2-(6-hydroxy-naphthalen-2-yl)-benzofuran-3-yl]-pentan-1-one

Following the procedure described in Step 3 of Example 1,1-[5-chloro-2-(6-hydroxy-naphthalen-2-yl)-benzofuran-3-yl]-pentan-1-one was prepared 1-[5-chloro-2-(6-methoxy-naphthalen-2-yl)-benzofuran-3-yl]-pentan-1-one (5.6 g, 14.25 mmol), and boron tribromide (1M solution, 45 mL, 45 mmol) in methylene chloride (200 mL). After work-up, stirring of the solid residue with methanol and filtering afforded the title compound as a solid. (3.2 g), A sample was dissolved in chloroform and filtered through a plug of celite. The solvent was evaporated and the residue was crystallized from methanol to give white crystals, mp 156–157° C. Mass spectrum (+APCl, [M+H]$^+$) m/z 379. $^1$HNMR (400 MHz, DMSO-d$_6$): δ10.15 (br s,1H), 8.29 (d, 1H, J=1.2 Hz), 8.01 (d, 1H, J=2.2 Hz), 7.93 (d, 1H, J=8.8 Hz), 7.86 (d, 1H, J=8.6 Hz), 7.77–7.72 (m, 2H), 7.46 (dd, 1H, J=8.8, 2.2 Hz), 7.22 (d, 1H, J=2.2 Hz), 7.18 (dd, 1H, J=8.8, 2.4 Hz), 2.69 (t, 2H, J=7.3 Hz), 1.55–1.47 (m, 2H), 1.15–1.05 (m, 2H), and 0.68 ppm (t, 3H, J=7.3 Hz). Elemental Analysis for $C_{23}H_{19}ClO_3$: Calculated: C, 72.92; H, 5.05; N, 0.00. Found: C, 72.73; H, 4.99; N, 0.08.

Step 6

1-2-(5-Bromo-6-hydroxy-naphthalen-2-yl-)-5-chloro-benzofuran-3-yl]-pentan-1-one Following the procedure described in Step 4 of Example 1, 1-[5-chloro-2-(6-hydroxy-naphthalen-2-yl)-benzofuran-3-yl]-pentan-1-one (3.0 g, 7.7 mmol) was brominated using bromine (0.45 mL, 8.8 mmol, in 10 mL of acetic acid), and potassium acetate (1 g. 11.6 mmol) in glacial acetic acid (80 mL). Crystallization from methanol furnished the title compound as an off-white solid (2.8 g), mp 189–191° C. Mass spectrum (–APCl, [M–H]$^-$) m/z 455, 457, 459. $^1$HNMR (400 MHz, DMSO-d$_6$): δ11.0 (br s, 1H), 8.40 (d, 1H, J=1.7 Hz), 8.15 (d, 1H, J=8.8 Hz), 8.02 (d, 1H, J=2.2 Hz), 7.99 (d, 1H, J=8.8 Hz), 7.93 (dd, 1H, J=8.8, 1.9 Hz), 7.77 (d, 1H, J=8.8 Hz), 7.47 (dd, 1H, J=8.8, 2.2 Hz), 7.38 (d, 1H, J=8.8 Hz), 2.71 (t, 2H, J=7.3 Hz), 1.55–1.48 (m, 2H), 1.16–1.06 (m, 2H), and 0.69 ppm (t, 3H, J=7.3 Hz). Elemental Analysis for C$_{23}$H$_{18}$BrClO$_3$: Calculated: C, 60.35; H, 3.96; N, 0.00. Found: C, 60.17; H, 3.7; N, 0.02.

Step 7

[1-Bromo-6-(5-chloro-3-pentanoyl-benzofuran-2-yl)-naphthalen-2-yloxy]-acetonitrile Following the procedure described in Method B, Step 5 of Example 1, [1-bromo-6-(5-chloro-3-pentanoyl-benzofuran-2-yl)-naphthalen-2-yloxy]-acetonitrile was prepared from 1-[2-(5-bromo-6-hydroxy-naphthalen-2-yl)-5-chloro-benzofuran-3-yl]-pentan-1-one (0.458 g, 1.0 mmol), cesium carbonate (0.5 g, 1.53 mmol), and bromo acetonitrile (0.1 mL, 1.45 mmol) in acetone (20 mL). The title compound was obtained from ether as an off-white solid (0.430 g), mp 104–106° C. Mass spectrum (+ESI, [M+NH$_4$]$^+$) m/z 513. $^1$HNMR (400 MHz, DMSO-d$_6$): δ8.54 (d, 1H, J=1.5 Hz), 8.28 (dd, 2H, J=8.8, 2.5 Hz), 8.06–8.03 (m, 2H), 7.80 (d, 1H, J=8.8 Hz), 7.74 (d, 1H, J=9.0 Hz), 7.50 (dd, 1H, J=8.8, 2.2 Hz), 5.48 (s, 2H), 2.73 (t, 2H, J=7.3 Hz), 1.56–1.49 (m, 2H), 1.17–1.08 (m, 2H), and 0.70 ppm (t, 3H, J=7.3 Hz). Elemental Analysis for C$_{25}$H$_{19}$BrClNO$_3$.00.5H$_2$O: Calculated: C, 59.37; H, 3.99; N, 2.78. Found: C, 59.30; H, 3.72; N, 2.84.

Step 8

1-{2-[5-Bromo-6-(1H-tetrazol-5-ylmethoxy)-naphthalen-2-yl]-5-chloro-benzofuran-3-yl}-pentan-1-one Following the procedure described in Step 6, of Example 1, the title compound was prepared from [1-bromo-6-(5-chloro-3-pentanoyl-benzofuran-2-yl)-naphthalen-2-yloxy]-acetonitrile (0.4 g, 0.8 mmol), sodium azide (0.325 g, 5 mmol) and ammonium chloride (0.268 g, 5 mmol) in DMF (20 mL). The compound was purified by flash chromatography on acid treated silica gel using 50% ethyl acetate in hexane as the mobile phase. The title compound was obtained as an off-white solid (0.32 g), mp 133–135° C. Mass spectrum (–ESI, [M–H]$^-$) m/z 537. $^1$HNMR (400 MHz, DMSO-d$_6$): δ8.51 (d, 1H, J=1.5 Hz), 8.26–8.20 (m, 2H), 8.03–7.99 (m, 2H), 7.80–7.76 (m, 2H), 7.48 (dd, 1H, J=8.8, 2.2 Hz), 5.78 (s, 2H), 2.73 (t, 2H, J=7.3 Hz), 1.56–1.49 (m, 2H), 1.17–1.08 (m, 2H), and 0.70 ppm (t, 3H, J=7.3 Hz). Elemental Analysis for C$_{25}$H$_{20}$BrClN$_4$O$_3$: Calculated: C, 55.63; H, 3.73; N, 10.38. Found: C, 55.54; H, 3.59; N, 10.24.

EXAMPLE 31

[1-Bromo-6-(5-chloro-3-pentanoyl-benzofuran-2-yl)-naphthalen-2-yloxy]-acetic acid

Step 1

[1-Bromo-6-(5-chloro-3-pentanoyl-benzofuran-2-yl)-naphthalen-2-yloxy]-acetic acid ethyl ester Following the procedure described in Method B, Step 5 of Example 1, [1-bromo-6-(5-chloro-3-pentanoyl-benzofuran-2-yl)-naphthalen-2-yloxy]-acetic acid ethyl ester was prepared from 1-[2-(5-bromo-6-hydroxy-naphthalen-2-yl)-5-chloro-benzofuran-3-yl]-pentan-1-one (0.458 g, 1.0 mmol), cesium carbonate (0.396 g, 1.22 mmol), and ethyl bromoacetate (0.13 mL, 1.2 mmol) in acetone (10 mL). Evaporation of the solvent and treatment of the residue with ethyl acetate/hexane afforded the title compound as an off-white solid (0.320 g), mp 88–91° C. Mass spectrum (+APCl, [M+H]$^+$) m/z 543, 545. $^1$HNMR (400 MHz, DMSO-d$_6$): δ8.49 (d, 1H, J=1.6 Hz), 8.25 (d, 1H, J=9.0 Hz), 8.15 (d, 1H, J=9.0 Hz), 8.03 (d, 1H, J=2.2 Hz), 8.00 (dd, 1H, J=9.8, 2.0 Hz), 7.79 (d, 1H, J=8.8 Hz), 7.54 (d, 1H, J=9.0 Hz), 7.49 (dd, 1H, J=8.8, 2.2 Hz), 5.14 (s, 2H), 4.18 (q, 2H, J=7.1 Hz), 2.72 (t, 2H, J=7.3 Hz), 1.56–1.48 (m, 2H), 1.21 (t, 3H, J=7.3 Hz), 1.17–1.07 (m, 2H), and 0.69 ppm (t, 3H, J=7.3 Hz). Elemental Analysis for C$_{27}$H$_{24}$BrClO$_5$.0.5H$_2$O: Calculated: C, 58.66; H, 4.56; N, 0.00. Found: C, 58.65; H, 4.21; N, 0.03.

Step 2

[1-Bromo-6-(5-chloro-3-pentanoyl-benzofuran-2-yl)-naphthalen-2-yloxy]-acetic acid Following the procedure described in Step 4 of Example 6, [1-bromo-6-(5-chloro-3-pentanoyl-benzofuran-2-yl)-naphthalen-2-yloxy]-acetic acid ethyl ester (0.25 g, 0.46 mmol) was hydrolyzed with potassium hydroxide (0.300 g, 5.36 mmol) in THF (10 mL) and water (10 mL). Crystallization from ethyl acetate afforded the title compound as an off-white solid (0.21 g), mp 130–132° C. Mass spectrum (–APCl, [M–H]$^-$) m/z 513, 515, 517. $^1$HNMR (400 MHz, DMSO-d$_6$): δ13.25 (br s,1H), 8.48 (d,1H, J=1.5 Hz), 8.25 (d, 1H, J=9.0 Hz), 8.14 (d, 1H, J=9.0 Hz), 8.04 (d, 1H, J=2.2 Hz), 7.99 (dd, 1H, J=9.0, 1.8 Hz), 7.79 (d, 1H, J=8.8 Hz), 7.52–7.48 (m, 2H), 5.03 (s, 2H), 2.72 (t, 2H, J=7.3 Hz), 1.56–1.48 (m, 2H), 13H, 1.17–1.07 (m, 2H), and 0.70 ppm (t, 3H, J=7.4 Hz). Elemental Analysis for C$_{25}$H$_{20}$BrClO$_5$: Calculated: C, 58.22; H, 3.91; N, 0.00. Found: C, 58.24; H, 3.73; N, 0.03.

EXAMPLE 32

1-{5-Chloro-2-[6-(1H-tetrazol-5-ylmethoxy)-naphthalen-2-yl]-benzofuran-3-yl}-pentan-1-one

Step 1

[6-(5-Chloro-3-pentanoyl-benzofuran-2-yl)-naphthalen-2-yloxy]-acetonitrile

Following the procedure described in Method B, Step 5 of Example 1, [6-(5-Chloro-3-pentanoyl-benzofuran-2-yl)-naphthalen-2-yloxy]-acetonitrile was prepared from 1-[5-chloro-2-(6-hydroxy-naphthalen-2-yl)-benzofuran-3-yl]-pentan-1-one (0.379 g, 1.0 mmol), cesium carbonate (0.5 g, 1.53 mmol), and bromo acetonitrile (0.1 mL, 1.45 mmol) in acetone (20 mL). The title compound was obtained as a white solid (0.36 g), mp 98–100° C. Mass spectrum (+APCl, [M+H]$^+$) m/z 418. $^1$HNMR (400 MHz, DMSO-d$_6$): δ8.42 (s, 1H), 8.10 (d, 1H, J=9.0 Hz), 8.05–8.03 (m, 2H), 7.88 (dd, 1H, J=8.3, 1.7 Hz), 7.78 (d, 1H, J=8.5 Hz), 7.63 (d, 1H, J=2.2 Hz), 7.50–7.46 (m, 1H), 7.38 (dd, 1H, J=9.0, 2.7 Hz), 5.35 (s, 2H), 2.70 (t, 2H, J=7.5 Hz), 1.55–1.48 (m, 2H), 1.15–1.06 (m, 2H), and 0.68 ppm (t, 3H, J=7.3 Hz). Elemental Analysis for C$_{25}$H$_{20}$ClNO$_3$: Calculated: C, 71.85; H, 4.82; N, 3.35. Found: C, 71.86; H, 4.54; N, 3.25.

Step 2

1-{5-Chloro-2-[6-(1H-tetrazol-5-ylmethoxy)-naphthalen-2-yl]-benzofuran-3-yl}-pentan-1-one Following the procedure described in Step 6, of Example 1, the title compound was prepared from [6-(5-Chloro-3-pentanoyl-benzofuran-2-yl)-naphthalen-2-yloxy]-acetonitrile (0.31 g, 0.74 mmol), sodium azide (0.325 g, 5 mmol) and ammonium chloride (0.268 g, 5 mmol) in DMF (20 mL). Trituration with methanol afforded the title compound as a yellow solid (0.26 g), mp 178–180° C. Mass spectrum (+APCl, [M+H]$^+$) m/z 461. $^1$HNMR (400 MHz, DMSO-d$_6$): δ8.4 (s, 1H), 8.07–7.99 (m, 3H), 7.85 (dd, 1H, J=8.5, 1.7 Hz), 7.77 (d, 1H, J=8.8 Hz),), 7.64 (d, 1H, J=2.2 Hz),), 7.48 (dd, 1H, J=8.8, 2.2 Hz),), 7.38 (dd, 1H, J=8.8, 2.4 Hz), 5.66 (s, 2H), 2.70 (t, 2H, J=7.4 Hz), 1.56–1.48 (m, 2H), 1.15–1.06 (m, 2H), and 0.69 ppm (t, 3H, J=7.5 Hz). Elemental Analysis for $C_{25}H_{21}ClN_4O_3$.0.5$H_2O$: Calculated: C, 64.52; H, 4.66; N, 12.04. Found: C, 64.40; H, 4.42; N, 12.07.

EXAMPLE 33

[6-(5-Chloro-3-pentanoyl-benzofuran-2-yl)-naphthalen-2-yloxy]-acetic acid

Step 1

[6-(5-Chloro-3-pentanoyl-benzofuran-2-yl)-naphthalen-2-yloxy]-acetic acid ethyl ester Following the procedure described in Method B, Step 5 of Example 1, [6-(5-chloro-3-pentanoyl-benzofuran-2-yl)-naphthalen-2-yloxy]-acetic acid ethyl ester was prepared from 1-[5-chloro-2-(6-hydroxy-naphthalen-2-yl)-benzofuran-3-yl]-pentan-1-one (0.379 g, 1.0 mmol), cesium carbonate (0.396 g, 1.22 mmol), and ethyl bromoacetate (0.13 mL, 1.2 mmol) in acetone (10 mL). Evaporation of the solvent and treatment of the residue with ether/hexane afforded the title compound as an off-white solid (0.310 g), mp 80–83° C. Mass spectrum (+APCl, [M+H]$^+$) m/z 465, 467. $^1$HNMR (400 MHz, DMSO-d$_6$): δ8.38 (d, 1H, J=1.6 Hz), 8.04–8.02 (m, 2H), 7.97 (d, 1H, J=8.8 Hz), 7.82 (dd, 1H, J=8.5, 1.8 Hz), 7.77 (d, 1H, J=8.8 Hz), 7.48 (dd, 1H, J=8.8, 1.7 Hz), 7.42 (d, 1H, J=2.5 Hz), 7.33 (dd, 1H, J=9.0, 2.7 Hz), 4.96 (s, 2H), 4.20 (q, 2H, J=7.1 Hz), 2.69 (t, 2H, J=7.3 Hz), 1.56–1.47 (m, 2H), 1.23 (t, 3H, J=7.1 Hz), 1.15–1.05 (m, 2H), and 0.68 ppm (t, 3H, J=7.4 Hz). Elemental Analysis for $C_{27}H_{25}ClO_5$.0.25$H_2O$: Calculated: C, 69.08; H, 5.47; N, 0.00. Found: C, 69.01; H, 5.17; N, 0.03.

Step 2

[6-(5-Chloro-3-pentanoyl-benzofuran-2-yl)-naphthalen-2-yloxy]-acetic acid

Following the procedure described in Step 4 of Example 6, [6-(5-chloro-3-pentanoyl-benzofuran-2-yl)-naphthalen-2-yloxy]-acetic acid ethyl ester (0.26 g, 0. mmol) was hydrolyzed with potassium hydroxide (0.300 g, 5.36 mmol) in THF (20 mL) and water (10 mL). Crystallization from ethyl acetate afforded the title compound as an off-white solid (0.22 g), mp 158–160° C. Mass spectrum (−APCl, [M−H]$^−$) m/z 435, 437. $^1$HNMR (400 MHz, DMSO-d$_6$): δ13.14 (br s, 1H), 8.37 (d, 1H, J=1.2 Hz), 8.03–8.01 (m, 2 H), 7.97 (d, 1H, J=8.5 Hz), 7.81 (dd, 1H, J=8.3, 1.7 Hz), 7.77 (d, 1H, J=8.8 Hz), 7.48 (dd, 1H, J=8.8, 2.2 Hz), 7.40 (d, 1H, J=2.7 Hz), 7.32 (dd, 1H, J=9.0, 2.5 Hz), 4.85 (s, 2H), 2.69 (t, 2H, J=7.3 Hz), 1.55–1.48 (m, 2H), 1.13–1.05 (m, 2H), and 0.69 ppm (t, 3H, J=7.4 Hz). Elemental Analysis for $C_{25}H_{21}ClO_5$.0.4$H_2O$: Calculated: C, 67.61; H, 4.95; N, 0.00. Found: C, 67.51; H, 4.66; N, 0.05.

EXAMPLE 34

5-[6-(3-Pentyl-benzofuran-2-yl)-naphthalen-2-yloxymethyl]-1H-tetrazole

Step 1

1-[2-(6-Methoxy-naphthalen-2-yl)-benzofuran-3-yl]-pentan-1-ol

Sodium borohydride ((7.56 g, 200 mmol) was added portion-wise to the stirring mixture of 1-[2-(6-methoxy-2-naphthyl)-1-benzofuran-3-yl]-1-pentanone (17.9 g, 50 mmol) in ethanol (600 mL). The mixture was stirred at room temperature for 2 hours then filtered. The solids were dissolved in methylene chloride and 2N hydrochloric acid solution. The organic phase was washed with water, dried over anhydrous magnesium sulfate and solvent evaporated to give the title compound (16.6 g). $^1$HNMR (300 MHz, DMSO-d$_6$): δ8.2 (s, 1H), 7.98–7.92 (m, 2H), 7.9–7.82 (m, 2H) 7.62 (d, 1H, J=7.5 Hz), 7.38 (s, 1H), 7.35–7.22 (m, 3H), 5.46 (d, 1H, J=3.6 Hz), 5.15–5.07 (m, 1H), 3.92 (s, 3H), 2.12–1.97 (m, 1H), 1.95–1.82 (m, 1H), 1.44–1.21 (m, 3H), and 0.69 ppm (t, 3H, J=7.4 Hz).

Step 2

2-(6-Methoxy-naphthalen-2-yl)-3-pentyl-benzofuran

The solution of 1-[2-(6-methoxy-naphthalen-2-yl)-benzofuran-3-yl]-pentan-1-ol (15.5 g, 43 mmol) and triethyl silane (10 g, 86 mmol) in methylene chloride (300 mL) was cooled in an ice bath. Trifluoro acetic acid (50 mL) was added gradually. The mixture was stirred at while cooling for 2 hours then was allowed to warm to room temperature. The solvent was evaporated. The residue was dissolved in ether and washed with sodium bicarbonate solution, then with water. The solvent was evaporated and the residue was purified by flash chromatography on silica gel using 4% ethyl acetate in hexane as the mobile phase. The product was obtained as a clear oil (8.9 g). $^1$HNMR (300 MHz, DMSO-d$_6$): δ8.22 (s, 1H), 7.98–7.92 (m, 2H), 7.95–7.90 (m, 2H), 7.64 (d, 1H, J=8.8 Hz), 7.65 (d, 1H, J=8.8 Hz), 7.58 (d, 1H, J=8.8 Hz), 7.38–7.20 (m, 4H), 3.90 (s, 3H), 2.96 (t, 1H, J=9.9 Hz), 1.70 (p, 1H, J=7.0 Hz), 1.42–1.26 (m, 4H), and 0.82 ppm (t, 3H, J=7.4 Hz).

Step 3

6-(3-Pentyl-benzofuran-2-yl)-naphthalen-2-ol

Following the procedure described in Step 3 of Example 1, the title compound was prepared from 2-(6-methoxy-naphthalen-2-yl)-3-pentyl-benzofuran (8.0 g, 23.3 mmol) and boron tribromide (70 mL of 1 M solution in methylene chloride, 70 mmol). Purification by chromatography on a Biotage apparatus using 4% ethyl acetate in hexane as the mobile phase afforded the title compound as a solid (5.0 g), mp 100–102° C. Mass spectrum (+APCl, [M+H]$^+$) m/z 331. $^1$HNMR (300 MHz, DMSO-d$_6$): δ9.94 (s, 1H), 8.17 (s, 1H), 7.9 (d, 1H, J=8.8 Hz), 7.84–7.75 (m, 2H), 7.65 (m, 1H), 7.58 (d, 1H, J=7.3 Hz), 7.34–7.23 (m, 2H), 7.16–7.12 (m, 2H), 2.69 (t, 2H, J=7.5 Hz), 1.71 (p, 2H, J=6.9 Hz), 1.42–1.25 (m, 4H), and 0.83 ppm (t, 3H, J=6.9 Hz). Elemental Analysis for $C_{23}H_{22}O_2$.0.2$H_2O$: Calculated: C, 82.70; H, 6.76; N, 0.00. Found: C, 82.82; H, 6.73; N, 0.09.

Step 4

[6-(3-Pentyl-benzofuran-2-yl)-naphthalen-2-yloxy]-acetonitrile

Following the procedure described in Method B, Step 5 of Example 1, [6-(3-Pentyl-benzofuran-2-yl)-naphthalen-2-yloxy]-acetonitrile was prepared from 6-(3-pentyl-benzofuran-2-yl)-naphthalen-2-ol (0.33 g, 1.0 mmol), cesium carbonate (0.75 g, 2.3 mmol), and bromo acetonitrile (0.1 mL, 1.3 mmol) in acetone (20 mL). Extraction of the residue with hot hexane and evaporation of the solvent furnished the title compound (0.23 g). $^1$HNMR (300 MHz, DMSO-$d_6$): δ8.29 (s, 1H), 8.08 (d, 1H, J=9.0 Hz), 8.00 (d, 1H, J=9.0 Hz), 7.92 (dd, 1H, J=8.8, 1.5 Hz), 7.64–7.56 (m, 2H), 7.38–7.25 (m, 3H), 5.35 (s, 2H), 2.98 (t, 2H, J=7.3 Hz), 1.72 (p, 2H, J=7.0 Hz), 1.42–1.28 (m, 4H), and 0.83 ppm (t, 3H, J=7.1 Hz).

Step 5

5-[6-(3-Pentyl-benzofuran-2-yl)-naphthalen-2-yloxymethyl]-1H-tetrazole

Following the procedure described in Step 6, of Example 1, the title compound was prepared from [6-(3-pentyl-benzofuran-2-yl)-naphthalen-2-yloxy]-acetonitrile (0.2 g, 0.54 mmol), sodium azide (0.35 g, 5.4 mmol) and ammonium chloride (0.29 g, 5.4 mmol) in DMF (12 mL). The title compound was obtained as a white solid (0.085 g), mp 178–180° C. Mass spectrum (+APCl, [M+H]$^+$) m/z 413. $^1$HNMR (400 MHz, DMSO-$d_6$): δ8.27 (s, 1H), 8.03 (d, 1H, J=9.1 Hz), 7.97–7.87 (m, 2H), 7.68 (d, 1H, J=7.0 Hz), 7.61–7.56 (m, 2H), 7.36–7.25 (m, 3H), 5.63 (s, 2H), 2.96 (t, 2H, J=7.9 Hz), 1.72 (p, 2H, J=7.0 Hz), 1.41–1.29 (m, 4H), and 0.83 ppm (t, 3H, J=7.1 Hz). Elemental Analysis for $C_{25}H_{24}N_4O_2 \cdot 0.75H_2O$: Calculated: C, 70.49; H, 6.03; N, 13.15. Found: C, 70.18; H, 5.68; N, 13.3.

EXAMPLE 35

[6-(3-Pentyl-benzofuran-2-yl)-naphthalen-2-yloxy]-acetic acid

Step 1

[6-(3-Pentyl-benzofuran-2-yl)-naphthalen-2-yloxy]-acetic acid ethyl ester

Following the procedure described in Method B, Step 5 of Example 1, the title compound was prepared from 6-(3-pentyl-benzofuran-2-yl)-naphthalen-2-ol (0.33 g, 1 mmol), cesium carbonate (0.75 g, 2.3 mmol), ethyl bromoacetate (0.16 mL, 1.4 mmol) in acetone (20 mL). Crystallization from hexane furnished the title compound as a white solid (0.39 g), mp 84–86° C. Mass spectrum (+APCl, [M+H]$^+$) m/z 417. $^1$HNMR (300 MHz, DMSO-$d_6$): δ8.25 (s, 1H), 8.00 (d, 1H, J=9.1 Hz), 7.94–7.84 (m, 2H), 7.69–7.66 (m, 1H), 7.60 (d, 1H, J=7.5 Hz), 7.35–7.25 (m, 4H), 4.93 (s, 2H), 4.20 (q, 2H, J=7.1 Hz), 2.98 (t, 2H, J=7.3 Hz), 1.72 (p, 2H, J=7.3 Hz), 1.43–1.28 (m, 4H), 1.23 (t, 3H, J=7.2 Hz), and 0.83 ppm (t, 3H, J=7.1 Hz). Elemental Analysis for $C_{27}H_{28}O_4 \cdot 0.5H_2O$: Calculated: C, 76.21; H, 6.87; N, 0.00. Found: C, 76.48; H, 6.69; N, 0.12.

Step 2

[6-(3-Pentyl-benzofuran-2-yl)-naphthalen-2-yloxy]-acetic acid

Following the procedure described in Step 4 of Example 6, [6-(3-Pentyl-benzofuran-2-yl)-naphthalen-2-yloxy]-acetic acid ethyl ester (0.34 g, 0.82 mmol), was hydrolyzed with potassium hydroxide (0.50 g, 8.9 mmol) in THF (20 mL) and water (10 mL). The title compound was obtained as an off-white solid (0.28 g), mp 163–165° C. Mass spectrum (+APCl, [M+H]$^+$) m/z 389. $^1$HNMR (400 MHz, DMSO-$d_6$): δ13.15 (br s, 1H), 8.24 (s, 1H), 7.99 (d, 1H, J=9.0 Hz), 7.93 (d, 1H, J=8.8 Hz), 7.85 (dd, 1H, J=8.5, 1.7 Hz), 7.69–7.66 (m, 1H), 7.59 (d, 1H, J=7.8 Hz), 7.35–7.25 (m, 4H), 4.82 (s, 2H), 2.98 (t, 2H, J=7.6 Hz), 1.72 (p, 2H, J=7.3 Hz), 1.42–1.27 (m, 4H), and 0.83 ppm (t, 3H, J=7.1 Hz). Elemental Analysis for $C_{25}H_{24}O_4 \cdot 0.4H_2O$: Calculated: C, 75.89; H, 6.32; N, 0.00. Found: C, 75.9; H, 6.07; N, 0.17.

EXAMPLE 36

[1-Bromo-6-(3-pentyl-benzofuran-2-yl)-naphthalen-2-yloxy]-acetic acid

Step 1

1-Bromo-6-(3-pentyl-benzofuran-2-yl)-naphthalen-2-ol

Following the procedure described in Step 4 of Example 1, 6-(3-pentyl-benzofuran-2-yl)-naphthalen-2-ol (3.3 g, 10.0 mmol) was brominated using bromine (0.6 mL, 11.8 mmol), and potassium acetate (1.0 g. 10.2 mmol) in glacial acetic acid (40 mL). Purification by chromatography on a Biotage apparatus using 5% % ethyl acetate in hexane as the mobile phase furnished the title compound as an off-white solid (3.6 g), mp 75–77° C. Mass spectrum (+APCl, [M+H]$^+$) m/z 409. $^1$HNMR (300 MHz, DMSO-$d_6$): δ10.76 (br s,1H), 8.25 (d, 1H, J=1.2 Hz), 8.14 (d, 1H, J=8.9 Hz), 7.98–7.92 (m, 2H), 7.68–7.58 (m, 2H), 7.35–7.27 (m, 3H), 2.98 (t, 2H, J=7.3 Hz), 1.71 (p, 2H, J=6.9 Hz), 1.42–1.27 (m, 4H), and 0.87–0.80 ppm (tm 3H). Elemental Analysis for $C_{23}H_{21}BrO_2 \cdot 0.7H_2O$: Calculated: C, 65.47; H, 5.35; N, 0.00. Found: C, 65.17; H, 4.92; N, 0.08.

Step 2

[1-Bromo-6-(3-pentyl-benzofuran-2-yl)-naphthalen-2-yloxy]-acetic acid ethyl ester Following the procedure described in Method B, Step 5 of Example 1, the title compound was prepared from 1-bromo-6-(3-pentyl-benzofuran-2-yl)-naphthalen-2-ol (1.5 g, 3.66 mmol), cesium carbonate (2.4 g, 7.34 mmol), ethyl bromoacetate (0.48 mL, 4.3 mmol) in acetone (35 mL). The title compound was obtained as an off-white solid (1.6 g), mp 93–95° C. Mass spectrum (+APCl, [M+H]$^+$) m/z 495. $^1$HNMR (300 MHz, DMSO-$d_6$): δ8.34 (s, 1H), 8.24 (d, 1H, J=9.0 Hz), 8.12 (d, 1H, J=9.1 Hz), 8.06–8.02 (m, 1H), 7.69 (d, 1H, J=7.1 Hz), 7.61 (d, 1H, J=7.7 Hz), 7.48 (d, 1H, J=9.1 Hz), 7.37–7.26 (m, 2H), 5.1 (s, 2H), 4.18 (q, 2H, J=7.1 Hz), 3.01 (t, 2H, J=7.3 Hz), 1.76–1.64 (m, 2H), 1.43–1.26 (m, 4H), 1.22 (t, 3H, J=7.1 Hz), and 0.85–0.79 ppm (m, 3H). Elemental Analysis for $C_{27}H_{27}BrO_4 \cdot 1.0H_2O$: Calculated: C, 63.16; H, 5.69; N, 0.00. Found: C, 62.90; H, 5.19; N, 0.15.

Step 3

[1-Bromo-6-(3-pentyl-benzofuran-2-yl)-naphthalen-2-yloxy]-acetic acid

Following the procedure described in Step 4 of Example 6, [1-bromo-6-(3-pentyl-benzofuran-2-yl)-naphthalen-2-yloxy]-acetic acid ethyl ester (1.25 g, 2.53 mmol), was hydrolyzed with potassium hydroxide (0.70 g, 12.5 mmol)

in THF (30 mL) and water (10 mL). Crystallization from ethyl acetate/hexane furnished the title compound as an off-white solid (0.90 g), mp 159–161° C. Mass spectrum (+APCl, [M+H]+) m/z 467. ¹HNMR (400 MHz, DMSO-$d_6$): δ13.2 (br s, 1H), 8.32 (d, 1H, J=1.5 Hz), 8.22 (d, 1H, J=9.0 Hz), 8.10 (d, 1H, J=9.0 Hz), 8.03 (dd, 1H, J=9.0, 1.5 Hz), 7.69–7.67 (m, 1H), 7.61 (d, 1H, J=8.0 Hz), 7.45 (d, 1H, J=9.0 Hz), 7.35–7.28 (m, 2H), 5.00 (s, 2H), 3.00 (t, 2H, J=7.8 Hz), 1.75–1.66 (m, 2H), 1.40–1.27 (m, 4H), and 0.84–0.79 ppm (m, 3H). Elemental Analysis for $C_{25}H_{23}BrO_2 \cdot 1.0H_2O$: Calculated: C, 61.86; H, 5.19; N, 0.00. Found: C, 61.87; H, 4.70; N, 0.04.

EXAMPLE 37

5-[6-(3-Pentyl-benzofuran-2-yl)-naphthalen-2-yloxymethyl]-1H-tetrazole

Step 1

[1-Bromo-6-(3-pentyl-benzofuran-2-yl)-naphthalen-2-yloxy]-acetonitrile

Following the procedure described in Method B, Step 5 of Example 1, [1-bromo-6-(3-pentyl-benzofuran-2-yl)-naphthalen-2-yloxy]-acetonitrile was prepared from 1-bromo-6-(3-pentyl-benzofuran-2-yl)-naphthalen-2-ol (1.5 g, 3.66 mmol), cesium carbonate (2.4 g, 7.34 mmol), and bromo acetonitrile (0.3 mL, 4.3 mmol) in acetone (35 mL). Crystallization from methanol furnished the title compound as a solid (1.4 g), mp 111–113° C. Mass spectrum (+APCl, [M+H]+) m/z 448. ¹HNMR (300 MHz, DMSO-$d_6$): δ8.40 (d, 1H, J=1.2 Hz), 8.28–8.23 (m, 2H), 8.09 (dd, 1H, J=8.9, 1.6 Hz), 7.72–7.60 (m, 3H), 7.39–7.27 (m, 2H), 5.45 (s, 2H), 3.02 (t, 2H, J=7.5 Hz), 1.72 (p, 2H, J=7.3 Hz), 1.42–1.28 (m, 4H), and 0.85–0.80 ppm (m, 3H). Elemental Analysis for $C_{25}H_{24}N_4O_2 \cdot 0.75H_2O$: Calculated: C, 59.47; H, 4.89; N, 11.09. Found: C, 59.51; H, 4.60; N, 11.09.

Step 2

5-[6-(3-Pentyl-benzofuran-2-yl)-naphthalen-2-yloxymethyl]-1H-tetrazole

Following the procedure described in Step 6, of Example 1, the title compound was prepared from [1-bromo-6-(3-pentyl-benzofuran-2-yl)-naphthalen-2-yloxy]-acetonitrile (1.23 g, 2.75 mmol), sodium azide (1.8 g, 27.5 mmol) and ammonium chloride (1.45 g, 27.5 mmol) in DMF (30 mL). Crystallization from methanol afforded the title compound as an off-white solid (0.75 g), mp 192–194° C. Mass spectrum (+APCl, [M+H]+) m/z 491. ¹HNMR (400 MHz, DMSO-$d_6$): δ8.36 (d, 1H, J=1.5 Hz), 8.23–8.17 (m, 2H), 8.05 (dd, 1H, J=9.0, 1.7 Hz), 7.72–7.68 (m, 2H), 7.61 (m, 1H, J=8.1 Hz), 7.37–7.27 (m, 2H), 5.75 (s, 2H), 3.00 (t, 2H, J=7.8 Hz), 1.74–1.767 (m, 2H), 1.42–1.26 (m, 4H), and 0.84–0.80 ppm (m, 3H). Elemental Analysis for $C_{25}H_{24}N_4O_2 \cdot 0.75H_2O$: Calculated: C, 59.47; H, 4.89; N, 11.09. Found: C, 59.51; H, 4.6; N, 11.09.

What is claimed:

1. A compound of formula 1:

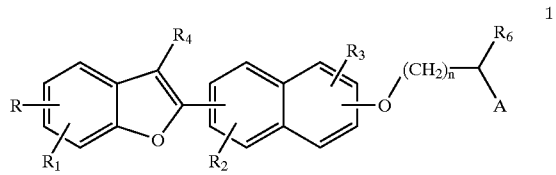

wherein:

R, $R_1$, $R_2$, and $R_3$ are independently selected from hydrogen, $C_1$–$C_6$ alkyl, $C_3$–$C_6$ cycloalkyl, —$CH_2$—($C_3$–$C_6$ cycloalkyl), $C_1$–$C_6$ alkanoyl, halo, hydroxy, aryl, substituted aryl, heteroaryl, substituted heteroaryl, perfluoroalkyl of 1–6 carbon atoms, alkoxy of 1–6 carbon atoms, amino, —NH(alkyl of 1–6 carbon atoms), —N(alkyl of 1–6 carbon atoms)$_2$, or perfluoroalkoxy of 1–6 carbon atoms;

$R_4$ is hydrogen, alkyl of 1–6 carbon atoms, branched alkyl of 1–6 carbon atoms, perflouroalkyl, aryl, substituted aryl, heteroaryl, substituted heteroaryl, alkenyl, alkenyl-aryl, —$CH_2R_5$, —$CH(OH)R_5$, —$C(O)R_5$, —$CH(SH)R_5$, or —$C(S)R_5$ or —$(CH_2)_n$—$C_3$ to $C_6$ cycloalkyl wherein n is an integer of from 0 to 2;

$R_5$ is hydrogen, alkyl of 1–6 carbon atoms, branched alkyl of 1–6 carbon atoms, perflouroalkyl, aryl, substituted aryl, heteroaryl, substituted heteroaryl, alkenyl, alkenyl-aryl or —$(CH_2)_n$—$C_3$ to $C_6$ cycloalkyl wherein n is an integer of from 0 to 2;

$R_6$ is selected from hydrogen, alkyl of 1–6 carbon atoms, cycloalkyl of 3 to 6 carbon atoms, —$CH_2$-cycloalkyl of 3 to 6 carbon atoms, alkylaryl, aryl, substituted aryl, heteroaryl, or substituted heteroaryl;

n is an integer of 0–6;

A is COOH, or an acid mimic;

or a pharmaceutically acceptable salt or ester form thereof.

2. A compound of claim 1 wherein the acid mimic of A is selected from the group of tetrazole, $SO_3H$, $PO_3H_2$, tetronic acid, or a group of the formulae:

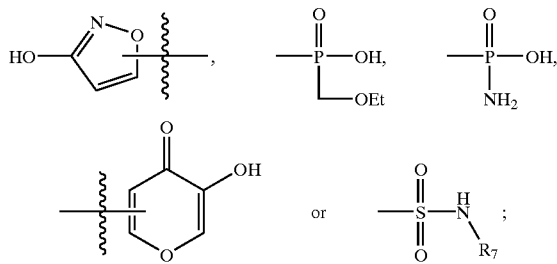

wherein $R_7$ is $C_1$–$C_6$ alkyl, $C_2$–$C_6$ alkenyl, $C_3$–$C_6$ cycloalkyl, —$CH_2$—($C_3$–$C_6$ cycloalkyl), $C_3$–$C_6$ cycloalkenyl, —$CH_2$—($C_3$–$C_6$ cycloalkenyl), optionally substituted aryl or heteroaryl groups or optionally substituted —$C_1$–$C_6$ alkyl-aryl or —$C_1$–$C_6$ alkyl-heteroaryl.

3. A compound of claim 1 of formula 2:

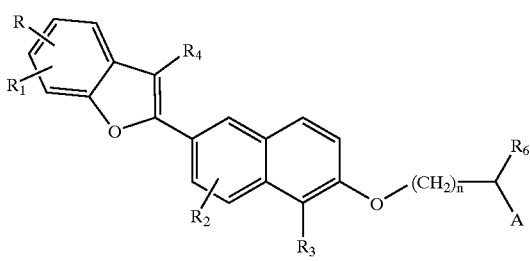

wherein R, R₁, R₂, R₃, R₄, R₆, A, and n are as defined in claim 1, or a pharmaceutically acceptable salt or ester form thereof.

4. A compounds of claim 1 of formula 3:

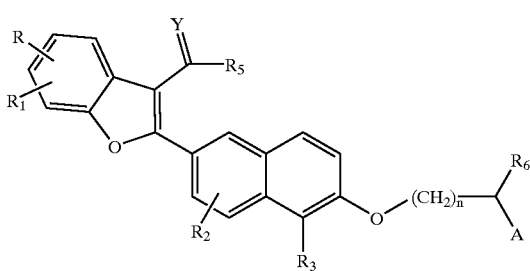

wherein R, R₁, R₂, and R₃, are as defined in claim 1, N=0
A is a carboxylic acid or a tetrazole group'
R₆ is a hydrogen, $C_1$–$C_6$ alkyl or benzyl optionally substituted by from 1 to 3 groups selected from halogen, $C_1$–$C_3$ alkyl, $C_1$–$C_3$ perfluoroalkyl, preferably—$CF_3$, —O—$C_1$–$C_3$ perfluoroalkyl, preferably —O—$CF_3$, $C_1$–$C_3$ alkoxy, —OH, —$NH_2$, or —$NO_2$;
Y represents two single bonded H atoms; one H and one OH; or a double bonded oxygen atom; and
R₅ is selected from $C_1$–$C_8$ alkyl, preferably $C_1$–$C_6$ alkyl, $C_3$–$C_6$ cycloalkyl, —$CH_2$—$C_3$–$C_6$ cycloalkyl, or benzyl, the rings of the cycloalkyl and benzyl groups being optionally substituted by from 1 to 3 groups selected from halogen, $C_1$–$C_3$ alkyl, $C_1$–$C_3$ perfluoroalkyl, preferably —$CF_3$, —O—$C_1$–$C_3$ perfluoroalkyl, preferably —O—$CF_3$, $C_1$–$C_3$ alkoxy, —OH, —$NH_2$, or —$NO_2$;
or a pharmaceutically acceptable salt or ester form thereof.

5. A compound of claim 1 which is 1-{2-[5-Bromo-6-(1H-1,2,3,4-tetraazol-5-ylmethoxy)-2-naphthyl]-1-benzofuran-3-yl}-1-pentanone or a pharmaceutically acceptable salt or ester form thereof.

6. A compound of claim 1 which is 2-{[6-(3-pentanoyl-1-benzofuran-2-yl)-2-naphthyl]oxy}acetic acid or a pharmaceutically acceptable salt or ester form thereof.

7. A compound of claim 1 which is 1-{2-[6-(1H-1,2,3,4-Tetraazol-5-ylmethoxy)-2-naphthyl]-1-benzofuran-3-yl}-1-pentanone or a pharmaceutically acceptable salt or ester form thereof.

8. A compound of claim 1 which is 2-{[6-(3-Pentanoyl-1-benzofuran-2-yl)-2-naphthyl]oxy}-3-phenylpropanoic acid or a pharmaceutically acceptable salt or ester form thereof.

9. A compound of claim 1 which is 2-{[1-Bromo-6-(3-pentanoyl-1-benzofuran-2-yl)-2-naphthyl]oxy}acetic acid or a pharmaceutically acceptable salt or ester form thereof.

10. A compound of claim 1 which is 2-({6-[3-(3,3-Dimethylbutanoyl)-1-benzofuran-2-yl]-2-naphthyl}oxy) acetic acid or a pharmaceutically acceptable salt or ester form thereof.

11. A compound of claim 1 which is 2-({4-Bromo-6-[3-(3-methylbutanoyl)-1-benzofuran-2-yl]-2-naphthyl}oxy) acetic acid or a pharmaceutically acceptable salt or ester form thereof.

12. A compound of claim 1 which is 2-({1-Bromo-6-[3-(3,3-dimethylbutanoyl)-1-benzofuran-2-yl]-2-naphthyl}oxy)acetic acid or a pharmaceutically acceptable salt or ester form thereof.

13. A compound of claim 1 which is 1-{2-[5-Bromo-6-(1H-1,2,3,4-tetraazol-5-ylmethoxy)-2-naphthyl]-1-benzofuran-3-yl}-3-methyl-1-butanone or a pharmaceutically acceptable salt or ester form thereof.

14. A compound of claim 1 which is 2-({6-[3-(2-Cyclopentylacetyl)-1-benzofuran-2-yl]-2-naphthyl}oxy) acetic acid or a pharmaceutically acceptable salt or ester form thereof.

15. A compound of claim 1 which is 2-({1-Bromo-6-[3-(2-cyclopentylethyl)-1-benzofuran-2-yl]-2-naphthyl}oxy) acetic acid or a pharmaceutically acceptable salt or ester form thereof.

16. A compound of claim 1 which is 5-[({1-Bromo-6-[3-(2-cyclopentylethyl)-1-benzofuran-2-yl]-2-naphthyl}oxy) methyl]-1H-1,2,3,4-tetraazole or a pharmaceutically acceptable salt or ester form thereof.

17. A compound of claim 1 which is 1-{2-[5-Bromo-6-(1H-1,2,3,4-tetraazol-5-ylmethoxy)-2-naphthyl]-1-benzofuran-3-yl}-2-cyclopentyl-1-ethanone or a pharmaceutically acceptable salt or ester form thereof.

18. A compound of claim 1 which is 2-{[6-(3-Pentanoyl-1-benzofuran-2-yl)-1-phenyl-2-naphthyl]oxy}acetic acid, sodium salt or a pharmaceutically acceptable salt or ester form thereof.

19. A compound of claim 1 which is 2-({6-(3-Pentanoyl-1-benzofuran-2-yl)-1-[4-(trifluoromethyl)phenyl]-2-naphthyl}oxy) acetic acid or a pharmaceutically acceptable salt or ester form thereof.

20. A compound of claim 1 which is 1-{2-[5-Phenyl-6-(1H-1,2,3,4-tetraazol-5-ylmethoxy)-2-naphthyl]-1-benzofuran-3-yl}-1-pentanone or a pharmaceutically acceptable salt or ester form thereof.

21. A compound of claim 1 which is 2-({1-Bromo-6-[3-(2-cyclopentylacetyl)-1-benzofuran-2-yl]-2-naphthyl}oxy) acetic acid or a pharmaceutically acceptable salt or ester form thereof.

22. A compound of claim 1 which is 1-(2-{6-(1H-1,2,3,4-Tetraazol-5-ylmethoxy)-5-[4-(trifluoromethyl)phenyl]-2-naphthyl}-1-benzofuran-3-yl)-1-pentanone or a pharmaceutically acceptable salt or ester form thereof.

23. A compound of claim 1 which is 2-{[1-Bromo-6-(3-pentanoyl-1-benzofuran-2-yl)-2-naphthyl]oxy}-3-phenylpropanoic acid or a pharmaceutically acceptable salt or ester form thereof.

24. A compound of claim 1 which is 1-{2-[5-Methyl-6-(1H-1,2,3,4-tetraazol-5-ylmethoxy)-2-naphthyl]-1-benzofuran-3-yl}-1-pentanone or a pharmaceutically acceptable salt or ester form thereof.

25. A compound of claim 1 which is 5-({[1-Methyl-6-(3-pentyl-1-benzofuran-2-yl)-2-naphthyl]oxy}methyl)-1H-1,2,3,4-tetraazole or a pharmaceutically acceptable salt or ester form thereof.

26. A compound of claim 1 which is 2-{[1-Methyl-6-(3-pentanoyl-1-benzofuran-2-yl)-2-naphthyl]oxy}acetic acid or a pharmaceutically acceptable salt or ester form thereof.

27. A compound of claim 1 which is 2-{[1-Methyl-6-(3-pentanoyl-1-benzofuran-2-yl)-2-naphthyl]oxy}-3-phenylpropanoic acid or a pharmaceutically acceptable salt or ester form thereof.

28. A compound of claim 1 which is 2-{[1-Chloro-6-(3-pentanoyl-1-benzofuran-2-yl)-2-naphthyl]oxy}acetic acid or a pharmaceutically acceptable salt or ester form thereof.

29. A compound of claim 1 which is 1-{2-[5-Chloro-6-(1H-1,2,3,4-tetraazol-5-ylmethoxy)-2-naphthyl]-1-benzofuran-3-yl}-1-pentanone or a pharmaceutically acceptable salt or ester form thereof.

30. A compound of claim 1 which is {[6-(3-benzoyl-1-benzofuran-2-yl)-2-naphthyl]oxy}acetic acid or a pharmaceutically acceptable salt or ester form thereof.

31. A compound of claim 1 which is {2-[5-Bromo-6-(1H-tetraazol-5-ylmethoxy)-2-naphthyl]-1-benzofuran-3-yl}(phenyl) methanone or a pharmaceutically acceptable salt or ester form thereof.

32. A compound of claim 1 which is 2-{[1-Bromo-6-(3-bromo-1-benzofuran-2-yl)-2-naphthyl]oxy}-3-phenylpropanoic acid or a pharmaceutically acceptable salt or ester form thereof.

33. A compound of claim 1 which is {[1-Phenyl-6-(3-phenyl-1-benzofuran-2-yl)-2-naphthyl]oxy}acetic acid or a pharmaceutically acceptable salt or ester form thereof.

34. A compound of claim 1 which is 1-{2-[5-Bromo-6-(1H-tetrazol-5-ylmethoxy)-naphthalen-2-yl]-5-chloro-benzofuran-3-yl}-pentan-1-one or a pharmaceutically acceptable salt or ester form thereof.

35. A compound of claim 1 which is [1-Bromo-6-(5-chloro-3-pentanoyl-benzofuran-2-yl)-naphthalen-2-yloxy]-acetic acid or a pharmaceutically acceptable salt or ester form thereof.

36. A compound of claim 1 which is 1-{5-Chloro-2-[6-(1H-tetrazol-5-ylmethoxy)-naphthalen-2-yl]-benzofuran-3-yl}-pentan-1-one or a pharmaceutically acceptable salt or ester form thereof.

37. A compound of claim 1 which is [6-(5-Chloro-3-pentanoyl-benzofuran-2-yl)-naphthalen-2-yloxy]-acetic acid or a pharmaceutically acceptable salt or ester form thereof.

38. A compound of claim 1 which is 5-[6-(3-Pentyl-benzofuran-2-yl)-naphthalen-2-yloxymethyl]-1H-tetrazole or a pharmaceutically acceptable salt or ester form thereof.

39. A compound of claim 1 which is [6-(3-Pentyl-benzofuran-2-yl)-naphthalen-2-yloxy]-acetic acid or a pharmaceutically acceptable salt or ester form thereof.

40. A compound of claim 1 which is [1-Bromo-6-(3-pentyl-benzofuran-2-yl)-naphthalen-2-yloxy]-acetic acid or a pharmaceutically acceptable salt or ester form thereof.

41. A compound of claim 1 which is 5-[6-(3-Pentyl-benzofuran-2-yl)-naphthalen-2-yloxymethyl]-1H-tetrazole or a pharmaceutically acceptable salt or ester form thereof.

42. A method for treatment of thrombosis or fibrinolytic impairment in a mammal, the method comprising administering to a mammal in need thereof a pharmaceutically effective amount of a compound of claim 1.

43. A method of claim 42 wherein the thrombosis or fibrinolytic impairment is associated with formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion.

44. A pharmaceutical composition comprising pharmaceutically effective amount of a compound of claim 1, or a pharmaceutically acceptable salt or ester form thereof, and a pharmaceutically acceptable excipient or carrier.

45. A method for the treatment of stroke associated with or resulting from atrial fibrillation in a mammal, comprising administering to a mammal in need thereof a pharmaceutically effective amount of a compound of claim 1.

46. A method for the treatment of deep vein thrombosis in a mammal, comprising administering to a mammal in need thereof a pharmaceutically effective amount of a compound of claim 1.

47. A method for the treatment of myocardial ischemia in a mammal, comprising administering to a mammal in need thereof a pharmaceutically effective amount of a compound of claim 1.

48. A method for the treatment of cardiovascular disease caused by noninsulin dependent diabetes mellitus in a mammal, comprising administering to a mammal in need thereof a pharmaceutically effective amount of a compound of claim 1.

49. A method for the treatment of the formation of atherosclerotic plaques in a mammal, comprising administering to a mammal in need thereof a pharmaceutically effective amount of a compound of claim 1.

50. A method for the treatment of chronic obstructive pulmonary disease in a mammal, comprising administering to a mammal in need thereof a pharmaceutically effective amount of a compound of claim 1.

51. A method for the treatment of renal fibrosis in a mammal, comprising administering to a mammal in need thereof a pharmaceutically effective amount of a compound of claim 1.

52. A method for the treatment of polycystic ovary syndrome in a mammal, comprising administering to a mammal in need thereof a pharmaceutically effective amount of a compound of claim 1.

53. A method for the treatment of Alzheimer's disease in a mammal, comprising administering to a mammal in need thereof a pharmaceutically effective amount of a compound of claim 1.

54. A method for the treatment of cancer in a mammal, comprising administering to a mammal in need thereof a pharmaceutically effective amount of a compound of claim 1.

* * * * *